United States Patent
Cizeron et al.

(10) Patent No.: US 10,836,689 B2
(45) Date of Patent: Nov. 17, 2020

(54) SYSTEMS AND METHODS FOR THE OXIDATIVE COUPLING OF METHANE

(71) Applicant: Lummus Technology LLC, The Woodlands, TX (US)

(72) Inventors: Joel Cizeron, Redwood City, CA (US); David Sheridan, Menlo Park, CA (US); Gregory J. Turk, Oakland, CA (US); Satish Lakhapatri, San Francisco, CA (US); Rong Fan, Castro Valley, CA (US); Guido Radaelli, Pleasant Hill, CA (US); Franciscus J. A. Martens, Calgary (CA); Jarod McCormick, Palo Alto, CA (US); David C. Grauer, San Francisco, CA (US); Fabio R. Zurcher, Brisbane, CA (US); Daniel Rosenberg, San Francisco, CA (US)

(73) Assignee: Lummus Technology LLC, The Woodlands, TX (US)

( * ) Notice: Subject to any disclaimer, the term of this patent is extended or adjusted under 35 U.S.C. 154(b) by 0 days.

(21) Appl. No.: 16/030,298

(22) Filed: Jul. 9, 2018

(65) Prior Publication Data

US 2019/0169089 A1    Jun. 6, 2019

Related U.S. Application Data

(60) Provisional application No. 62/557,597, filed on Sep. 12, 2017, provisional application No. 62/530,639, (Continued)

(51) Int. Cl.
C07C 2/84      (2006.01)
B01J 8/06      (2006.01)
(Continued)

(52) U.S. Cl.
CPC ............. *C07C 2/84* (2013.01); *B01J 8/025* (2013.01); *B01J 8/0415* (2013.01); *B01J 8/06* (2013.01);
(Continued)

(58) Field of Classification Search
None
See application file for complete search history.

(56) References Cited

U.S. PATENT DOCUMENTS 2,324,172 A    7/1943   Parkhurst
2,486,980 A    11/1949  Robinson
(Continued)

FOREIGN PATENT DOCUMENTS

CA    2041874 A1    11/1992
CA    2765769 A1     1/2011
(Continued)

OTHER PUBLICATIONS

Agarwal, et al., Aqueous Au—Pd colloids catalyze selective CH4 oxidation to CH3OH with O2 under mild conditions, Science 358, Oct. 13, 2017, 223-27.

(Continued)

*Primary Examiner* — Tam M Nguyen
(74) *Attorney, Agent, or Firm* — Calfee, Halter & Griswold LLP

(57) ABSTRACT

The present disclosure provides systems and methods for producing olefins via an oxidative coupling of methane (OCM) process. The systems and methods may comprise the use of a staged process comprising at least one non-adiabatic section that is in thermal communication with a heat transfer medium and at least one substantially adiabatic section. The systems and methods may also comprise the use of a diluent stream which may improve methane conversion in an OCM reactor and an ethylene/ethane ratio in a post-bed cracking (Continued)

unit. The methods and systems may further comprise injecting oxygen ($O_2$) and a paraffin into a gas stream containing a radical transfer agent to provide a reaction mixture. The reaction mixture may be held in a vessel for a time period greater than an auto-ignition delay time (AIDT), such that the reaction mixture may ignite to liberate heat and convert to a product mixture comprising olefins.

19 Claims, 38 Drawing Sheets

Related U.S. Application Data filed on Jul. 10, 2017, provisional application No. 62/529,942, filed on Jul. 7, 2017.

(51) Int. Cl.
  *B01J 8/02* (2006.01)
  *B01J 19/00* (2006.01)
  *B01J 8/04* (2006.01)
  *B01J 12/00* (2006.01)
  *B01J 19/24* (2006.01)

(52) U.S. Cl.
  CPC ............. *B01J 8/067* (2013.01); *B01J 12/007* (2013.01); *B01J 19/0093* (2013.01); *B01J 19/242* (2013.01); *B01J 2208/00017* (2013.01); *B01J 2208/0053* (2013.01); *B01J 2208/00212* (2013.01); *B01J 2208/00495* (2013.01); *B01J 2208/00539* (2013.01); *B01J 2208/00548* (2013.01); *B01J 2208/00911* (2013.01); *B01J 2208/021* (2013.01); *B01J 2208/025* (2013.01); *B01J 2219/0079* (2013.01); *B01J 2219/00788* (2013.01); *C07C 2521/04* (2013.01); *C07C 2521/06* (2013.01); *C07C 2523/02* (2013.01); *C07C 2523/10* (2013.01)

(56) References Cited

U.S. PATENT DOCUMENTS

| | | |
|---|---|---|
| 2,577,701 A | 12/1951 | Deming et al. |
| 2,579,601 A | 12/1951 | Nelson et al. |
| 2,621,216 A | 12/1952 | White |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hagemeyer, Jr. et al. |
| 3,584,071 A | 6/1971 | Mcnulty et al. |
| 3,596,473 A | 8/1971 | Streich |
| 3,660,519 A | 5/1972 | Arakawa et al. |
| 3,686,334 A | 8/1972 | Britton |
| 3,686,350 A | 8/1972 | Ono et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,882,400 A | 11/1989 | Dumain et al. |
| 4,891,457 A | 1/1990 | Owen et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,254,781 A | 10/1993 | Calamur et al. |
| 5,263,998 A | 11/1993 | Mackrodt et al. |

(56) References Cited

U.S. PATENT DOCUMENTS

| | | |
|---|---|---|
| 5,288,935 A | 2/1994 | Alario et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | Devries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Truebenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | MacKay et al. |
| 6,153,149 A | 11/2000 | Rabitz et al. |
| 6,221,986 B1 | 4/2001 | Commereuc et al. |
| 6,328,945 B1 | 12/2001 | Hutton et al. |
| 6,342,149 B1 | 1/2002 | Köster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |

(56) References Cited

U.S. PATENT DOCUMENTS

| | | |
|---|---|---|
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 * | 5/2016 | Nyce ................... B01J 8/0278 |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 * | 9/2019 | Radaelli .................... C07C 2/84 |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1 | 6/2008 | Bozzano et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |

(56) References Cited

U.S. PATENT DOCUMENTS

| | | |
|---|---|---|
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2013/0023079 A1 | 1/2013 | Kang et al. |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1* | 1/2014 | Iyer .................. C07C 2/84 585/330 |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1* | 6/2015 | Cizeron .................. C07C 2/84 585/324 |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Nyce et al. |
| 2016/0376148 A1* | 12/2016 | Mamedov .................. C07C 2/82 252/373 |
| 2017/0014807 A1* | 1/2017 | Liang .................. B01J 37/0236 |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1* | 10/2017 | Radaelli .................. C07C 2/84 |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1* | 10/2018 | Patel .................. B01J 8/067 |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0119182 A1 | 4/2019 | McCormick et al. |
| 2019/0143288 A1 | 5/2019 | Bao et al. |
| 2019/0169090 A1 | 6/2019 | Sarsani et al. |
| 2019/0177246 A1 | 6/2019 | Nyce et al. |
| 2019/0389788 A1* | 12/2019 | Mamedov .................. C07C 5/42 |
| 2020/0031734 A1 | 1/2020 | Cizeron et al. |
| 2020/0031736 A1 | 1/2020 | Weinberger et al. |
| 2020/0048165 A1 | 2/2020 | Duggal et al. |
| 2020/0055796 A1 | 2/2020 | Nyce et al. |
| 2020/0071242 A1 | 3/2020 | Patel et al. |
| 2020/0172452 A1 | 6/2020 | Duggal et al. |
| 2020/0189994 A1 | 6/2020 | Radaelli et al. |

FOREIGN PATENT DOCUMENTS

| | | |
|---|---|---|
| CA | 2800142 C | 6/2018 |
| CN | 1403375 A | 3/2003 |
| CN | 101224432 A | 7/2008 |
| CN | 101387019 A | 3/2009 |
| CN | 101747927 A | 6/2010 |
| CN | 102093157 A | 6/2011 |
| CN | 102125825 A | 7/2011 |
| DE | 1905517 A1 | 8/1970 |
| DE | 2540257 A1 | 4/1977 |
| DE | 3406751 A1 | 8/1985 |

(56) References Cited

FOREIGN PATENT DOCUMENTS

| | | |
|---|---|---|
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 0253522 A2 | 1/1988 |
| EP | 0303438 A2 | 2/1989 |
| EP | 336823 A1 | 10/1989 |
| EP | 0608447 A1 | 8/1994 |
| EP | 0634211 A1 | 1/1995 |
| EP | 0722822 A1 | 7/1996 |
| EP | 0761307 A1 | 3/1997 |
| EP | 0764467 A1 | 3/1997 |
| EP | 0716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | WO-8607351 A1 | 12/1986 |
| WO | WO-2002004119 A1 | 1/2002 |
| WO | WO-2004033488 A2 | 4/2004 |
| WO | WO-2004056479 A1 | 7/2004 |
| WO | WO-2004103936 A1 | 12/2004 |
| WO | WO-2005067683 A2 | 7/2005 |
| WO | 2007125360 A1 | 11/2007 |
| WO | WO-2007130515 A2 | 11/2007 |
| WO | WO-2008005055 A2 | 1/2008 |
| WO | WO-2008014841 A1 | 2/2008 |
| WO | WO-2008022147 A1 | 2/2008 |
| WO | WO-2008073143 A2 | 6/2008 |
| WO | 2008150451 A2 | 12/2008 |
| WO | 2008150451 A3 | 3/2009 |
| WO | WO-2009071463 A2 | 6/2009 |
| WO | WO-2009074203 A1 | 6/2009 |
| WO | WO-2009115805 A1 | 9/2009 |
| WO | WO-2010005453 A2 | 1/2010 |
| WO | WO-2011008464 A1 | 1/2011 |
| WO | WO-2011041184 A2 | 4/2011 |
| WO | WO-2011050359 A1 | 4/2011 |
| WO | WO-2010069488 A8 | 5/2011 |
| WO | WO-2011149996 A2 | 12/2011 |
| WO | 2012047274 A2 | 4/2012 |
| WO | 2012047274 A3 | 5/2012 |
| WO | WO-2012162526 A2 | 11/2012 |
| WO | WO-2013106771 A2 | 7/2013 |
| WO | 2013169462 A1 | 11/2013 |
| WO | 2013175204 A1 | 11/2013 |
| WO | WO-2013177433 A2 | 11/2013 |
| WO | WO-2013177461 A2 | 11/2013 |
| WO | WO-2014011646 A1 | 1/2014 |
| WO | 2014044387 A1 | 3/2014 |
| WO | WO-2014049445 A2 | 4/2014 |
| WO | 2014089479 A1 | 6/2014 |
| WO | 2013177433 A3 | 8/2014 |
| WO | 2014131435 A1 | 9/2014 |
| WO | WO-2014143880 A1 | 9/2014 |
| WO | 2015000061 A1 | 1/2015 |
| WO | 2015003193 A2 | 1/2015 |
| WO | 2015021177 A1 | 2/2015 |
| WO | WO-2015048295 A1 | 4/2015 |
| WO | WO-2015066693 A1 | 5/2015 |
| WO | WO-2015081122 A2 | 6/2015 |
| WO | WO-2015105911 A1 | 7/2015 |
| WO | WO-2015106023 A1 | 7/2015 |
| WO | WO-2015081122 A3 | 12/2015 |
| WO | WO-2016012371 A1 | 1/2016 |
| WO | WO-2016149507 A1 | 9/2016 |
| WO | WO-2016160563 A1 | 10/2016 |
| WO | 2016205411 A2 | 12/2016 |
| WO | 2016210006 A2 | 12/2016 |
| WO | 2016210006 A3 | 4/2017 |
| WO | WO-2017065947 A1 | 4/2017 |
| WO | 2016205411 A3 | 9/2017 |
| WO | WO-2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | WO-2018118105 A1 | 6/2018 |
| WO | 2019010498 A1 | 1/2019 |
| WO | 2019055220 A1 | 3/2019 |

OTHER PUBLICATIONS

American Petroleum Institute Publication 534 "Heat Recovery Steam Generators" Jan. 1995 (51 pages).

Autothermal Partial Oxidative Coupling of Methane. IP.com, Prior Art Database Technical Disclosure, Jul. 29, 2008, 5 pages.

Barrett, et al. The determination of pore volume and area distributions in porous substances—Compuatations from nitrogen isotherms. J. Am. Chem. Soc., 1951, vol. 73, pp. 373-380.

Berstad, D. et al. Low-temperature CO2 removal from natural gas. Energy Procedia (2012) 26:41-48.

Bloch, et al. Hydrocarbon Separations in a Metal-Organic Framework with Open Iron(II) Coordination Sites, Science, 2012, 335:1606-1610.

Bollmann, et al. Ethylene tetramerization: a new route to produce 1-octene in exceptionally high selectivities. J Am Chem Soc. Nov. 17, 2004;126(45):14712-3.

Botella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.

Carter, et al. High activity ethylene trimerisation catalysts based on diphosphine ligands. Chem Commun (Camb). Apr. 21, 2002;(8):858-9.

Cavani, et al. Oxidative dehydrogenation of ethane and propane: How far from commercial implementation? Catalysis Today. 2007; 127(1-4):113-131.

Chemsystems PERP Report Ethylene Oxide/Ethylene Glycol 2005.

Chen, et al. M2 Forming—A Process for Aromatization of Light Hydrocarbons. Ind. Eng. Chem. Process. Des. Dev. 1986, 25, 151-155.

Choudhary, et al. Aromatization of dilute ethylene over Ga-modified ZSM-5 type zeolite catalysts. Microporous and Mesoporous Materials 47: 253-267, 2001.

Choudhary, et al. Oxidative conversion of methane/natural gas into higher hydrocarbons. Catalysis Surveys from Asia 8(1): 15-25, Feb. 2004.

Choudhary, et al. Surface Basicity and Acidity of Alkaline Earth-Promoted La2 O3 Catalysts and Their Performance in Oxidative Coupling of Methane. Journal of Chemical Technology and Biotechnology 72:125-130, 1998.

Christopher, et al. Engineering Selectivity in Heterogeneous Catalysis: Ag Nanowires as Selective Ethylene Epoxidation Catalysts. Journal of the American Chemical Society 130: 11264-11265, 2008.

Co-pending U.S. Appl. No. 15/359,399, filed Nov. 22, 2016.
Co-pending U.S. Appl. No. 15/699,798, filed Sep. 8, 2017.
Co-pending U.S. Appl. No. 15/888,777, filed Feb. 5, 2018.
Co-pending U.S. Appl. No. 15/912,104, filed Mar. 5, 2018.
Co-pending U.S. Appl. No. 15/950,461, filed Apr. 11, 2018.
Co-pending U.S. Appl. No. 15/987,068, filed May 23, 2018.
Co-pending U.S. Appl. No. 16/021,441, filed Jun. 28, 2018.
Co-pending U.S. Appl. No. 16/035,311, filed Jul. 13, 2018.

Debart, et al. α-MNO2 Nanowires: A catalyst for the O2 Electrode in Rechargeabl Lithium Batteries. Angewandte Chemie International Edition 47: 4521-4524, 2008.

(56) References Cited

OTHER PUBLICATIONS

Enger, et al. A review of catalytic partial oxidation of methane to synthesis gas with emphasis on reaction mechanisms over transition metal catalysts. Applied Catalysis A: General 346 (1-2): 1-27, Aug. 2008.
European search report and search opinion dated Jan. 20, 2016 for EP Application No. 13817389.3.
Extended European search report and opinion dated Jul. 19, 2017 for EP Application No. 15734911.9.
Fallah, et al., A New Nano-(2Li2O/MgO) Catalyst/Porous Alpha-Alumina Composite for the Oxidative Coupling of Methane Reaction, AIChE Journal, Mar. 2010, 56(3):717-28.
Gao, et al. A study on methanol steam reforming to CO2 and H2 over the La2 CO4 nanofiber catalyst. Journal of Solid State Chemistry 181: 7-13, 2008.
Gao, et al. The direct decomposition of NO over the La2 CuO4 nanofiber catalyst. Journal of Solid State Chemistry 181: 2804-2807, 2008.
Ghosh, et al., Absorption of carbon dioxide into aqueous potassium carbonate promoted by boric acid, Energy Procedia, Feb. 2009, pp. 1075-1081.
Graves, C.R. Recycling CO2 into Sustainable Hydrocarbon Fuels: Electrolysis of CO2 and H2O. Dissertation, Columbia University (2010).
Guo, et al. Current Status and Some Perspectives of Rare Earth Catalytic Materials. Journal of the Chinese Rare Earth Society 25(1): 1-15, Feb. 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4(4):128-131.
Hosseinpour, Performance of CaX Zeolite for Separation of C2H6, C2H4, and CH4 by Adsorption Process; Capacity, Selectivity, and Dynamic Adsorption Measurements, Separation Science and Technology, 2011, 46:349-355 . . . .
Huang, et al. Exploiting shape effects of La2O3 nanocrystals for oxidative coupling of methane reaction. Nanoscale—Electronic Supplementary Material, 2013, 7 pages.
Huang, et al. Exploiting shape effects of La2 O3 nanocrystals for oxidative coupling of methane reaction. Nanoscale 5(22): 10844-10848, 2013.
International preliminary report on patentability dated Jul. 21, 2016 for PCT Application No. US2015/010688.
International search report and written opinion dated Mar. 6, 2014 for PCT/US2013/042480.
International search report and written opinion dated Mar. 17, 2014 for PCT Application No. US2013/021312.
International search report and written opinion dated Jun. 12, 2015 for PCT Application No. US2015/010688.
International search report and written opinion dated Aug. 11, 2016 for PCT/US2016/024195.
International search report and written opinion dated Aug. 16, 2017 for PCT Application US-2017027483.
International search report and written opinion dated Aug. 18, 2016 for PCT/US2016/022891.
International search report and written opinion dated Sep. 5, 2017 for PCT Application US-2017025544.
International search report and written opinion dated Nov. 1, 2013 for PCT/US2013/049742.
International search report and written opinion dated Nov. 11, 2015 for PCT Application No. US2014/067465.
International search report and written opinion dated Feb. 2, 2017 for PCT Application No. US-2016052959.
International search report dated Mar. 19, 2014 for PCT Application No. US2013/073657.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, et al. Synthesis of Ethylene via Oxidative Coupling of Methane. Journal of Catalysis 73: 9-19, 1982.
Keller, Gas-Adsorption Processes: State of the Art, American Chemical Society, 1983, pp. 145-169 . . . .
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Labinger. Oxidative coupling of methane: an inherent limit to selectivity? Catal. Lett. 1988; 1:371-376.
Li, B. et al. Advances in CO2 capture technology: A patent review. Applied Energy (2013) 102:1439-1447.
Li, et al. Combined Single-Pass Conversion of Methane Via Oxidative Coupling and Dehydroaromatization. Catalysis Letters, Sep. 2003, vol. 89, Issue 3-4, pp. 275-279.
Li, et al. Energy and Fuels. 2008, 22: 1897-1901.
Ling, et al. Preparation of Ag core—A Ushell Nanowires and Their Surface Enhanced Raman Spectroscopic Studies. Acta Chimica Sinica. 65 (9): 779-784, 2007.
Liu, et al. A novel Na2 WO4-Mn.SiC monolithic foam catalyst with improved thermal properties for the oxidative coupling of methane. Catalysis Communications 9: 1302-1306, 2008.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands . . . .
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.
Natural Gas Spec Sheet, 2003, prepared by Florida Power and Light Company. 0.
Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Niu, et al. Preparation and characterization of La2 O3CO3 nanowires with high surface areas. Jounral of the Chinese Rare Earth Society 23 (Spec. Issue): 33-36, Dec. 2005.
Notice of allowance dated Sep. 9, 2016 for U.S. Appl. No. 15/076,480.
Notice of allowance dated Oct. 6, 2016 for U.S. Appl. No. 15/076,480.
Notice of allowance dated Jan. 4, 2016 for U.S. Appl. No. 14/789,953 . . . .
Notice of allowance dated Jan. 10, 2017 for U.S. Appl. No. 15/076,480.
Notice of allowance dated Jan. 13, 2016 for U.S. Appl. No. 14/789,946 . . . .
Notice of allowance dated Mar. 15, 2017 for U.S. Appl. No. 13/936,783.
Notice of allowance dated Apr. 27, 2016 for U.S. Appl. No. 13/900,898.
Notice of allowance dated May 16, 2017 for U.S. Appl. No. 14/592,668.
Notice of allowance dated Jun. 8, 2015 for U.S. Appl. No. 13/739,954.

(56) References Cited

OTHER PUBLICATIONS

Notice of allowance dated Aug. 9, 2016 for U.S. Appl. No. 15/076,480.
Notice of allowance dated Aug. 10, 2017 for U.S. Appl. No. 15/341,551.
Notice of allowance dated Aug. 11, 2016 for U.S. Appl. No. 13/900,898.
Notice of allowance dated Aug. 22, 2016 for U.S. Appl. No. 14/820,460.
Notice of Allowance dated Sep. 21, 2017 for U.S. Appl. No. 15/341,551.
Notice of allowance dated Sep. 22, 2016 for U.S. Appl. No. 13/936,870.
Notice of allowance dated Oct. 24, 2016 for U.S. Appl. No. 14/789,901.
Notice of allowance dated Dec. 5, 2016 for U.S. Appl. No. 15/076,480.
Nyce, et al. PCT/US2015/010525 filed Jan. 7, 2015 for "Ethylene-to-Liquids Systems and Methods".
Office action dated Jan. 14, 2016 for U.S. Appl. No. 13/936,870 . . . .
Office Action dated Jan. 25, 2018 for U.S. Appl. No. 15/354,886.
Office action dated Mar. 6, 2017 for U.S. Appl. No. 13/936,870.
Office action dated Mar. 16, 2016 for U.S. Appl. No. 14/789,901.
Office action dated Apr. 22, 2016 for U.S. Appl. No. 15/076.480.
Office action dated May 20, 2016 for U.S. Appl. No. 14/820,460.
Office action dated Jul. 21, 2017 for U.S. Appl. No. 15/076,402.
Office action dated Jul. 29, 2016 for U.S. Appl. No. 14/789,901.
Office action dated Sep. 6, 2017 for U.S. Appl. No. 13/936,870.
Office action dated Sep. 11, 2015 for U.S. Appl. No. 14/789,946.
Office action dated Sep. 11, 2015 for U.S. Appl. No. 14/789,953.
Office action dated Oct. 4, 2016 for U.S. Appl. No. 15/076,402 . . . .
Office action dated Oct. 23, 2014 for U.S. Appl. No. 13/739,954.
Office Action dated Oct. 27, 2017 for U.S. Appl. No. 14/553,795.
Office action dated Nov. 2, 2015 for U.S. Appl. No. 14/789,901.
Office Action dated Nov. 6, 2017 for U.S. Appl. No. 14/868,911.
Office action dated Nov. 7, 2016 for U.S. Appl. No. 13/936,783.
Office action dated Nov. 13, 2015 for U.S. Appl. No. 13/900,898.
Office Action dated Nov. 30, 2017 for U.S. Appl. No. 15/272,205.
Office action dated Dec. 23, 2015 for U.S. Appl. No. 13/936,783 . . . .
Office action dated Dec. 23, 2016 for U.S. Appl. No. 14/592,668.
Office action dated Jan. 26, 2017 for U.S. Appl. No. 15/341,551.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009 . . . .
Olah, G. Hydrocarbon Chemistry. 2nd Edition, John Wiley & Sons, 2003.
Pak, et al. Elementary Reactions in the Oxidative Coupling of Methane over Mn/Na2 WO4/SiO2 and Mn/Na2 WO4/MgO Catalysts. Journal of Catalysis 179:222-230, 1998.
Lunsford, et al. The oxidative coupling of methane on chlorinated Lithium-doped magnesium oxide. J. Chem. Soc., Chem. Commun., 1991, 1430-1432.
Qiu, et al. Steady-state conversion of methane to aromatics in high yields using an integrated recycle reaction system. Catalysis Letters 48: 11-15, 1997.
Rafique, et al. PCT/US2015/010688 filed Jan. 8, 2015 for "Oxidative Coupling of Methane Implementations for Olefin Production".
Rousseau, Handbook of Separation Process Technology, 1987, p. 682 . . . .
Saito, et al. Dehydrogenation of Propane Over a Silica-Supported Gallium Oxide Catalyst. Catalysis Letters, Sep. 2003, vol. 89, Issue 3-4, pp. 213-217. 0.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK-Conference, Hamburg, Germany (2007).
Sheridan, D. et al. PCT/US2014/067465 filed Nov. 25, 2014 for "Integrated Mixers and Heat Exchangers for Oxidative Coupling Methane Systems".
Simons, K. Membrane Technologies for CO2 Capture. Dissertation, U. of Twente (2010).
Smith, et al. Recent developments in solvent absorption technologies at the CO2CRC in Australia. Energy Procedia 1(2009): 1549-1555.
Somorjai, et al. High technology catalysts towards 100% selectivity Fabrication, characterization and reaction studies. Catalysis today 100:201-215, 2005.
Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Takanabe, et al. Mechanistic Aspects and Reaction Pathways for Oxidative Coupling of Methane on Mn/Na2WO4/SiO2 Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by Mn/Na2 WO4/SiO2 . Angewandte Chemie International Edition 47:7689-7693, 2008.
Tong, et al. Development strategy research of downstream products of ethene in Tianjin. Tianjin Economy, pp. 37-40, 1996.
Trautmann, et al. Cryogenic technology for nitrogen rejection from variable content natural gas. Presented at the XIV Convencion Internacional de Gas, Caracas, Venezuela, May 10-12, 2000, 13 pages.
Supplementary European search report dated Jun. 27, 2017 for EP Application No. 14866399.
U.S. Appl. No. 13/936,870 Notice of Allowance dated Mar. 21, 2018.
U.S. Appl. No. 62/050,729, filed Sep. 15, 2014.
U.S. Appl. No. 62/073,478, filed Oct. 31, 2014.
U.S. Appl. No. 15/888,777 Office Action dated Apr. 26, 2018.
U.S. Appl. No. 14/553,795 Notice of Allowance dated May 25, 2018.
U.S. Appl. No. 14/868,911 Office Action dated May 29, 2018.
U.S. Appl. No. 15/076,402 Office Action dated Mar. 8, 2018.
U.S. Appl. No. 15/356,202 Office Action dated Apr. 26, 2018.
U.S. Appl. No. 15/476,889 Office Action dated Apr. 30, 2018.
U.S. Appl. No. 15/487,181 Corrected Notice of Allowability dated Mar. 1, 2018.
U.S. Appl. No. 15/487,181 Notice of Allowability dated Feb. 13, 2018.
U.S. Appl. No. 15/487,181 Notice of Allowance dated Jan. 30, 2018.
U.S. Appl. No. 15/487,181 Supplemental Notice of Allowability dated Feb. 7, 2018.
Wang, et al. Autothermal oxidative coupling of methane on the SrCO3/Sm2 O3 catalysts. Catalysis communications 10: 807-810, 2009.
Wang, et al. Comparative study on oxidation of methane to ethane and ethylene over Na2 WO4-Mn/SiO2 catalysts prepared by different methods. Journal of Molecular Catalysis A: Chemical 245:272-277, 2006.
Wang, et al., Critical Influence of BaCO3 on Low Temperature Catalytic Activity of BaCO3/Zr02 Catalysts for Oxidative Coupling of Methane, Catalysis Letters (2009), 129:156-162.
Wang, et al. Low temperature selective oxidation of methane to ethane and ethylene over BaCO3/La2 O3 catalysts prepared by urea combustion method. Catalysis communications 7: 5963, 2006.
Water Electrolysis & Renewable Energy Systems. FuelCellToday (May 2013).
Wikipedia search, Adiabatic Process, Mar. 2011, 10 pages.
Witek-Krowiak, A. et al. Carbon Dioxide Removal in a Membrane Contactor-Selection of Absorptive Liquid/Membrane System. Intl J Chem Eng and Appl. (2012) 3(6):391-395.
Wong, et al. Oxidative coupling of methane over alkali metal oxide promoted La2 O3/BaCO3 cataylsts. J. Chem. Tech. Biotechnol. 65:351-354, 1996.

(56) References Cited

OTHER PUBLICATIONS

Xu, et al. Maximise ethylene gain and acetylene selective hydrogenation efficiency. Petroleum technology quarterly 18.3 (2013): 39-42.
Xu, G. et al. An Improved CO2 Separation and Purification System Based on Cryogenic Separation and Distillation Theory. Energies (2014) 7:3484-3502.
Yan, D. Modeling and Application of a Thermoelectric Generator. Thesis, Univ. Toronto (2011).
Yang, et al. Anistropic synthesis of boat shaped core shell Au—Ag nanocrystals and nanowires. Nanotechnology 17: 2304-2310, 2006.
Yu, et al. Oxidative coupling of methane over acceptor-doped SrTiO3: Correlation between p-type conductivity and C2 selectivity and C2 yield. Journal of Catalysis. 13 (5): 338-344, 1992.
Zhang, Q. Journal of Natural Gas Chem., 12:81, 2003.
Zhao, et al. Technologies and catalysts for catalytic preparation of ethene. Industrial catalysis 12 (Supplement): 285-289, 2004.
Zhou. BP-UOP Cyclar Process. Handbook of Petroleum Refining Processes, The McGraw-Hill Companies (2004), pp. 2.29-2.38.
Zhou, et al. Functionalization of lanthanum hydroxide nanowires by atom transfer radical polymerization. Nanotechnology 18, 2007, 7 pages.
Zimmerman, et al. Ethylene. Ulmann's Encyclopedia of Inudstrial Chemisty, Wiley-VCH Verlag GmbH & Co. KGaA, Weinheim, Germany, 2009, 66 pages.
Co-pending U.S. Appl. No. 15/581,996, filed Apr. 28, 2017.
Iwamoto, M. One step formation of propene from ethene or ethanol through metathesis on nickel ion-loaded silica. Molecules. Sep. 13, 2011;16(9):7844-63.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.
Process Systems; "Steam Tables" Apr. 8, 2017—https://web.archive.org/web/20170408152403/https://valvesonline.com.au/references/steam-tables/.
Ahari, et al. Effects of operating parameters on oxidative coupling of methane over Na—W—Mn/SiO2 catalyst at elevated pressures. Journal of Natural Gas Chemistry. vol. 20, Issue 2, Mar. 2011, pp. 204-213.
PCT/US2018/041322 International Search Report and Written Opinion dated Sep. 24, 2018.
PCT/US2018/34184 International Search Report and Written Opinion dated Sep. 26, 2018.
U.S. Appl. No. 15/272,205 Office Action dated Sep. 25, 2018.
U.S. Appl. No. 15/354,886 Office Action dated Aug. 31, 2018.
U.S. Appl. No. 16/021,441 Office Action dated Aug. 28, 2018.
Caskey, et al., Dramatic Tuning of Carbon Dioxide Uptake via Metal Substitution in a Coordination Polymer with Cylindrical Pores, J. Am. Chem. Soc., (2009), 130(33): 10870-71.
Corma, From Microporous to Mesoporous Molecular Sieve Materials and Their Use in Catalysis, Chern. Rev., 97, 1997, pp. 2373-2419.
Dietzel, et al., Adsorption properties and structure of CO2 adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009) 18:156-160.
Geier, et al., Selective adsorption of ethylene over ethane and propylene over propane in the metal-organic frameworks M2(dobdc) (M = Mg, Mn, Fe, Co, Ni, Zn), Chem. Sci., 2013, 4:2054-2061.
Godini, et al. Techno-economic analysis of integrating the methane oxidative coupling and methane reforming processes. Fuel processing technology 2013 vol. 106 pp. 684-694.
Goto et al, Mesoporous Material from Zeolite, Journal of Poruous Materials, 2002, pp. 43-48.
Haag, W.O. et al. Aromatics, Light Olefins and Gasoline from Methanol: Mechanistic Pathways with ZSM-5 Zeolite Catalyst. J Mol Catalysis (1982) 17:161-169.
Liu, et al. Increasing the Density of Adsorbed Hydrogen with Coordinatively Unsaturated Metal Centers in Metal-Organic Frameworks Langmuir, 2008, 24:4772-77.
Makal, et al., Methane storage in advanced porous materials, Critical Review, Chem. Soc. Rev., 2012, 41 :7761-7779.
Mokhatab et al. "Handbook of Natural Gas Transmission and Processing: Principles and Practices" 2015. Chapter 1, pp. 237-242. (Year 2015).
Morgan, C.R. et al. Gasoline from Alcohols. Ind Eng Chem Prod Res Dev(1981) 20:185-190.
Ogura et al. Formation of Uniform Mesopores in ZSM-5 Zeolite through Treatment in Alkaline Solution, Chemistry Letters, 2000, pp. 882-883.
Olefins Conversion Technology, Website Accessed Aug. 28, 2014, http:www.CBI.com.
Tabak, S.A. et al. Conversion of Methanol over ZSM-5 to Fuels and Chemicals. Cat Today (1990) 307-327.
Wu, et al., High-Capacity Methane Storage in Metal-Organic Frameworks M2(dhtp): The Important Role of Open Metal Sites, J. Am. Chem. Soc. 131 (13):4995-5000.
Zhou, et al., Enhanced H2 Adsorption in Isostructural Metal-Organic Frameworks with Open Metal Sites: Strong Dependence of the Binding Strength on Metal Ions, J. Am. Chem. Soc., 2008, 130(46):15268-69.

\* cited by examiner

SYSTEMS AND METHODS FOR THE OXIDATIVE COUPLING OF METHANE

CROSS-REFERENCE

This application claims the benefit of U.S. Provisional Patent Application Ser. No. 62/529,942, filed Jul. 7, 2017, U.S. Provisional Patent Application Ser. No. 62/530,639, filed Jul. 10, 2017, and U.S. Provisional Patent Application Ser. No. 62/557,597, filed Sep. 12, 2017, each of which is entirely incorporated herein by reference for all purposes.

BACKGROUND

Olefins are an important product within the petrochemical industry. In order to produce olefins, various processes can be used. Some of these processes may include cracking of naphtha, cracking of ethane or propane, and oxidative coupling of methane. The oxidative coupling of methane (OCM) process is a way to generate olefins, including ethylene and propylene, from methane. The OCM process may utilize an OCM catalyst that is held within an OCM reactor. Methane and oxygen may flow through the OCM reactor to produce higher hydrocarbon products.

SUMMARY

Recognized herein is the need for novel and more efficient reactors, processes, and methods for producing olefins from methane. The present disclosure describes methods and systems for conducting an oxidative coupling of methane (OCM) process by controlling various parameters associated with the OCM reactor. In some aspects of the present disclosure, incorporation of the OCM methods within an integrated process is provided.

The high temperature requirements, fast kinetics, and highly exothermic nature of the oxidative coupling of methane reaction may cause it to be a difficult reaction to control. In order to improve the process, it may be desirable to control some process variables.

The process variables may include the temperature/pressure of the OCM reactor effluent gas, conversion of methane and selectivity for olefin. Some or all of these parameters may be connected, however with the proper reactor and process design, they can be controlled and optimized. By utilizing a reactor that comprises substantially adiabatic and non-adiabatic sections, many benefits can be achieved. Additionally, special control over feed injection (including such as gas velocity and contact time) can award superior reactor and process performance.

For a packed bed that is substantially adiabatic, the temperature profile of the process gas through the bed may be determined primarily by the relative concentrations of the feed gases and the inherent thermodynamics of the oxidative coupling of methane. However, using a staged system that comprises at least one substantially adiabatic section and at least one non-adiabatic section may add another dimension of control. By removing heat from the reaction at some points within the reactor, and allowing the reaction enthalpy to heat the process gas in others, a high level of control over the temperature profile of the reactor can be achieved.

The section or sections of the reactor that are substantially adiabatic may be insulated, or may be in thermal isolation from a heat transfer medium, while the non-adiabatic section or sections may be in thermal communication with a heat transfer medium. The use of a heat transfer medium may enable both an improved control over the temperature profile of the bed as well as heat integration in the process. The hot heat transfer medium may be used to preheat the feed streams, heat process gas in another location in a plant, or to generate electricity in a heat engine. The heat transfer medium may be water, or it may be a liquid with a high heat capacity, such as a molten salt.

Control of the location of feed component injection may be another way to manipulate the process variables. If a reactor comprises a number of tubes, then smaller concentric tubes of variable length can be used to add reactants in through the length of the reactor tube. A diffuser tube, comprising a tube with perforations that allow gas to escape downward along the tube length, can be an effective way to control the injection of various components. Components including methane, ethane, and oxygen can be injected into the reactor tube using diffuser tubes.

An aspect of the present disclosure provides a method for producing an olefin, the method comprising: (a) injecting a feed stream comprising oxygen ($O_2$) and methane ($CH_4$) into a non-adiabatic section of a reactor, which non-adiabatic section is in thermal communication with a heat transfer medium and comprises an oxidative coupling of methane (OCM) catalyst that facilitates an OCM reaction, wherein a maximum temperature within the non-adiabatic section is less than about 1,000° C. and heat generated from the OCM reaction is at least partially transferred to the heat transfer medium to produce an intermediate gas stream that contains at least about 1 mol % of the $O_2$; and (b) injecting the intermediate gas stream into a substantially adiabatic section of the reactor, wherein at least one of (i) a difference between a time when the intermediate gas stream exits the non-adiabatic section and a time when the intermediate gas enters the substantially adiabatic section is less than about 50 milliseconds (ms), (ii) an effluent gas at an outlet of the substantially adiabatic section contains less than about 500 parts per million (ppm) $O_2$, and (iii) a temperature at the outlet of the substantially adiabatic section is at least about 880° C., is satisfied.

In some embodiments, at least two of the (i)-(iii) are satisfied. In some embodiments, all three of the (i)-(iii) are satisfied. In some embodiments, the method further comprises: (i) injecting an oxygen stream containing oxygen ($O_2$) and a methane stream containing methane ($CH_4$) into a mixer at a temperature of less than about 450° C. and a pressure less than about 10 bar(gauge, "g") to produce a mixed gas stream; and (ii) increasing a temperature of the mixed gas stream to at least about 450° C. by putting the mixed gas stream into thermal communication with the heat transfer medium to produce the feed stream. In some embodiments, the method further comprises preheating a stream containing methane to a temperature of at least about 500° C. to produce a preheated methane stream. In some embodiments, the method further comprises mixing the preheated methane stream with a stream containing $O_2$ to produce a mixture having a temperature that is less than about 600° C. In some embodiments, a temperature of the stream containing $O_2$ is less than about 200° C. In some embodiments, the method further comprises flowing the mixture over an OCM catalyst to produce the feed stream. In some embodiments, the method further comprises flowing the mixture over an inert packing to produce the feed stream. In some embodiments, the inert packing comprises alumina ($Al_2O_3$), silica ($SiO_2$), $Fe_2O_3$, MgO, $Na_2O$, or another metal oxide. In some embodiments, the heat transfer medium is a molten salt. In some embodiments, the molten salt is used to increase the temperature of the mixed gas stream. In some embodiments, a temperature of the molten salt, when in thermal communication with the mixed gas stream, is at least about 500° C. In some embodiments, the molten salt flows countercurrent to the mixed gas stream in the non-adiabatic section. In some embodiments, the heat transfer medium is liquid water. In some embodiments, the liquid water is at a temperature of at least about 150° C. In some embodiments, the heat transfer medium is steam. In some embodiments, the method further comprises injecting ethane into the reactor. In some embodiments, a stream containing the ethane is injected into the reactor downstream of where the oxygen and methane are injected. In some embodiments, the stream containing the ethane is injected using a diffuser tube. In some embodiments, the ethane is injected into the substantially adiabatic section of the reactor. In some embodiments, the method further comprises injecting propane into the reactor. In some embodiments, the propane is injected into the substantially adiabatic section of the reactor. In some embodiments, the method further comprises injecting an effluent of the non-adiabatic section into a post bed cracking unit. In some embodiments, the post bed cracking unit does not contain an OCM catalyst. In some embodiments, the post bed cracking unit converts ethane to ethylene. In some embodiments, the method further comprises injecting an additional stream comprising ethane into the post bed cracking unit. In some embodiments, the $O_2$ is injected downstream of where the methane is injected. In some embodiments, the $O_2$ is injected using a diffuser tube. In some embodiments, the $O_2$ and ethane are injected into the non-adiabatic section of the reactor downstream of where the methane is injected. In some embodiments, the $O_2$ and the ethane are injected using concentric diffuser tubes. In some embodiments, the method further comprises transferring heat from the heat transfer medium to a steam superheater to produce a stream containing superheated steam. In some embodiments, the steam superheater raises a temperature of steam. In some embodiments, a steam enters the steam superheater at a temperature of at least about 150° C. In some embodiments, the steam exiting the steam superheater has a temperature of at least about 400° C. In some embodiments, the method further comprises injecting the stream containing superheated steam into a unit that produces electricity. In some embodiments, the unit is a steam turbine. In some embodiments, the non-adiabatic section comprises at least about 10 tubes. In some embodiments, a pressure drop across each tube is less than about 3 bar(g). In some embodiments, each tube has a diameter that is greater than about 0.75 inches and less than about 2.25 inches. In some embodiments, each tube has a length that is greater than about 4 feet and less than about 12 feet. In some embodiments, a gas velocity in each tube is greater than about 3 meters per second (m/s) and less than about 10 meters per second (m/s). In some embodiments, a pressure of the gas in each tube is greater than about 4 bar(g) and less than about 10 bar(g).

Another aspect of the present disclosure provides a method for producing ethylene, the method comprising: (a) injecting an oxygen stream containing oxygen ($O_2$), a methane stream containing methane ($CH_4$), and a diluent stream containing water ($H_2O$), carbon dioxide ($CO_2$), or combinations thereof, into a reactor containing an oxidative coupling of methane (OCM) catalyst to produce an OCM effluent gas containing a diluent, wherein at least one of (i) at least about 20 mol % of the gas injected into the reactor is from the diluent stream, (ii) a methane conversion is at least about 10%, and (iii) an outlet temperature of the reactor is at least about 800° C., is satisfied; and (b) injecting the OCM effluent gas and an ethane stream containing ethane into a post bed cracking (PBC) unit, wherein the PBC unit converts ethane comprised in the OCM effluent gas and the ethane stream to ethylene, thereby generating a PBC effluent stream having an ethylene-to-ethane ratio greater than about 3:1.

In some embodiments, at least two of the (i)-(iii) are satisfied. In some embodiments, all three of the (i)-(iii) are satisfied. In some embodiments, the method further comprises producing a steam by putting water in thermal communication with the gas within the reactor. In some embodiments, the method further comprises injecting the steam into the reactor. In some embodiments, the steam produced is the same as the diluent stream. In some embodiments, the oxygen stream is pre-mixed with the diluent stream to produce a diluted $O_2$ stream. In some embodiments, the diluted $O_2$ stream is injected into the reactor downstream of where the methane stream is injected. In some embodiments, the diluted $O_2$ stream is injected using a diffuser tube. In some embodiments, the method further comprises injecting a stream containing ethane into the reactor. In some embodiments, the stream containing ethane is injected downstream of the methane stream. In some embodiments, the stream containing ethane is injected using a diffuser tube.

Another aspect of the present disclosure provides a method for producing an olefin, the method comprising: (a) injecting a stream containing methane ($CH_4$) and oxygen ($O_2$) into a non-adiabatic section of a reactor, which non-adiabatic section is in thermal communication with a heat transfer medium that contains an oxidative coupling of methane (OCM) catalyst to produce an intermediate gas stream, wherein the OCM catalyst undergoes deactivation over time, such that (i) an outlet temperature of the non-adiabatic section decreases over time, (ii) an oxygen concentration at an outlet of the non-adiabatic section increases over time, and (iii) the oxygen concentration at the outlet of the non-adiabatic section is at least about 500 parts per million (ppm); and (b) injecting the intermediate gas stream into a substantially adiabatic section of the reactor, wherein with the catalyst deactivation (i) an oxygen concentration at an inlet of the substantially adiabatic section increases over time, (ii) an outlet temperature of the substantially adiabatic section increases over time, and (iii) an oxygen concentration at an outlet of the substantially adiabatic section is less than about 50 parts per million (ppm).

In some embodiments, the OCM catalyst displays lower methane conversion over time with the deactivation. In some embodiments, a maximum temperature in the non-adiabatic section of the reactor decreases over time with the deactivation. In some embodiments, the method further comprises pre-mixing a methane stream and an oxygen stream to product the stream. In some embodiments, the outlet temperature of the substantially adiabatic section of the reactor is between 700-900° C. at any catalyst deactivation percentage.

Another aspect of the present disclosure provides an apparatus for producing ethylene, the apparatus comprising: (a) a first section that is configured to mix a methane stream containing methane ($CH_4$) and an oxygen stream containing oxygen ($O_2$) to generate a mixed stream of $CH_4$ and $O_2$; (b) a second section that is configured to heat the mixed stream to a temperature of at least about 400° C.; (c) a third section that comprises at least about 50 tubes, wherein a given tube of the at least about 50 tubes comprises at least two of (i) an oxidative coupling of methane (OCM) catalyst, (ii) an outer diameter greater than about 0.5 inches, (iii) a length of at least about 3 feet, and (iv) at least a portion that is in thermal communication with a heat transfer medium; and (d) a fourth section that that is downstream of and fluidically coupled to the third section, wherein the fourth section is substantially adiabatic.

In some embodiments, the apparatus further comprises a tube that injects the oxygen stream downstream of a location at which the methane stream is injected. In some embodiments, the tube is a diffuser tube. In some embodiments, the apparatus further comprises a fifth section for injecting ethane. In some embodiments, the fifth section is a tube that extends beyond the first section. In some embodiments, the fifth section is a diffuser tube. In some embodiments, there is substantially no air gap between the third section and the fourth section. In some embodiments, a maximum temperature of the third section is less than about 1,000° C. In some embodiments, a pressure drop in the given tube is less than about 3 bar(g). In some embodiments, the heat transfer medium is molten salt. In some embodiments, the heat transfer medium is a liquid. In some embodiments, the liquid comprises water. In some embodiments, an oxygen concentration at an exit of the fourth section is less than about 50 parts per million (ppm). In some embodiments, an oxygen concentration at an exit of the third section is at least about 500 ppm. In some embodiments, the given tube of the at least about 50 tubes comprises at least three of the (i)-(iv). In some embodiments, the given tube of the at least about 50 tubes comprises all of the (i)-(iv).

Another aspect of the present disclosure provides a method for producing an olefin, the method comprising: (a) providing a reactor having an isothermal section, which isothermal section contains a catalyst capable of promoting an oxidative coupling of methane (OCM) reaction and is in thermal communication with a heat transfer medium; and (b) introducing a gas mixture into the isothermal section of the reactor, which gas mixture comprises oxygen ($O_2$) and methane ($CH_4$), whereby at least about 75 mol % of the $O_2$ reacts with the $CH_4$ to produce an effluent stream comprising hydrocarbon compounds having two or more carbon atoms ($C_{2+}$ compounds) and non-$C_{2+}$ impurities.

In some embodiments, the OCM reaction has a selectivity for $C_{2+}$ compounds of at least about 50% at 700° C. In some embodiments, the OCM reaction has a selectivity for $C_{2+}$ compounds of at least about 60% at 750° C. In some embodiments, the OCM reaction has a selectivity for $C_{2+}$ compounds of at least about 65% at 800° C. In some embodiments, the gas mixture has a temperature between about 650° C. and about 750° C. In some embodiments, the effluent stream has temperature between about 800° C. and about 900° C. In some embodiments, the gas mixture contains between about 13 mol % and about 17 mol % $O_2$. In some embodiments, the effluent stream contains between about 0.5 mol % and about 3 mol % $O_2$. In some embodiments, between about 12 mol % and about 16 mol % of the $CH_4$ is converted to $C_{2+}$ compounds and non-$C_{2+}$ impurities in the isothermal section. In some embodiments, the catalyst is a perovskite or comprises a lanthanide element. In some embodiments, the catalyst does not shrink or sinter. In some embodiments, at least about 80 mol % of the $O_2$ reacts with the $CH_4$ to produce $C_{2+}$ compounds and non-$C_{2+}$ impurities. In some embodiments, the method further comprises: directing an additional gas mixture comprising methane ($CH_4$) and an oxidizing agent into a light-off section in fluid communication with and upstream of the isothermal section, which light-off section is in thermal communication with an additional heat transfer medium and contains an additional catalyst capable of promoting an additional OCM reaction; and converting at least a portion of the $CH_4$ and the oxidizing agent from the additional gas mixture in the additional OCM reaction to produce additional $C_{2+}$ compounds. In some embodiments, the heat transfer medium and the additional heat transfer medium are molten salts. In some embodiments, the additional OCM reaction has a selectivity for $C_{2+}$ compounds of at least about 30% at 550° C. In some embodiments, the additional OCM reaction has a selectivity for $C_{2+}$ compounds of at least about 40% at 600° C. In some embodiments, the reactor further comprises a heating section in fluid communication with and upstream of the light-off section, which heating section is in thermal communication with a further additional heat transfer medium, which further additional heat transfer medium comprises a molten salt. In some embodiments, the additional gas mixture has a temperature between about 450° C. and about 580° C. In some embodiments, the method further comprises generating an additional effluent stream comprising the additional $C_{2+}$ compounds, wherein the additional effluent stream has a temperature between about 650° C. and about 750° C. In some embodiments, the additional gas mixture contains between about 15 mol % and about 20 mol % $O_2$. In some embodiments, the method further comprises generating an additional effluent stream comprising the additional $C_{2+}$ compounds, wherein the additional effluent stream contains between about 13 mol % and about 17 mol % $O_2$. In some embodiments, between about 3 mol % and about 5 mol % of the $CH_4$ from the additional gas mixture is converted to $C_{2+}$ compounds and non-$C_{2+}$ impurities in the light-off section. In some embodiments, the additional catalyst comprises nanowires. In some embodiments, the additional catalyst is capable of performing oxidative dehydrogenation (ODH). In some embodiments, at least about 10 mol % the $O_2$ from the additional gas mixture reacts with the $CH_4$ to produce $C_{2+}$ compounds and non-$C_{2+}$ impurities. In some embodiments, the method further comprises: directing the effluent stream from the isothermal section into an adiabatic section in fluid communication with and downstream of the isothermal section, which adiabatic section is insulated and contains an additional catalyst capable of promoting an additional OCM reaction reacting at least a portion of the effluent stream in the additional OCM reaction to yield a product stream, which product stream has an oxygen concentration that is less than or equal to about 2,000 parts per million (ppm). In some embodiments, the additional OCM reaction has a net selectivity for $C_{2+}$ compounds of between about 0% and about 20% at 850° C. In some embodiments, the effluent stream comprises unreacted $CH_4$ and wherein less than about 10 mol % of unreacted $CH_4$ is reformed into CO and $H_2$. In some embodiments, the additional catalyst is a perovskite. In some embodiments, the additional catalyst facilities oxidative dehydrogenation (ODH). In some embodiments, the effluent stream comprises unreacted $CH_4$ and wherein between about 0 mol % and about 3 mol % of the unreacted $CH_4$ is converted to $C_{2+}$ compounds and non-$C_{2+}$ impurities in the adiabatic section. In some embodiments, the method further comprises adding between about 0 mol % and about 5 mol % ethane ($C_2H_6$) to the effluent stream near an inlet of the adiabatic section. In some embodiments, the effluent stream is introduced into the adiabatic section at a temperature between about 800° C. and about 900° C. In some embodiments, a product stream exits the adiabatic section at a temperature between about 850° C. and about 950° C. In some embodiments, the reactor further comprises a post-bed cracking (PBC) section in fluid communication with and downstream of the adiabatic section, which PBC section converts $C_2H_6$ into $C_2H_4$ using heat derived from the OCM reaction and/or the additional OCM reaction. In some embodiments, the method further comprises adding between about 1 mol % and about 5 mol % ethane ($C_2H_6$) to a PBC process stream near an inlet of the PBC section. In some embodiments, at least about 20 mol % of the $CH_4$ is converted to $C_{2+}$ compounds and non-$C_{2+}$ impurities in the combination of the light-off section, the isothermal section and the adiabatic section.

Another aspect of the present disclosure provides a system for performing oxidative coupling of methane (OCM), the system comprising a reactor comprising: (a) a light-off section that is adapted to accept a gas mixture comprising oxygen ($O_2$) and methane ($CH_4$) and contains a first OCM catalyst that facilies an OCM reaction which converts the $O_2$ and the $CH_4$ into hydrocarbon compounds having two or more carbon atoms ($C_{2+}$ compounds) at a selectivity of at least about 30% at 550° C., wherein the light-off section is in thermal communication with a first heat transfer medium; (b) an isothermal section in fluidic communication with and downstream of the light-off section, which isothermal section contains a second OCM catalyst that has a selectivity for $C_{2+}$ compounds of at least about 50% at 700° C., wherein the isothermal section is in thermal communication with a second heat transfer medium; and/or (c) an adiabatic section in fluidic communication with and downstream of the isothermal section, which adiabatic section contains a third OCM catalyst that has a net selectivity for $C_{2+}$ compounds of at least about 0% at 850° C.

In some embodiments, the reactor further comprises a post-bed cracking (PBC) section in fluid communication with and downstream of the adiabatic section, which PBC section converts $C_2H_6$ into $C_2H_4$ using heat derived from the OCM reaction. In some embodiments, the reactor comprises both the light-off section and the adiabatic section. In some embodiments, the reactor is adapted to operate at a pressure of greater than about 2 bar(g). In some embodiments, the reactor is a tubular reactor. In some embodiments, the first transfer medium and the second heat transfer medium are the same. In some embodiments, the first transfer medium and/or the second heat transfer medium are molten salts. In some embodiments, the system further comprises a methanation reactor that is in fluid communication with the first heat transfer medium or the second heat transfer medium. In some embodiments, the reactor further comprises a methanation section in fluidic communication with and upstream of the light-off section, which methanation section contains a methanation catalyst.

Another aspect of the present disclosure provides a method for producing an olefin, the method comprising producing a gas stream comprising methane ($CH_4$), oxygen ($O_2$), and a diluent and passing the gas stream over an oxidative coupling of methane (OCM) catalyst at a pressure of at least about 2 bar(g) to convert at least some of the $CH_4$ into hydrocarbon compounds having two or more carbon atoms ($C_{2+}$ compounds), wherein a ratio of diluent molecules to carbon atoms in the gas stream is at least about 0.1.

In some embodiments, the diluent comprises water ($H_2O$). In some embodiments, the diluent comprises carbon dioxide ($CO_2$). In some embodiments, the ratio is at least about 0.5. In some embodiments, the ratio is at most about 5. In some embodiments, the ratio is between about 0.1 and about 5. In some embodiments, the pressure is at least about 4 bar(g).

Another aspect of the present disclosure provides a method for producing an olefin, the method comprising: (a) injecting an oxidizing agent and a paraffin into a gas stream containing a radical transfer agent to provide a reaction mixture in a vessel, which reaction mixture is at a reaction temperature and at a reaction pressure sufficient to result in ignition of the reaction mixture; and (b) holding the reaction mixture in the vessel for a time period that is sufficient to permit the reaction mixture to convert to a product mixture, whereby the paraffin is converted to the olefin in the product mixture at an apparent selectivity of at least about 30%.

In some embodiments, the method further comprises, subsequent to (b), cooling the product mixture. In some embodiments, the method further comprises repeating (a)-(b) to produce additional olefins. In some embodiments, the time period held in (b) is the auto-ignition delay time (AIDT). In some embodiments, the time period held in (b) is sufficient to accumulate a critical concentration of radical species. In some embodiments, (i) the reaction mixture is converted to the product mixture in a first stage, (ii) at least a portion of the product mixture is directed to a second stage downstream of the first stage, and (ii) an additional oxidizing agent and paraffin are injected in the second stage. In some embodiments, (a)-(b) are performed at least two times. In some embodiments, upon ignition of the reaction mixture, the radical transfer agent is radicalized to yield a radicalized transfer agent. In some embodiments, the radicalized transfer agent radicalizes the paraffin to yield a radicalized paraffin, and wherein the radicalized paraffin oxidizes to form the olefin. In some embodiments, the radical transfer agent is methane, water, hydrogen, or any combinations thereof. In some embodiments, upon ignition of the reaction mixture, at least one of a hydroxyl radical (HO.), a methyl radical ($H_3C$.) and a hydrogen radical (H.) are produced. In some embodiments, the vessel contains a radicalization initiator. In some embodiments, the radicalization initiator is a solid catalyst. In some embodiments, the solid catalyst is an oxidative coupling of methane (OCM) catalyst. In some embodiments, the paraffin is ethane and the olefin is ethylene. In some embodiments, the paraffin is propane and the olefin is propylene. In some embodiments, the reaction temperature is at least about 450° C. In some embodiments, prior to cooling the product mixture, the product mixture has a temperature of less than about 850° C. In some embodiments, the reaction pressure is about 8 bar(g). In some embodiments, the apparent selectivity is at least about 85%. In some embodiments, the apparent selectivity is a molar fraction of olefin produced per parent alkane consumed, and wherein the parent alkane is an alkane with the same number of carbons as the olefin produced. In some embodiments, a portion of the paraffin is converted to CO, $CO_2$, or any combinations thereof ($CO_x$). In some embodiments, the paraffin is converted to the olefin at a carbon efficiency that is at least about 50%, and wherein the carbon efficiency is a percentage of olefin produced relative to $CO_x$ formed. In some embodiments, the AIDT is about 10 milliseconds (ms). In some embodiments, the oxidizing agent in the reaction mixture is less than about 1%. In some embodiments, a concentration of the paraffin in the reaction mixture is less than about 10 mol %. In some embodiments, the gas stream is an OCM effluent. In some embodiments, the gas stream is superheated steam. In some embodiments, the oxidizing agent is $O_2$. In some embodiments, the oxidizing agent, the paraffin and the radical transfer agent are different species.

Another aspect of the present disclosure provides a system for performing oxidative coupling of methane (OCM), comprising: an OCM reactor comprising an OCM catalyst that facilitates an OCM reaction, the OCM reactor configured to receive methane and an oxidizing agent and permit at least a portion of the methane and the oxidizing agent to react in the OCM reaction to yield an effluent stream; and an oxidative dehydrogenation (ODH) reactor downstream of and in fluidic communication with the OCM reactor, which ODH reactor receives at least a portion of the effluent stream from the OCM reactor, wherein the ODH reactor comprises an ODH catalyst that facilities an ODH reaction in which at least a portion of paraffins from the effluent stream is converted into olefins.

In some embodiments, the OCM reactor is a molten salt reactor. In some embodiments, the molten salt reactor is a tubular reactor. In some embodiments, the ODH catalyst comprises $Cr_2O_3$ supported on $SiO_2$, $Al_2O_3$, $TiO_2$ or $ZrO_2$, $Cr/SO_4$—$SiO_2$, K—$Cr/SO_4$—$SiO_2$, K—Cr—$Mn/SiO_2$, Cr/H—ZSM-5, Cr/Silicalite-2, Fe—Mn/Silicalite-2, Cr—Mn/Silicalite-2, Cr—Mn—Ni/Silicalite-2, $MnO_2$, K-doped $MnO_2$, $Na_2WO_4$—$Mn/SiO_2$, $CeO_2$, Fe—$Cr/ZrO_2$, or combinations thereof. In some embodiments, the paraffins comprise ethane and/or propane. In some embodiments, the olefins comprise ethylene and/or propylene.

Another aspect of the present disclosure provides a method for performing oxidative coupling of methane (OCM), the method comprising: directing methane and an oxidizing agent into an OCM reactor, wherein the OCM reactor comprises an OCM catalyst that facilitates an OCM reaction and is configured to permit at least a portion of the methane and the oxidizing agent to react in the OCM reaction to yield an effluent stream; and directing at least a portion of the effluent stream into an oxidative dehydrogenation (ODH) reactor downstream of and in fluidic communication with the OCM reactor, wherein the ODH reactor comprises an ODH catalyst that facilities an ODH reaction in which at least a portion of paraffins from the effluent stream is converted into olefins.

In some embodiments, the oxidizing agent is oxygen. In some embodiments, the effluent stream comprises unreacted oxidizing agent. In some embodiments, at least a portion of the unreacted oxidizing agent is used as an oxidant in the ODH reaction. In some embodiments, the effluent stream comprises carbon dioxide ($CO_2$). In some embodiments, at least a portion of the $CO_2$ is used as an oxidant in the ODH reaction. In some embodiments, the method further comprises converting the at least the portion of the $CO_2$ to carbon monoxide (CO) in the ODH reaction. In some embodiments, the method further comprises directing at least a portion of the CO into a methanation reactor to generate a methanation product stream comprising methane. In some embodiments, the method further comprises directing at least a portion of the methanation product stream into the OCM reactor.

Another aspect of the present disclosure provides a system for performing a catalytic reaction comprising: a reactor comprising a catalyst bed, the catalyst bed comprising a void material having a void fraction of greater than or equal to about 70% and a catalytic material that facilitates the catalytic reaction.

In some embodiments, the void fraction is greater than or equal to about 85%. In some embodiments, the void material and the catalytic material is pre-assembled prior to being loaded into the reactor. In some embodiments, catalytic material is deposited as a film onto a surface of the void material. In some embodiments, the reactor comprises a liner in contact with an inner surface of the reactor. In some embodiments, the liner is a flexible metal foil. In some embodiments, the void material and the catalytic material are deposited onto the liner.

Another aspect of the present disclosure provides a method for producing higher hydrocarbon compounds, the method comprising: directing a feed stream comprising ethylene into a separations unit comprising a pressure swing adsorption (PSA) unit and/or a temperature swing adsorption (TSA) unit to adsorb at least a portion of the ethylene from the feed stream at a first pressure and/or a first temperature; and adjusting the first pressure and/or the first temperature of the separations unit to a second pressure and/or a second temperature to (i) desorb at least a portion of the at least the portion of the ethylene and (ii) convert at least an additional portion of the at least the portion of the ethylene to the higher hydrocarbon compounds in an ethylene conversion reaction.

In some embodiments, the second pressure is lower than the first pressure. In some embodiments, the second temperature is higher than the first temperature. In some embodiments, the first temperature is less than or equal to about 50° C. In some embodiments, the first pressure is greater than or equal to about 6 bar(a). In some embodiments, the second temperature is greater than or equal to about 100° C. In some embodiments, the second pressure is less than or equal to about 5 bar(a). In some embodiments, the feed stream is an oxidative coupling of methane (OCM) effluent stream. In some embodiments, the method further comprises directing methane and an oxidizing agent into an OCM reactor to producing the OCM effluent stream. In some embodiments, the ethylene conversion reaction comprises a dimerization reaction and/or an oligomerization reaction. In some embodiments, the higher hydrocarbon compounds comprise butene. In some embodiments, the method further comprises directing a separations effluent stream comprising the higher hydrocarbon compounds from the separations unit into a metathesis unit to yield a product stream comprising propylene. In some embodiments, the separations unit comprises a material that facilitates ethylene selective adsorption and the ethylene conversion reaction. In some embodiments, the material is an adsorbent and/or catalyst. In some embodiments, the material comprises porous zeolites. In some embodiments, the porous zeolites have an average pore diameter between about 4 Å and about 8 Å. In some embodiments, the materials comprise zeolites doped with transition metals. In some embodiments, the zeolites comprise Fe-ZSM-5, ZSM-5, ZSM-23 or combinations thereof.

Another aspect of the present disclosure provides a system for performing oxidative coupling of methane (OCM), the system comprising: an OCM reactor comprising at least one corrugated metal foil and a catalyst that facilitates an OCM reaction, wherein the at least one corrugated metal foil comprising ridges and intervening grooves between the ridges and wherein the catalyst is disposed within the intervening grooves.

In some embodiments, the OCM reactor comprises a plurality of corrugated metal foils. In some embodiments, each of the plurality of corrugated metal foils comprises perforations that create passageways among the plurality of corrugated metal foils. In some embodiments, the at least one corrugated metal foil comprises an active zone. In some embodiments, the OCM reaction in conducted in the active zone. In some embodiments, the grooves are micro-channels.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

Figure 1A:
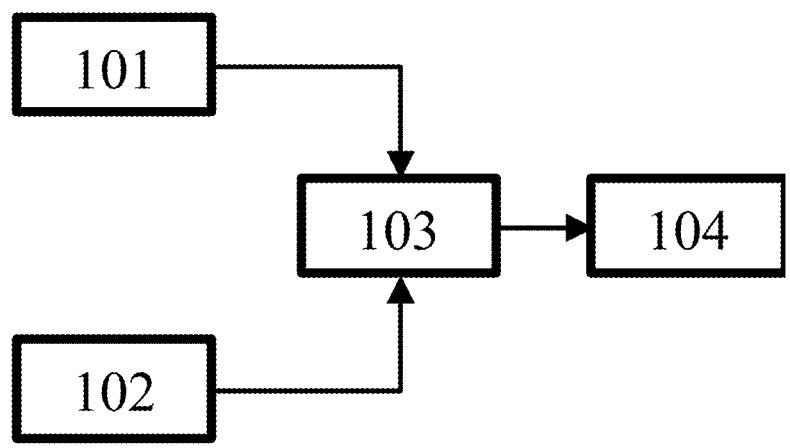
FIG. 1A shows an oxidative coupling of methane (OCM) system that comprises an adiabatic section and a non-adiabatic section.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term, "adiabatic" or "adiabatic process," generally refers to a process in which the pressure of a gas may be allowed to increase without substantial heat losses to the surroundings. A substantially adiabatic unit or element may permit little to no heat transfer between units or elements, such as, for example, less than 15%, 10%, 5%, 4%, 3%, 2%, or 1% heat transfer (e.g., as measured by total heat input and heat output from the unit).

The term "non-adiabatic," as used herein, generally refers to a unit or process element that may exchange heat with another unit or process element. Such unit or process element may be in thermal communication with a heat transfer unit (e.g., a heat exchanger or heat transfer medium).

The term "heat transfer medium," as used herein, generally refers to material (e.g., a solid or a liquid) that can be used to store thermal energy.

The terms "$C_{2+}$" and "$C_{2+}$ compound," as used herein, generally refer to a compound comprising two or more carbon atoms, e.g., two carbon atoms ($C_2$), three carbon atoms ($C_3$), etc. $C_{2+}$ compounds include, without limitation, alkanes, alkenes, alkynes and aromatics containing two or more carbon atoms. In some cases, $C_{2+}$ compounds include aldehydes, ketones, esters and carboxylic acids. Examples of $C_{2+}$ compounds include ethane, ethylene, acetylene, propane, propene, butane, butene, etc.

The term "non-$C_{2+}$ impurities," as used herein, generally refers to material that does not include $C_{2+}$ compounds. Examples of non-$C_{2+}$ impurities, which may be found in certain product streams (e.g., oxidative coupling of methane product stream), include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "light-off" as used herein, generally refers to initiation of an oxidative coupling of methane (OCM) reaction, for example at a low temperature, such as less than about 600° C., less than about 550° C., less than about 500° C., less than about 450° C., or less than about 400° C.

The term "radical transfer agent," as used herein, generally refers to a species of molecule that can undergo a transformation from its neutral form into a free radical under temperatures and pressures that species is exposed to in a process.

The term "auto-ignition delay time" (AIDT), as used herein, generally refers to the difference in time between when a fuel and oxidizer come into contact, in the absence of any external ignition source, and when the spontaneous combustion of the fuel and oxidizer mixture occurs.

The term "apparent selectivity," as used herein, generally refers to the fraction of the carbon of a selected species contained in the reactor effluent stream when compared to the amount of carbon contained in the reactor effluent stream excluding methane. For example, as an oxidative coupling of methane reactor feed stream may contain a number of hydrocarbon species beside methane, some of the desired products (e.g., ethylene) can be formed from multiple sources of methane, ethane and propane.

The term "net selectivity," as used herein, generally refers to a ratio of a desired product(s) formed (in moles of Carbon) to the sum of all products formed (desired and undesired) (in moles of Carbon) in a given process. The process can be a single-step or multi-step process. For example, a net selectivity for $C_{2+}$ compounds in an OCM process performed in an OCM system comprising a light off section, an isothermal section and an adiabatic section is determined as a ratio of ($C_{2+}$ compounds produced in the OCM system)/($C_{2+}$ and non-$C_{2+}$ compounds produced in the OCM system). As the feed mixture to the reactor may contain ethane and propane, this measurement may enable to evaluate the net generation of coupling products from OCM when in competition with higher alkane combustion and/or ODH.

The term "carbon efficiency," as used herein, generally refers to the extent to which an alkane is converted to an olefin relative to an oxidized compound (e.g. CO, $CO_2$, generally referred to as $CO_x$), and may be expressed as a percentage.

The term "unit," as used herein, generally refers to a unit operation, which is a basic operation in a process. Unit operations may involve a physical change or chemical transformation, such as, for example, separation, crystallization, evaporation, filtration, polymerization, isomerization, transformation, and other reactions. A given process may require one or a plurality of unit operations to obtain the desired product(s) from a starting material(s), or feedstock(s).

The term "paraffin," as used herein, generally refers to a saturated hydrocarbon. A paraffin may be an alkane having the formula $C_nH_{2n+2}$, wherein 'n' is an integer greater than or equal to 1.

In an OCM process, methane ($CH_4$) reacts with an oxidizing agent over a catalyst bed to generate $C_{2+}$ compounds. For example, methane can react with oxygen over a suitable catalyst to generate ethylene, e.g., $2\ CH_4+O_2 \rightarrow C_2H_4+2\ H_2O$ (See, e.g., Zhang, Q., *Journal of Natural Gas Chem.*, 12:81, 2003; Olah, G. "Hydrocarbon Chemistry," Ed. 2, John Wiley & Sons (2003)). This reaction may be exothermic ($\Delta H$=−67 kcals/mole) and may have been shown to occur at very high temperatures (e.g., >450° C. or >700° C.). Non-selective reactions that can occur include (a) $CH_4+2O_2 \rightarrow CO_2+2\ H_2O$ and (b) $CH_4+\frac{1}{2}\ O_2 \rightarrow CO+2\ H_2$. These non-selective reactions may also be exothermic, with reaction heats of −891 kJ/mol and −36 kJ/mol respectively. The conversion of methane to COx products may be undesirable due to both heat management and carbon efficiency concerns.

Experimental evidence suggests that free radical chemistry may be involved. (Lunsford, *J. Chem. Soc., Chem. Comm.*, 1991; H. Lunsford, *Angew. Chem., Int. Ed. Engl.*, 34:970, 1995). In the reaction, methane ($CH_4$) is activated on the catalyst surface, forming methyl radicals which then couples in the gas phase to form ethane ($C_2H_6$), followed by dehydrogenation to ethylene ($C_2H_4$). The OCM reaction pathway can have a heterogeneous/homogeneous mechanism, which involves free radical chemistry. Experimental evidence has shown that an oxygen active site on the catalyst activates the methane, removes a single hydrogen atom and creates a methyl radical. Methyl radicals may react in the gas phase to produce ethane, which is either oxidative or non-oxidatively dehydrogenated to ethylene. The main reactions in this pathway can be as follows: (a) $CH_4+O^- \rightarrow CH_3^* + OH^-$; (b) $2\ CH_3^* \rightarrow C_2H_6$; (c) $C_2H_6+O^- \rightarrow C_2H_4+H_2O$. In some cases, to improve the reaction yield, ethane can be introduced downstream of the OCM catalyst bed and thermally dehydrogenated via the following reaction: $C_2H_6 \rightarrow C_2H_4+H_2$. This reaction can be endothermic ($\Delta H$=−144 kJ/mol), which can utilize the exothermic reaction heat produced during methane conversion. Combining these two reactions in one vessel can increase thermal efficiency while simplifying the process.

Several catalysts have shown activity for OCM, including various forms of iron oxide, $V_2O_5$, $MoO_3$, $Co_3O_4$, Pt—Rh, Li/$ZrO_2$, Ag—Au, Au/$Co_3O_4$, Co/Mn, $CeO_2$, MgO, $La_2O_3$, $Mn_3O_4$, $Na_2WO_4$, MnO, ZnO, and combinations thereof, on various supports. A number of doping elements have also proven to be useful in combination with the above catalysts.

Since the OCM reaction was first reported over thirty years ago, it has been the target of intense scientific and commercial interest, but the fundamental limitations of the conventional approach to C—H bond activation appear to limit the yield of this attractive reaction under practical operating conditions. Specifically, numerous publications from industrial and academic labs have consistently demonstrated characteristic performance of high selectivity at low conversion of methane, or low selectivity at high conversion (J. A. Labinger, *Cat. Lett.*, 1:371, 1988). Limited by this conversion/selectivity threshold, no OCM catalyst has been able to exceed 20-25% combined $C_2$ yield (i.e., ethane and ethylene), and more importantly, all such reported yields operate at extremely high temperatures (>800° C.). Novel catalysts and processes have been described for use in performing OCM in the production of ethylene from methane at substantially more practicable temperatures, pressures and catalyst activities. These are described in, for example, U.S. Patent Publication Nos. 2012/0041246, 2013/0023709, 2013/165728, 2014/0012053 and 2014/0018589, each of which is entirely incorporated herein by reference for all purposes.

An OCM reactor can include a catalyst that facilitates an OCM process. The catalyst may include a compound including at least one of an alkali metal, an alkaline earth metal, a transition metal, and a rare-earth metal. The catalyst may be in the form of a honeycomb, packed bed, or fluidized bed. In some embodiments, at least a portion of the OCM catalyst in at least a portion of the OCM reactor can include one or more OCM catalysts and/or nanostructure-based OCM catalyst compositions, forms and formulations described in, for example, U.S. Patent Publication Nos. 2012/0041246, 2013/0023709, 2013/0158322, 2013/0165728 and 2014/0274671, each of which is entirely incorporated herein by reference. Using one or more nanostructure-based OCM catalysts within the OCM reactor, the carbon efficiency of the OCM process can be at least 50%, at least 60%, at least 70%, at least 80%, or at least 90%.

Adiabatic and Non-Adiabatic Staged Reactors

An adiabatic process is one that may occur without transfer of heat or matter between a thermodynamic system and its surroundings. In an adiabatic process, energy may be transferred to its surroundings only as work. Some chemical and physical processes may occur so rapidly that they may be conveniently described by the term "adiabatic approximation," meaning that there may not be enough time for the transfer of energy as heat to take place to or from the system. By way of example, the adiabatic flame temperature is an idealization that uses the "adiabatic approximation" so as to provide an upper limit calculation of temperatures produced by combustion of a fuel. The adiabatic flame temperature is the temperature that may be achieved by a flame if the process of combustion took place in the absence of heat loss to the surroundings.

For a closed system, one may write the first law of thermodynamics as: $\Delta U=Q+W$, where $\Delta U$ denotes the change of the system's internal energy, Q the quantity of energy added to it as heat, and W the work done on it by its surroundings. If the system has rigid walls such that work may not be transferred in or out (W=0), and the walls of the system are not adiabatic and energy is added in the form of heat (Q>0), and there is no phase change, the temperature of the system may rise. If the system has rigid walls such that pressure-volume work cannot be done, and the system walls are adiabatic (Q=0), but energy is added as isochoric work in the form of friction or the stirring of a viscous fluid within the system (W>0), and there is no phase change, the temperature of the system may rise. If the system walls are adiabatic (Q=0), but not rigid (W≠0), and, in a fictive idealized process, energy is added to the system in the form of frictionless, non-viscous pressure-volume work, and there is no phase change, the temperature of the system may rise. Such a process sometimes is called an isentropic process and is said to be "reversible". Fictively, if the process is reversed, the energy added as work can be recovered entirely as work done by the system. If the system contains a compressible gas and is reduced in volume, the uncertainty of the position of the gas may be reduced, and seemingly may reduce the entropy of the system, but the temperature of the system may rise as the process is isentropic ($\Delta S=0$). Should the work be added in such a way that friction or viscous forces are operating within the system, then the process may not be isentropic, and if there is no phase change, then the temperature of the system may rise, the process is said to be "irreversible," and the work added to the system may not be entirely recoverable in the form of work.

Adiabatic processes may be irreversible (entropy is produced). Energy may be transferred as work into an adiabatically isolated system. In some cases, there may be no entropy produced within the system (no friction, viscous dissipation, etc.), and the work may only be pressure-volume work (denoted by P dV). This may occur only approximately, because it may demand a substantially slow process and no sources of dissipation. In some cases, the work is isochoric work (dV=0), for which energy may be added as work solely through friction or viscous dissipation within the system. A stirrer that transfers energy to a viscous fluid of an adiabatically isolated system with rigid walls, without phase change, may cause a rise in temperature of the fluid, but that work may not be recoverable. Isochoric work may be irreversible. An aspect of the present disclosure provides a method for controlling a temperature and influencing product composition within an oxidative coupling of methane (OCM) reactor by using a staged reactor design. The staged reactor may comprise combinations of adiabatic and non-adiabatic sections. An adiabatic section may be distinguished by insulation, or the lack of significant external convective heat transfer.

A non-adiabatic section of a reactor may be in thermal communication with a heat transfer medium. Energy may flow from the process gas to the heat transfer medium if the heat transfer medium is lower in temperature than the process gas. Energy may from the heat transfer medium to the process gas if the heat transfer medium is higher in temperature than the process gas. The non-adiabatic section can be distinguished by a convective heat transfer fluid external to the bed. Alternatively, the non-adiabatic section can be distinguished by having a low Grashof number (Gr). The Grashof number (Gr) is a dimensionless number in fluid dynamics and heat transfer which approximates the ratio of the buoyancy to viscous force acting on a fluid. Free convection is caused by a change in density of a fluid due to a temperature change or gradient. The density may decrease due to an increase in temperature and causes the fluid to rise. This motion may be caused by the buoyancy force. The major force that resists the motion may be the viscous force. The Grashof number is a way to quantify the opposing forces. The Grashof number at the outer wall of the non-adiabatic section is typically <1, dependent on the characteristic length.

The non-adiabatic section may also be distinguished by the Nusselt Number. Nusselt number (Nu) is the ratio of convective to conductive heat transfer across (normal to) the boundary. In this context, convection may include both advection and diffusion. Nu may be a dimensionless number. The conductive component may be measured under the same conditions as the heat convection but with a (hypothetically) stagnant (or motionless) fluid. A similar non-dimensional parameter may be Biot number, with the difference that the thermal conductivity is of the solid body and not the fluid. This number may give an idea that how heat transfer rate in convection is related to the resulting of heat transfer rates in conduction, e.g., a system comprising a hot fluid getting heated which is in contact with a metal wall. A Nusselt number close to one, namely convection and conduction of similar magnitude, may be characteristic of "slug flow" or laminar flow. A larger Nusselt number may correspond to more active convection, with turbulent flow typically in the 100-1000 range. The convection and conduction heat flows may be parallel to each other and to the surface normal of the boundary surface, and may be all perpendicular to the mean fluid flow in the simple case.

The Nusselt Number at an outer wall of the non-adiabatic section may be less than about 1000, 100, 10, 1, or less, depending on the characteristic length.

Characteristic length is a term that may be used to represent a typical dimension in a fluid flow medium when studying it in fluid mechanics. It can be anything. For example, for internal flows of air (which is a fluid) in a room, then any of the length L, width W, or height H can be chosen as a characteristic length depending on the direction of the flow. Similarly, for external or internal flows over or inside a circular cylinder, the diameter D, or maybe the length L can be chosen as the length scale depending on the flow direction.

If the oxidative coupling of methane reaction is occurring within a non-adiabatic section of a reactor that is in thermal communication with a heat transfer medium (such as a heat transfer fluid), and the heat transfer medium has a lower temperature than the process gas, the process gas may reach a temperature lower than a temperature of a process gas generated by an OCM reaction occurred in a substantially adiabatic section of a reactor.

Additionally, if the process gas is inside a non-adiabatic section of a reactor that is in thermal communication with a heat transfer medium and the process gas is too low in temperature for the oxidative coupling of methane to occur, the heat transfer medium can heat the process gas if the heat transfer medium is higher in temperature than the process gas.

A non-adiabatic section of a reactor that is in thermal communication with a heat transfer medium can therefore be used to heat or cool the process gas. Incorporating a non-adiabatic section of a reactor that is in thermal communication with a heat transfer medium can serve to control a temperature of the process gas within the reactor.

An adiabatic section of a reactor can be insulated. Within an adiabatic section of an OCM reactor, a temperature of the process gas may monotonically increase along a length of the adiabatic section. This may be caused by the exothermic reaction of oxygen with methane and other $C_{2+}$ hydrocarbons. As the process gas flows through the adiabatic section, oxygen is depleted.

FIG. 1A shows an oxidative coupling of methane system 100 that includes an adiabatic section and a non-adiabatic section. A source containing methane 101 and a source containing oxygen 102 are injected into a section of a reactor that is non-adiabatic and in thermal communication with a heat transfer medium 103, and then subsequently injected into a section of a reactor that is substantially adiabatic 104.

Figure 1B:
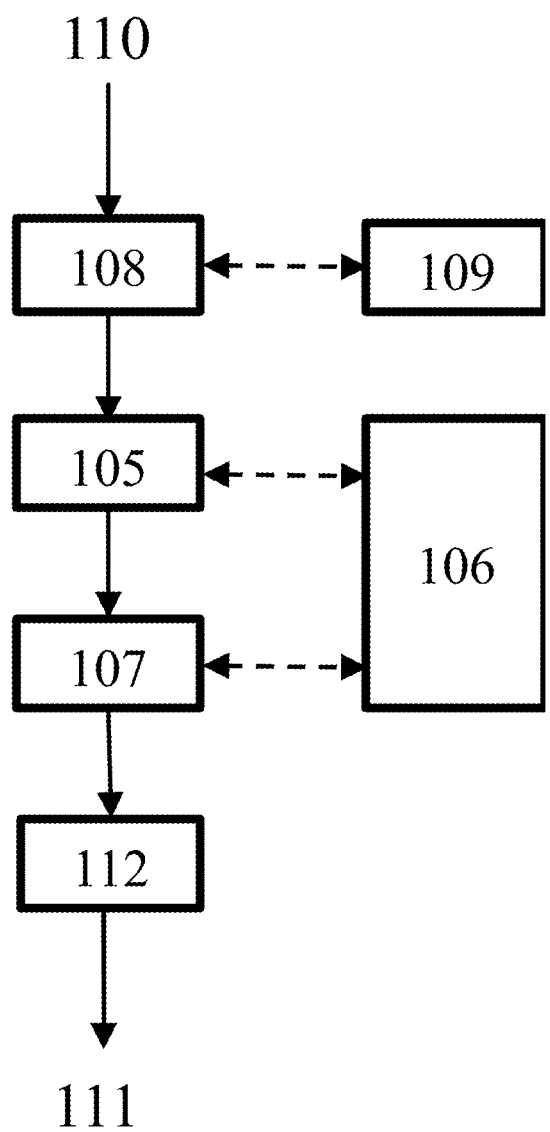
FIG. 1B shows an example of an OCM system that comprises a light-off section.

In some cases, the reactor has an isothermal section and a light-off section before the isothermal section. As shown in FIG. 1B, the OCM feed (e.g., comprising methane and oxygen) can be mixed and enter the light-off section 105. The light-off section can have a first OCM catalyst that initiates an OCM reaction at a low temperature (e.g., less than about 600° C., less than about 550° C., less than about 500° C., less than about 450° C., or less than about 400° C.). The light-off section can be in thermal communication with a heat transfer medium 106, such as a molten salt. In some cases, the isothermal section 107 and the light-off section use the same molten salt. In some instances, there is a heating section 108 of the reactor before the light-off section, which can be in thermal communication with a heat transfer medium 109. In some embodiments, the heat transfer medium in thermal communication with the heating section is different than the medium in communication with the light-off section (i.e., because having a molten salt mix between a heating section and a cooling section may not ideal for either heating or cooling). With continued reference to FIG. 1B, the OCM feed 110 can be converted to OCM products 111 including $C_{2+}$ compounds and non-$C_{2+}$ impurities. The OCM reactor can include an adiabatic section 112 as described herein, i.e., which may be insulated as opposed to being in contact with a heat transfer medium.

The source containing methane or the source containing oxygen can also include ethane. The source containing methane or the source containing oxygen can also include propane.

The source containing oxygen and/or the source containing methane can be injected in different locations of the reactor. The source containing oxygen and/or the source containing methane can be injecting using a diffuser tube.

The source containing oxygen can be the same as the source containing methane. This can be the case if a stream containing methane and substantially no oxygen is mixed with a stream containing oxygen and substantially no methane in a section of the reactor that is upstream of the non-adiabatic section that is in thermal communication with a heat transfer medium.

Over time, the oxidative coupling of methane catalyst can become deactivated. This deactivation can be characterized by a reduction in the maximum temperature in the non-adiabatic section of the reactor that is in thermal communication with a heat transfer medium. With deactivation, there can be a corresponding reduction in the conversion of oxygen in the non-adiabatic section. As the oxidative coupling of methane catalyst in the non-adiabatic section becomes deactivated, the concentration of $O_2$ at the outlet of the non-adiabatic section that is in thermal communication with a heat transfer medium increases. The gas at the exit of the non-adiabatic section that is in thermal communication with at heat transfer medium is an intermediate gas stream.

The intermediate gas stream may contain at least about 100 parts per million (ppm) oxygen, at least about 150 parts per million (ppm) oxygen, at least about 200 parts per million (ppm) oxygen, at least about 250 parts per million (ppm) oxygen, at least about 300 parts per million (ppm) oxygen, at least about 350 parts per million (ppm) oxygen, at least about 400 parts per million (ppm) oxygen, at least about 450 parts per million (ppm) oxygen, at least about 500 parts per million (ppm) oxygen, at least about 550 parts per million (ppm) oxygen, at least about 600 parts per million (ppm) oxygen, at least about 1000 parts per million (ppm) oxygen, or more.

As the oxidative coupling of methane catalyst deactivates, the concentration of oxygen at the exit of the non-adiabatic section of the reactor may increase. This corresponds to an increased concentration of oxygen in the substantially adiabatic section of the reactor. The increased oxygen concentration in the substantially adiabatic section of the reactor corresponds to an increased temperature at the outlet of the substantially adiabatic section of the reactor.

As the oxidative coupling of methane catalyst deactivates, one or more of the following may occur: (i) a concentration of oxygen at an outlet of the non-adiabatic section in thermal communication with a heat transfer medium may increase, (ii) a temperature at the outlet of the non-adiabatic section of the reactor that is in thermal communication with a heat transfer medium may decrease, (iii) the concentration of oxygen at an inlet of the substantially adiabatic section may increase, and (iv) a temperature at an outlet of the substantially adiabatic section may increase.

The percentage of catalyst deactivation in the non-adiabatic section that is in thermal communication with a heat transfer medium may correspond to the oxygen conversion ($x_{O2}$) at some time $t_o$ compared with the conversion at some later time t, such that catalyst deactivation=$[1-x_{O2}(t)/x_{O2}(t_o)]*100$. For example, on day 1 the conversion of oxygen in the non-adiabatic section in thermal communication with a heat transfer medium is 0.99, and on day 100 the conversion of oxygen in the non-adiabatic section that is in thermal communication with a heat transfer medium is 0.95. The percentage of catalyst deactivation is then $[1-(0.95)/(0.99)]*100=4.04\%$.

The temperature at the outlet of the substantially adiabatic section may increase over time with deactivation. Under any deactivation percentage, the temperature at the outlet of the substantially adiabatic section may be between 500-1000° C., between 550-1000° C., between 600-1000° C., between 700-1000° C., between 700-950° C., between 700-900° C., between 750-900° C., or between 750-850° C.

Figure 2:
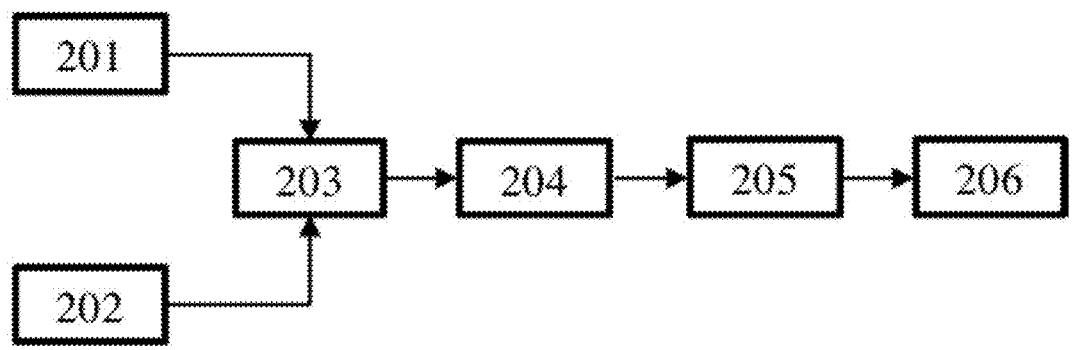
FIG. 2 shows an oxidative coupling of methane system that comprises a mixer, an adiabatic section, and a non-adiabatic section.

FIG. 2 shows an oxidative coupling of methane system 200 that uses a mixer, an adiabatic section, and a non-adiabatic section. A source containing methane 201, and a source containing an oxidizing agent (e.g., oxygen) 202 are injected into a mixer 203 to produce a mixed gas stream. The temperature of the mixed gas stream is increased in a heater 204 to bring it to a temperature at which the oxidative coupling of methane reaction can occur to produce a heated mixed gas stream. The heated mixed gas stream can then be injected into a section of a reactor that is non-adiabatic and in thermal communication with a heat transfer medium 205 to produce an intermediate gas stream. The intermediate gas stream can then be injected into a substantially adiabatic section of the reactor 206.

The concentration of the oxidizing agent at the inlet of the non-adiabatic section of the reactor that is in thermal communication with a heat transfer medium may be greater than or equal to about 0.1%, 0.5%, 1%, 1.5%, 2%, 5%, 10%, 20% (mol %), or more.

The concentration of oxygen at the inlet of the substantially adiabatic section may be decreased to a percentage of its inlet concentration, and can be decreased to at least about 0.1%, at least about 0.5%, at least about 1%, at least about 2%, at least about 5%, at least about 10%, or at least about 20% of its inlet concentration.

The time that it takes for the gas to travel between the non-adiabatic section that is in thermal communication with a heat transfer medium and the section that is substantially adiabatic section may be less than about 100 milliseconds (ms), less than about 80 milliseconds (ms), less than about 50 milliseconds (ms), less than about 20 milliseconds (ms), less than about 10 milliseconds (ms), less than about 5 milliseconds (ms), less than about 2 milliseconds (ms) or less than about 1 millisecond (ms). The concentration of oxygen ($O_2$) that exits the adiabatic section may be less than or equal to about 1 mol %, 0.5 mol %, 0.2 mol %, 1000 parts per million (ppm), 500 ppm, 400 ppm, 300 ppm, 200 ppm, 100 ppm, 90 ppm, 80 ppm, 70 ppm, 60 ppm, 50 ppm, 20 ppm, 10 ppm, 5 ppm or less.

The temperature at the outlet of the adiabatic section may be greater than or equal to about 600° C., 700° C., 800° C., 850° C., 880° C., 900° C., 920° C., 950° C. or more.

The temperature of the process gas within the non-adiabatic section of the reactor that is in thermal communication with a heat transfer medium may reach a maximum within the non-adiabatic section. The maximum temperature within the non-adiabatic section that is in thermal communication with a heat transfer medium may be less than or equal to about 1150° C., 1100° C., 1050° C., 1000° C., 950° C., 900° C., 850° C., 800° C., or less.

The temperature of the source containing oxygen and the source containing methane before entering into the mixer may be less than or equal to about 600° C., 550° C., 500° C., 450° C., 400° C., 350° C., or less.

The temperature of the source containing oxygen and the source containing methane before entering into the mixer may be less than or equal to about 20 bar(gauge, "g"), less than or equal to about 15 bar(g) less than or equal to about 10 bar(g), less than or equal to about 8 bar(g), less than or equal to about 6 bar(g), less than or equal to about 4 bar(g) or less than or equal to about 2 bar(g).

Figure 3:
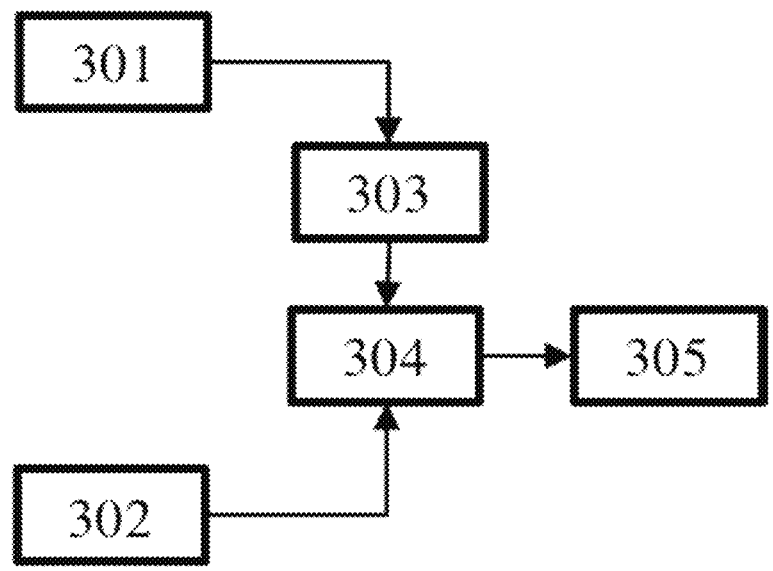
FIG. 3 shows an oxidative coupling of methane system that comprises a methane preheat section, an adiabatic section, and a non-adiabatic section.

FIG. 3 shows an oxidative coupling of methane system 300 that uses methane preheat, adiabatic, and non-adiabatic sections. A source containing methane 301 is injected into a methane preheater 303 to produce a preheated methane stream. The preheated methane stream and a source containing oxygen 302 are mixed to produce a mixture, and injected into a non-adiabatic section of a reactor that is in contact with a heat transfer medium 304 to produce an intermediate gas stream. The intermediate gas stream is injected into a substantially adiabatic section of a reactor 305.

The source containing methane may be preheated to a temperature of greater than or equal to about 300° C., 350° C., 400° C., 450° C., at 500° C., 550° C., or 600° C.

Once the preheated methane stream is mixed with the source containing oxygen to produce the mixture, the temperature of the mixture may be less than or equal to about 800° C., less than or equal to about 700° C., less than or equal to about 600° C., less than or equal to about 550° C., less than or equal to about 500° C., or less than or equal to about 450° C.

Before the source containing oxygen is mixed with the preheated methane stream, the source containing oxygen may have a temperature of less than or equal to about 300° C., less than or equal to about 250° C., less than or equal to about 200° C., less than or equal to about 150° C., or less than or equal to about 100° C.

When the mixture is injected into the non-adiabatic section of the reactor, it can flow over an inert packing or an oxidative coupling of methane catalyst. The inert packing can be alumina ($Al_2O_3$), silica ($SiO_2$), $Fe_2O_3$, MgO, $Na_2O$, another metal oxide, or combinations thereof.

In another aspect, described herein is a method for producing an olefin. The method can comprise providing a reactor having an isothermal section. The isothermal section can contain a catalyst capable of promoting an oxidative coupling of methane (OCM) reaction and can be in thermal communication with a heat transfer medium. In some cases, the isothermal section comprises the heat transfer medium. The method can include introducing a gas mixture into the isothermal section of the reactor. The gas mixture comprises oxygen ($O_2$) and methane ($CH_4$), whereby at least about 75 mol % of the $O_2$ reacts with the $CH_4$ to produce $C_{2+}$ compounds and non-$C_{2+}$ impurities.

In some cases, the catalyst promotes an OCM reaction having a selectivity for $C_{2+}$ compounds of at least about 50% at 700° C. In some instances, the catalyst promotes an OCM reaction having a selectivity for $C_{2+}$ compounds of at least about 60% at 750° C. In some embodiments, the catalyst promotes an OCM reaction having a selectivity for $C_{2+}$ compounds of at least about 65% at 800° C. In some cases, the gas mixture is introduced into the isothermal section at a temperature between about 650° C. and about 750° C. In some cases, the gas mixture exits the isothermal section at a temperature between about 800° C. and about 900° C.

The gas mixture can contain any suitable amount of $O_2$ when it enters the isothermal section. In some cases, the gas mixture contains between about 13% and about 17% (mol %) $O_2$ when it enters the isothermal section. In some cases, the gas mixture contains greater than or equal to about 5%, 8%, 10%, 12%, 14%, 16%, 18%, 20%, 25% (mol %) $O_2$, or more, when it enters the isothermal section. In some cases, the gas mixture contains less than or equal to about 25%, 20%, 18%, 16%, 14%, 12%, 10% 8% (mol %) $O_2$, or less when it enters the isothermal section.

The gas mixture can contain any suitable amount of $O_2$ when it exits the isothermal section. In some cases, the gas mixture contains between about 0.5% and about 3% (mol %) $O_2$ when it exits the isothermal section. In some cases, the gas mixture contains greater than or equal to about 0.1%, 0.3%, 0.5%, 1%, 2%, 3%, 5%, 7%, 10% (mol %) $O_2$, or more when it exits the isothermal section. In some cases, the gas mixture contains less than or equal to about 10%, 7%, 5%, 3%, 2%, 1%, 0.5%, 0.3%, 0.1% (mol %) $O_2$, or less when it exits the isothermal section.

Any suitable amount of the $CH_4$ is converted to $C_{2+}$ compounds and non-$C_{2+}$ impurities in the isothermal section. In some cases, between about 12% and about 16% (mol %) of the $CH_4$ is converted to $C_{2+}$ compounds and non-$C_{2+}$ impurities in the isothermal section. In some embodiments, greater than to equal to about 3%, 5%, 7%, 10%, 12%, 14%, 16%, 18%, 20% (mol %) of the $CH_4$, or more is converted to $C_{2+}$ compounds and non-$C_{2+}$ impurities in the isothermal section. In some embodiments, less than or equal to about 20%, 18%, 16%, 14%, 12%, 10%, 9%, 7%, 5%, 3% (mol %) of the $CH_4$, or less is converted to $C_{2+}$ compounds and non-$C_{2+}$ impurities in the isothermal section.

The catalyst in the isothermal section can be a perovskite or comprises a lanthanide element. In some cases, the catalyst does not shrink or sinter when operated at OCM performance conditions.

A relatively large amount of the $O_2$ can be reacted in the isothermal section. In some cases, greater than or equal to about 70%, 75%, 80%, 85%, 90%, 95% (mol %) of the $O_2$, or more reacts with the $CH_4$ to produce $C_{2+}$ compounds and non-$C_{2+}$ impurities. In some cases, less than or equal to about 95%, 90%, 85%, 80%, 75%, 70% (mol %) of the $O_2$, or less reacts with the $CH_4$ to produce $C_{2+}$ compounds and non-$C_{2+}$ impurities.

The reactor can further comprise a light-off section in fluid communication with and upstream from the isothermal section. The light-off section can be in thermal communication with an additional heat transfer medium and contains a catalyst capable of promoting an OCM reaction. The light-off section may comprise the additional heat transfer medium. The catalyst in the light-off section can be different than the OCM catalyst in the isothermal section.

The method can further comprise introducing a gas mixture into the light-off section of the reactor. The gas mixture can comprises oxygen ($O_2$) and methane ($CH_4$), whereby at least at least some of the $O_2$ reacts with the $CH_4$ to produce $C_{2+}$ compounds before the gas mixture enters the isothermal section.

The heat transfer medium and the additional heat transfer medium can be molten salts, optionally the same molten salt. Any suitable molten salt can be used. In some cases, the molten salt has a melting point less than about 700° C. and a boiling point greater than about 700° C. In some cases, the melting point is less than about 400° C., less than about 450° C., less than about 500° C., less than about 550° C., less than about 600° C., less than about 650° C., less than about 700° C., or less than about 750° C. In some cases, the boiling point is greater than about 600° C., greater than about 650° C., greater than about 700° C., greater than about 750° C., greater than about 800° C., greater than about 850° C., greater than about 900° C., or greater than about 950° C. The molten salt does not decompose at the operating temperature of OCM.

The molten salt can be any suitable salt. Suitable anions can include chlorides, fluorides, fluoroborates, perchlorates, carbonates, or oxides. Suitable cations can include any element from groups 1 to 14 of the periodic table. The molten salt can include a mixture of salts, such as a eutectic mixture. Particular eutectic mixtures include $MgCl_2$/KCl (e.g., at 33/67 mol %); NaCl/KCl/$ZnCl_2$ (e.g., at 8-10%/10-20%/60-80 mol %); and LiF/NaF/$BeF_2$ (e.g., at 31/31/38 mol %).

The catalyst in the light-off section can promote an OCM reaction having a selectivity for $C_{2+}$ compounds of at least about 30% at 550° C. In some embodiments, the catalyst in the light-off section can promote an OCM reaction having a selectivity for $C_{2+}$ compounds of at least about 40% at 600° C.

In some cases, the reactor further comprises a heating section in fluid communication with and upstream of the light-off section, which heating section is in thermal communication with a further additional heat transfer medium, which is optionally a molten salt. The heating section may comprise the further additional heat transfer medium. Suitable molten salts are described above. In some cases, the molten salt in contact with the heating section does not mix with the molten salt in contact with the light-off or isothermal sections of the OCM reactor.

The gas mixture can be introduced into the light-off section at any suitable temperature. In some embodiments, the temperature is between about 450° C. and about 580° C. In some cases, the temperature at the inlet to the light-off section is less than about 650° C., less than about 620° C., less than about 600° C., less than about 580° C., less than about 560° C., less than about 540° C., less than about 520° C., less than about 500° C., less than about 480° C., less than about 460° C., less than about 440° C., less than about 420° C., or less than about 400° C.

The gas mixture can exit the light-off section at any suitable temperature. In some embodiments, the gas mixture exits the light-off section at a temperature between about 650° C. and about 750° C. In some cases, the exit temperature is about 550° C., about 600° C., about 650° C., about 700° C., about 750° C., about 800° C., or about 850° C.

Any suitable amount of $CH_4$ can be converted to $C_{2+}$ compounds and non-$C_{2+}$ impurities in the light-off section. In some cases, between about 3% and about 5% (mol %) of the $CH_4$ in the feed is converted to $C_{2+}$ compounds and non-$C_{2+}$ impurities in the light-off section. In some embodiments, greater than or equal to about 1%, 2%, 3%, 4%, 5%, 6%, 7%, 8% (mol %) of the $CH_4$, or more is converted to $C_{2+}$ compounds and non-$C_{2+}$ impurities in the light-off section.

The gas mixture can contain any suitable amount of $O_2$ when it enters the light-off section. In some cases, the gas mixture contains between about 15% and about 20% (mol %) $O_2$ when it enters the light-off section. In some embodiments, the gas mixture contains greater than or equal to about 5%, 10%, 15%, 20%, 25%, 30%, 35% (mol %) $O_2$, or more when it enters the light-off section. In some embodiments, the gas mixture contains less than or equal to about 35%, 30%, 25%, 20%, 15%, 10% (mol %) $O_2$, or less when it enters the light-off section.

The gas mixture can contain any suitable amount of $O_2$ when it exits the light-off section. In some cases, the gas mixture contains between about 13% and about 17% (mol %) $O_2$ when it exits the light-off section. In some embodiments, the gas mixture contains greater than or equal to about 5%, 10%, 15%, 20%, 25%, 30%, 35% (mol %) $O_2$, or more when it exits the light-off section. In some embodiments, the gas mixture contains less than or about 35%, 30%, 25%, 20%, 15%, 10%, (mol %) $O_2$, or less when it exits the light-off section.

The catalyst in the light-off section can be any material which catalyzes an OCM reaction at the conditions in the OCM reactor. In some cases, the catalyst comprises nanowires. The catalyst in the light-off section can be capable of performing oxidative dehydrogenation (ODH). Suitable catalysts can be found in U.S. Pat. Nos. 9,718,054 and 8,962,517, each of which are incorporated herein by reference in their entirety.

Any suitable amount of the $O_2$ entering the light-off section can be converted to $C_{2+}$ compounds and non-$C_{2+}$ impurities. In some embodiments, greater than or equal to about 5%, 10%, 15%, 20%, 25%, 30% (mol %) of the $O_2$, or more entering the light-off section reacts with the $CH_4$ to produce $C_{2+}$ compounds and non-$C_{2+}$ impurities. In some embodiments, less than or equal to about 30%, 25%, 20%, 15%, 10% (mol %) of the $O_2$, or less entering the light-off section reacts with the $CH_4$ to produce $C_{2+}$ compounds and non-$C_{2+}$ impurities.

In some embodiments, the reactor further comprises an adiabatic section in fluid communication with and downstream from the isothermal section. The adiabatic section can be insulated and contain a catalyst capable of promoting an OCM reaction. The catalyst in the adiabatic section can be different than or the same as the catalyst in the light-off and isothermal sections of the reactor. In some cases, the catalyst is a perovskite. In some embodiments, the catalyst also performs oxidative dehydrogenation (ODH).

In some cases, the method further comprises introducing the gas mixture exiting the isothermal section into the adiabatic section, whereby the concentration of $O_2$ exiting the adiabatic section is less than about 2000 parts per million (ppm), less than about 1000 ppm, less than about 500 ppm, less than about 100 ppm, less than about 50 ppm, less than about 10 ppm, or less than about 5 ppm.

The adiabatic section can contain a catalyst capable of promoting an OCM reaction at a net selectivity for $C_{2+}$ compounds of between about 0% and about 20% at 850° C. In some cases the net selectivity is at least about 0%, at least about 5%, at least about 10%, at least about 15%, at least about 20%, at least about 25%, at least about 30%, or at least about 40%.

In some cases, relatively little reforming reaction takes place in the adiabatic section of the OCM reactor. In some embodiments, less than or equal to 30%, 25%, 20%, 15%, 10%, 5%, 3%, 1% (mol %) of the $CH_4$, or less that enters the adiabatic section is reformed into CO and $H_2$.

In some cases, the adiabatic section scrubs the remaining $O_2$ from the OCM product stream and relatively little methane is converted in the adiabatic section compared to the amount converted in the light-off and isothermal sections. In some instances, between about 0% and about 3% (mol %) of the $CH_4$ is converted to $C_{2+}$ compounds and non-$C_{2+}$ impurities in the adiabatic section. In some cases, less than or equal to about 15%, 10%, 5%, 3%, 2%, 1% (mol %) of the $CH_4$ in the feed, or less is converted to $C_{2+}$ compounds and non-$C_{2+}$ impurities in the adiabatic section.

Ethane can be added to the adiabatic section. The method can further comprise adding between about 0% and about 5% (mol %) ethane ($C_2H_6$) to the gas mixture near the inlet of the adiabatic section.

The gas mixture can enter the adiabatic section at any suitable temperature. In some cases, the gas mixture is introduced into the adiabatic section at a temperature between about 800° C. and about 900° C. In some cases, the inlet temperature is at least about 650° C., at least about 700° C., at least about 750° C., at least about 800° C., at least about 850° C., at least about 900° C., or at least about 950° C. In some cases, the inlet temperature is at most about 650° C., at most about 700° C., at most about 750° C., at most about 800° C., at most about 850° C., at most about 900° C., or at most about 950° C.

The gas mixture can exit the adiabatic section at any suitable temperature. In some cases, the gas mixture exits the adiabatic section at a temperature between about 850° C. and about 950° C. In some cases, the exit temperature is at least about 650° C., at least about 700° C., at least about 750° C., at least about 800° C., at least about 850° C., at least about 900° C., or at least about 950° C. In some cases, the exit temperature is at most about 650° C., at most about 700° C., at most about 750° C., at most about 800° C., at most about 850° C., at most about 900° C., or at most about 950° C.

The reactor can further comprise a post-bed cracking (PBC) section in fluid communication with and downstream of the adiabatic section, which PBC section converts $C_2H_6$ into $C_2H_4$ using heat derived from OCM. The method can further comprise adding between about 1% and about 5% (mol %) ethane ($C_2H_6$) to the gas mixture near the inlet of the PBC section.

The reactor described herein, including an isothermal section and optionally a heating section, light-off section, adiabatic section and PBC section converts a relatively high amount of methane into $C_{2+}$ compounds. In some cases, greater than or equal to about 15%, 20%, 25%, 30%, 35%, 40%, 45%, 50% (mol %) of the $CH_4$ in the feed, or more is converted to $C_{2+}$ compounds and non-$C_{2+}$ impurities in the OCM reactor.

In another aspect, described herein is a system for performing oxidative coupling of methane (OCM). The system can comprise a reactor having an isothermal section and either a light-off section or an adiabatic section. The reactor can have both the light-off section and the adiabatic section.

The light-off section can be adapted to accept a gas mixture comprising oxygen ($O_2$) and methane ($CH_4$) and contains a first OCM catalyst that can convert the $O_2$ and $CH_4$ into $C_{2+}$ compounds at a selectivity of at least about 30% at 550° C., wherein the light-off section is in thermal communication with a first heat transfer medium. The light-off section may comprise the first heat transfer medium.

The isothermal section can be in fluidic communication with and downstream of the light-off section and contain a second OCM catalyst that has a selectivity for $C_{2+}$ compounds of at least about 50% at 700° C., wherein the isothermal section is in thermal communication with a second heat transfer medium. The isothermal section may comprise the second heat transfer medium.

The adiabatic section can be in fluidic communication with and downstream of the isothermal section and contain a third OCM catalyst that has a net selectivity for $C_{2+}$ compounds of at least about 0% at 850° C.

In some cases, the reactor further comprises a post-bed cracking (PBC) section in fluid communication with and downstream of the adiabatic section, which PBC section converts $C_2H_6$ into $C_2H_4$ using heat derived from OCM.

The reactor can be adapted to operate at a pressure of greater than or equal to about 2 bar(g), greater than about 4 bar(g), or greater than about 8 bar(g).

The reactor can be a tubular reactor. The first and second heat transfer medium can be the same material, such as a molten salt.

Methanation is an exothermic reaction. In some cases, the conversion in a methanation reactor is limited by the ability to handle the temperature rise of the reaction, e.g., by removing heat. If one were to practice the systems and methods described herein and use a molten salt OCM reactor, that molten salt system could also be used to cool a methanation reactor. The methanation could be performed in a separate reactor or in a separate section of the same OCM reactor (e.g., upstream of the light-off section). In some cases, the system further comprises a methanation reactor that is in fluid communication with the first heat transfer medium or the second heat transfer medium. The methanation section can be in fluidic communication with and upstream of the light-off section which contains a methanation catalyst. Further embodiments describing the use of methanation in OCM systems and suitable methanation catalysts can be found in U.S. Pat. No. 9,701,597, which is incorporated herein by reference in its entirety.

In some cases, the source containing methane and the source containing oxygen can be mixed before being heated, and subsequently be heated over an inert packing in the non-adiabatic section of the reactor.

Figure 4:
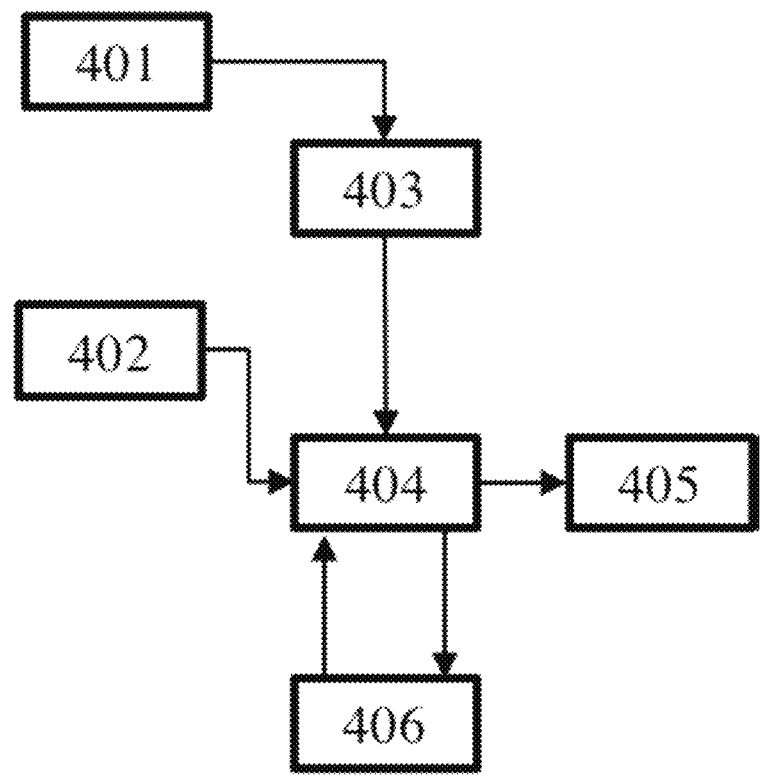
FIG. 4 shows an oxidative coupling of methane system that comprises a methane preheater and a steam superheater.

FIG. 4 shows an oxidative coupling of methane system that includes a methane preheater and a steam superheater 400. A source containing methane 401 is injected into a methane preheater 403 to produce a preheated methane stream. A source containing oxygen 402 and the preheated methane stream are injected into a non-adiabatic section of a reactor 404. The non-adiabatic section is in thermal communication with a heat transfer agent that is in circulation with a steam superheater 406. The heat transfer agent that is in circulation with a steam superheater can be a molten salt. The steam superheater can be integrated with the non-adiabatic section of the reactor in a single vessel. Effluent from the non-adiabatic section is injected into an adiabatic section of a reactor 405.

Figure 5:
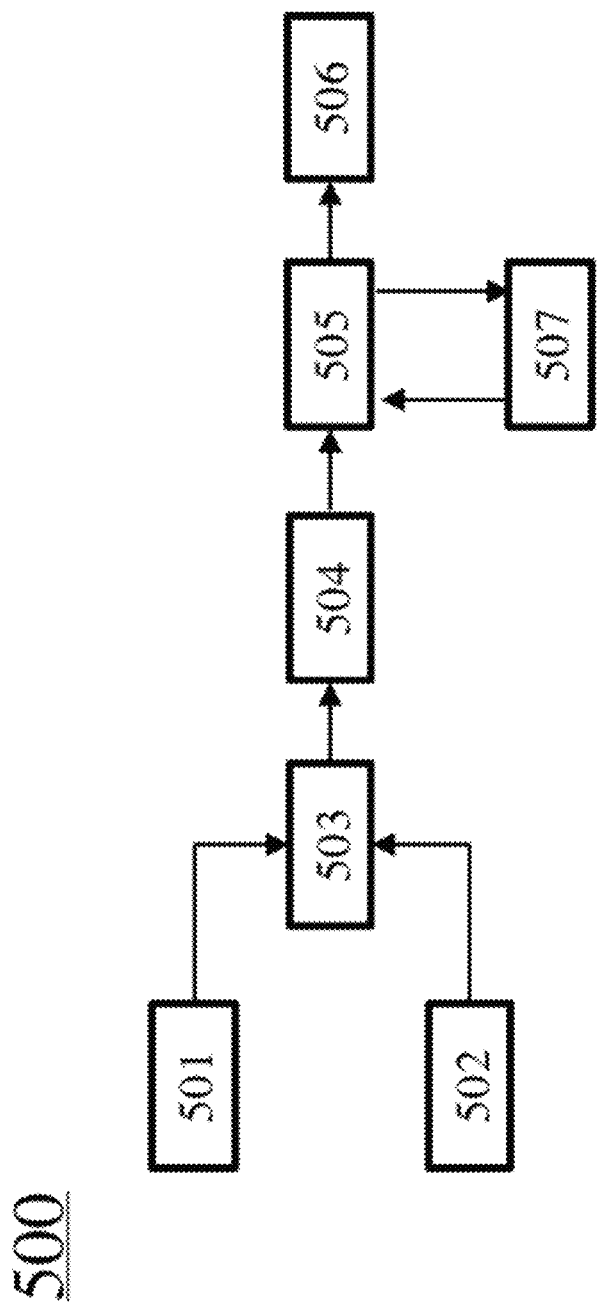
FIG. 5 shows an oxidative coupling of methane system that comprises a mixer and a steam superheater.

FIG. 5 shows an oxidative coupling of methane system that includes a mixer and a steam superheater 500. A source containing methane 501 and a source containing oxygen 502 are injected into a mixer 503 to produce a mixture. The mixture is injected into a preheater 504 to produce a preheated mixture. The preheated mixture is injected into a non-adiabatic section of a creator that is in thermal communication with a heat transfer medium. The heat transfer medium is in circulation with a steam superheater 507. The effluent of the non-adiabatic section is injected into a substantially adiabatic section 506.

Figure 6:
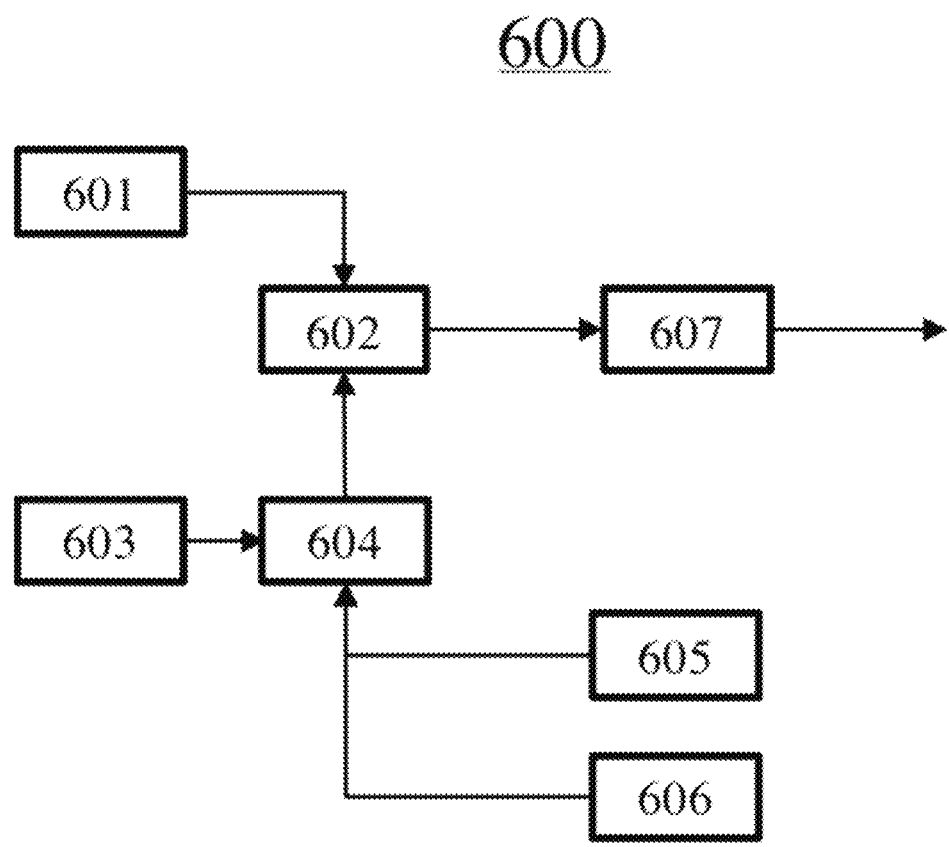
FIG. 6 shows an oxidative coupling of methane system that comprises a heat exchanger downstream of the oxidative coupling of methane reactor.

FIG. 6 shows an oxidative coupling of methane system that includes a heat exchanger downstream of the oxidative coupling of methane reactor 600. A source containing ethane 606 and a source containing methane 605 are injected into a feed preheater 604. A source containing a fuel 603 is also injected into the feed preheater 604 to produce a preheated hydrocarbon stream. The preheated hydrocarbon stream and a source containing oxygen 601 are injected into a reactor that includes at least one non-adiabatic section and at least one substantially adiabatic section 602 to produce an OCM reactor effluent. The OCM reactor effluent is subsequently injected into a heat exchanger 607.

Figure 7:
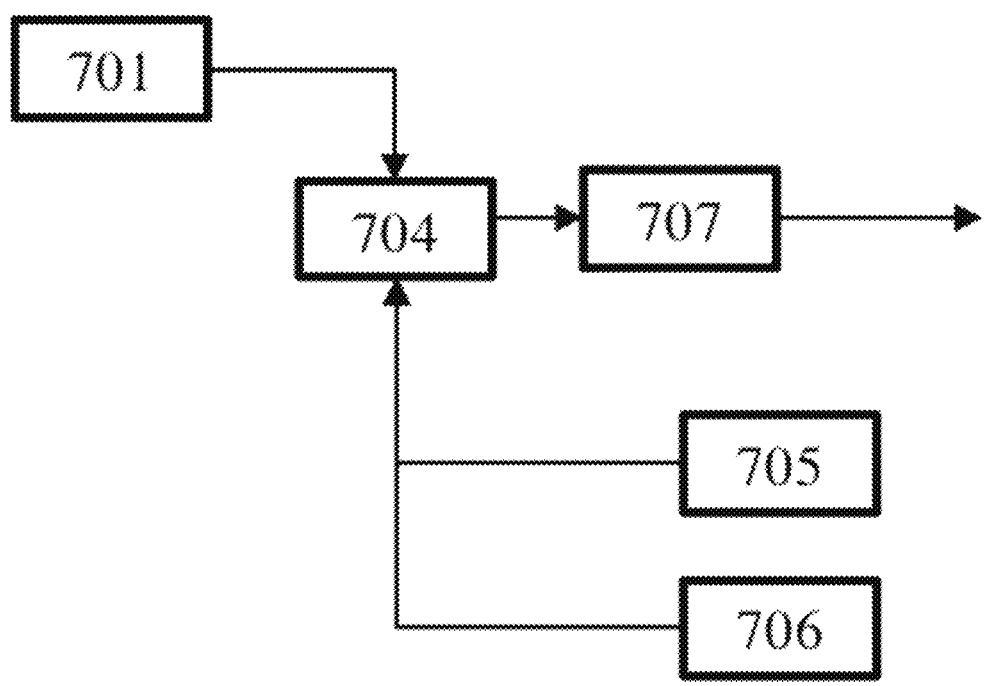
FIG. 7 shows an oxidative coupling of methane system that uses a heat transfer medium to preheat the feed gas.

FIG. 7 shows an oxidative coupling of methane system that uses a heat transfer medium to preheat the feed gas 700. A source containing oxygen 701, a source containing methane 702, and a source containing ethane 703 are injected into a reactor that includes a mixer, at least one non-adiabatic section and at least one substantially adiabatic section 704 to produce an OCM reactor effluent. The OCM reactor effluent is subsequently injected into a heat exchanger 707.

Figure 8:
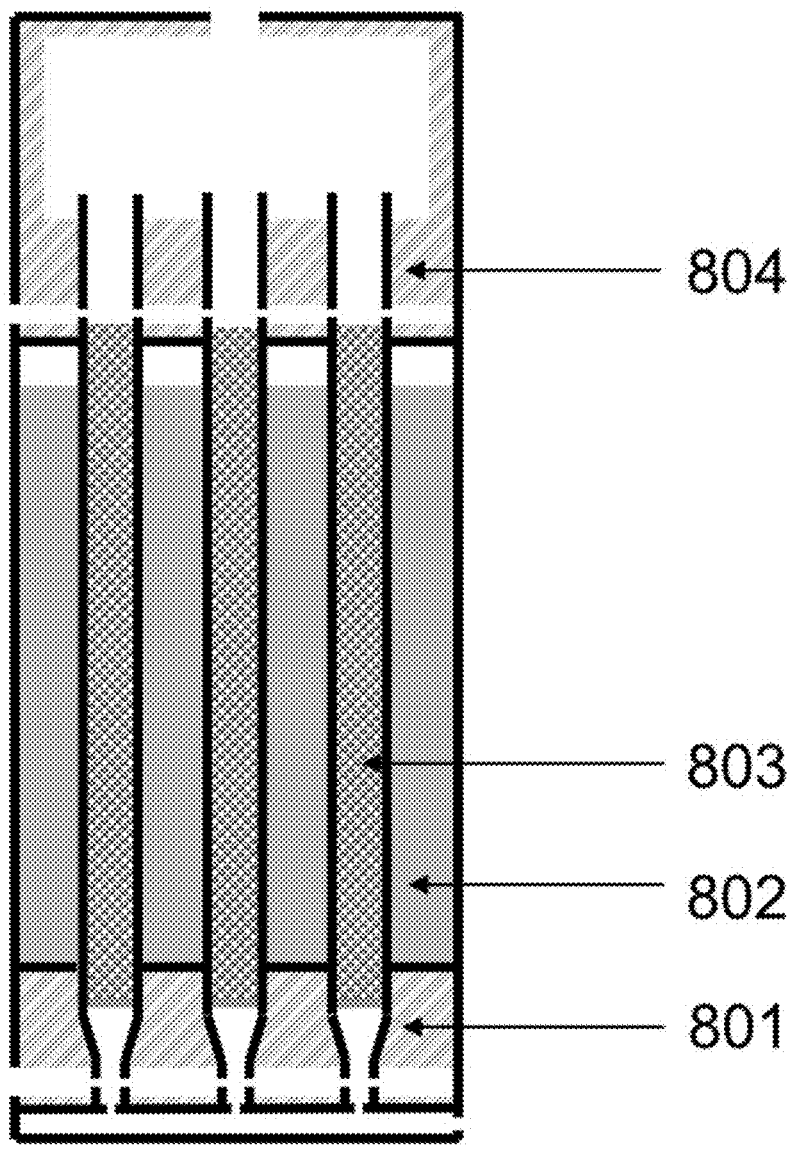
FIG. 8 shows an oxidative coupling of methane reactor that comprises an adiabatic section and a non-adiabatic section.

FIG. 8 shows an oxidative coupling of methane reactor that includes an adiabatic and non-adiabatic sections 800. The reactor may comprise tubes that contain OCM catalyst 803. One end of the tube is surrounded by insulation 801, constituting a substantially adiabatic section of the reactor. The middle section of the tubes is surrounded by a heat transfer medium 802 constituting a non-adiabatic section that is in thermal communication with a heat transfer medium. The opposing end of the tube is surrounded by insulation, constituting a second substantially adiabatic section 804.

The reactor can contain greater than or equal to about 2, 5, 10, 20, 30, 40, 50, 60, 70, 80, 90, 100 tubes or more.

The pressure drop across the tubes may be less than or equal to 3 bar(g), 2.5 bar(g), 2 bar(g), 1.5 bar(g), 1 bar(g), 0.5 bar(g) or less.

The diameter of each tube may be greater than or equal to about 0.25 inches, 0.5 inches, 0.75 inches, 1 inch, 1.25 inches or more.

The length of each tube may be greater than about 4 feet and less than about 12 feet, greater than about 5 feet and less than about 11 feet, greater than about 6 feet and less than about 10 feet, or greater than about 7 feet and less than about 9 feet.

The gas velocity in each tube may be greater than about 3 meters per second (m/s) and less than about 10 meters per second (m/s), greater than about 4 meters per second (m/s) and less than about 9 meters per second (m/s), or. greater than about 5 meters per second (m/s) and less than about 8 meters per second (m/s).

The pressure of gas within each tube may be greater than about 4 bar(g) and less than about 10 bar(g), greater than about 5 bar(g) and less than about 9 bar(g), or greater than about 6 bar(g) and less than about 8 bar(g).

In the non-adiabatic section of the reactor that is in thermal communication with a heat transfer medium, there may be a temperature gradient within each tube between the center of the tube and the wall of the tube. The temperature gradient may be at least about 1° C./inch, at least about 10° C./inch, at least about 20° C./inch, at least about 30° C./inch, at least about 40° C./inch, at least about 50° C./inch, at least about 60° C./inch, at least about 70° C./inch, at least about 80° C./inch, at least about 90° C./inch, at least about 100° C./inch, at least about 120° C./inch, at least about 150°

C./inch, at least about 175° C./inch, at least about 200° C./inch, or at least about 250° C./inch.

Figure 9:
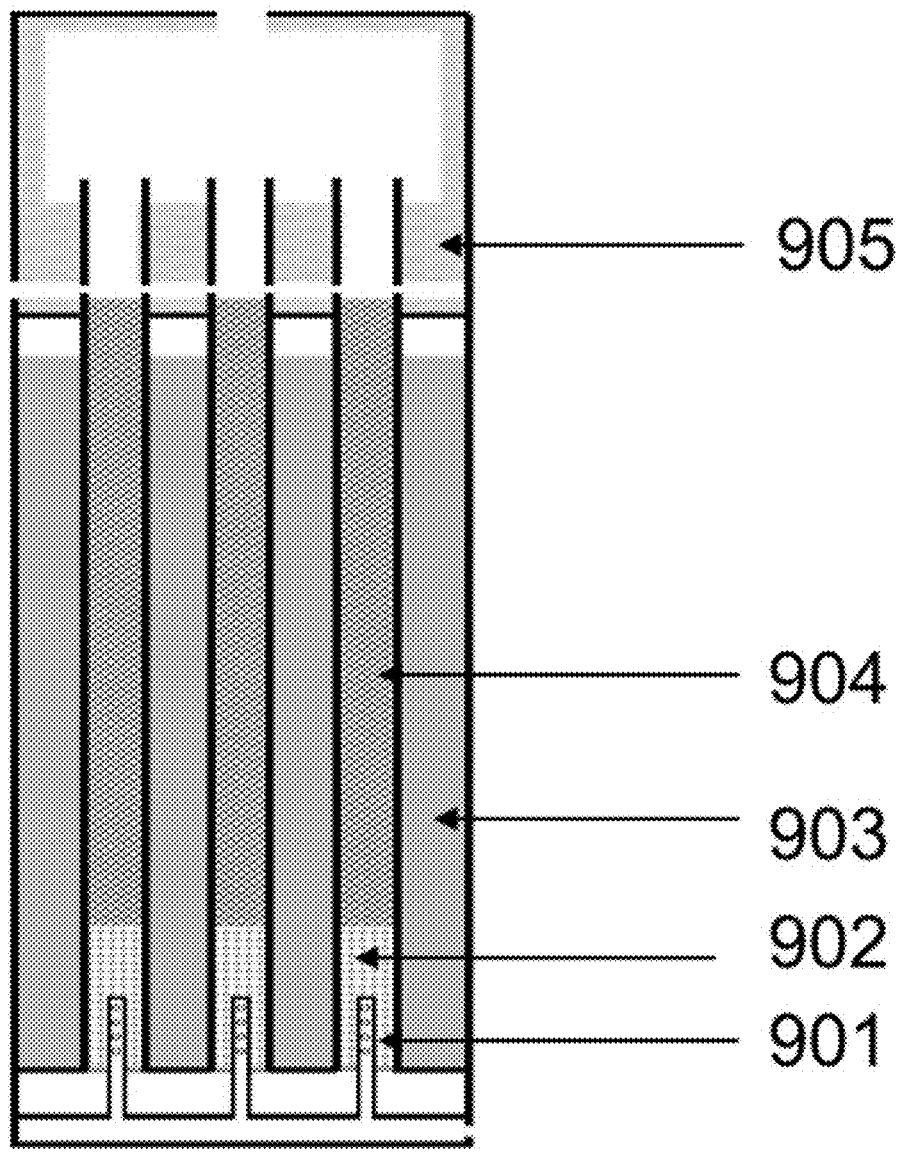
FIG. 9 shows an oxidative coupling of methane reactor that comprises diffuser tubes, adiabatic, and non-adiabatic sections.

FIG. 9 shows an oxidative coupling of methane reactor that includes diffuser tubes, adiabatic, and non-adiabatic sections 900. A feed gas is injected into the reactor using a diffuser tube 901. The reactor comprises tubes that contain catalyst 904 and inert packing material 902. The inert packing material at the entrance of the tube 902 is in a non-adiabatic section of the reactor that is in thermal communication with a heat transfer medium 903. One gas is fed into the reactor on the interior of the diffuser tube and one gas is fed on the exterior of the diffuser tube. The tubes at the exit of the reactor are surrounded by insulation, constituting a substantially adiabatic section of the reactor 905.

A portion of the substantially adiabatic section may or may not contain OCM catalyst. Ethane can optionally be added to the substantially adiabatic section of the reactor, and may undergo post bed cracking to generate ethylene.

Figure 10:
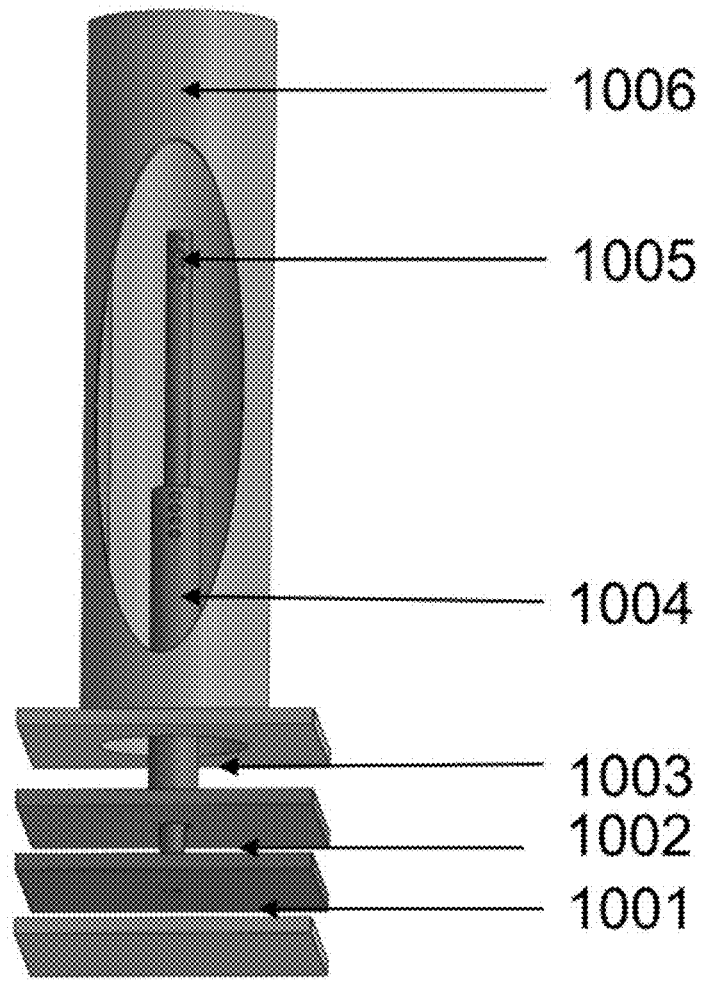
FIG. 10 shows an example of a diffuser tube.

FIG. 10 shows a diffuser tube within a reactor tube 1000. The diffuser tube may comprise a number of manifolds for the addition of gases 1001-1003. These manifolds are attached to concentric perforated tubes 1004-1005 that injects gas feeds into the reactor tube 1006.

Figure 11:
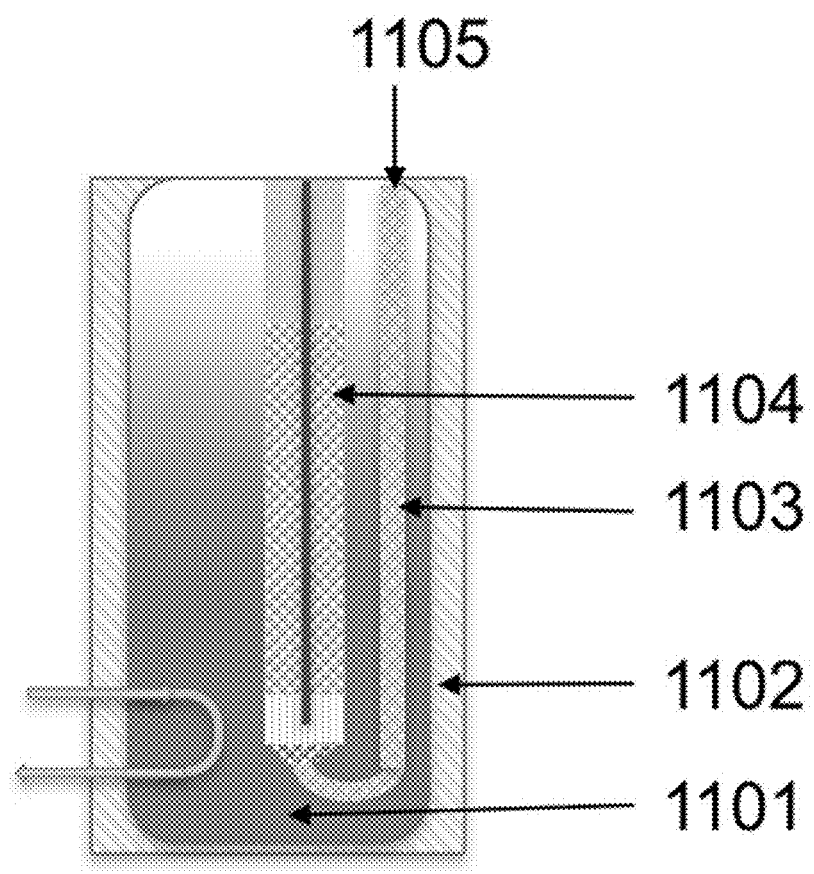
FIG. 11 shows an oxidative coupling of methane reactor that uses molten salt as a heat transfer medium.

FIG. 11 shows an oxidative coupling of methane reactor that uses molten salt as a heat transfer medium. This may include a vessel that is partially filled with molten salt 1101 and surrounded by insulation 1102. The top section of the reactor is filled with air, and corresponds to a substantially adiabatic section. The portion that is filled with molten salt is a non-adiabatic section. The process gas 1105 is fed into the U-shaped tube reactor that contains inert packing 1103. This section of the reactor serves to mix and preheat the feed gas. The gas makes a turn and enters a section that contains an OCM catalyst 1104. This section is non-adiabatic. The gas then moves to a section of the reactor that does not contain molten salt, and is substantially adiabatic.

In some cases, the reactor, salt bath, and other process equipment are made of materials that are compatible with molten salts. Examples include high nickel content steels (e.g., >20 mol % Ni), austentic steels, carbon steels, or nickel cladded steels. In some embodiments, the process equipment is protected by cathodic protection. A sacrificial reductant can be used. This can reduce corrosion of the reactor body. For example, magnesium, zirconium, or beryllium can be in the salt as particles or used as billets on the reactor bath interior. Any metal can be used with a standard reduction potential more negative than $Cr_{3+}/Cr$ redox couple (i.e., less than about 0.77 vs. Standard Hydrogen Electrode). In some embodiments, the bath atmosphere can be controlled. For example an inert gas can be used as a blanket. In some cases, $O_2$ and $H_2O$ are at less than about 10 ppm.

Figure 29:
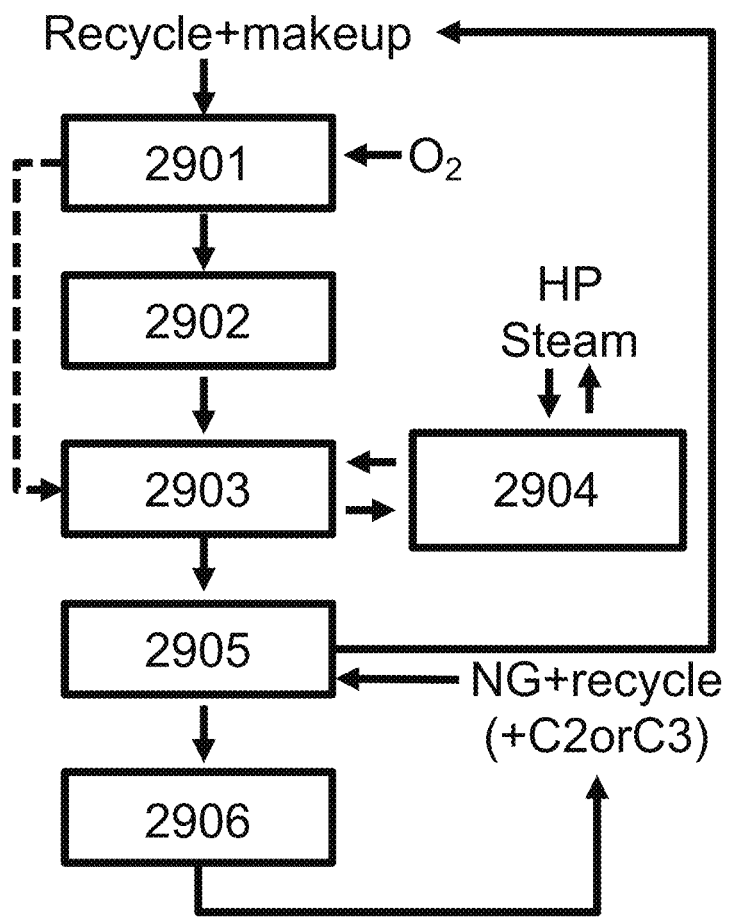
FIG. 29 shows an example of a block flow diagram of an OCM reaction system utilizing a molten salt heat exchange medium.

FIG. 29 shows an example of a block flow diagram. The natural gas inlet 2901 can contain 0-30 mol % ethane, 0-30 mol % propane, 0-30 mol % butane, 0-20 wt % light naphtha, and 8-20 mol % $O_2$. The start-up reactor 2902 can be a fired heater, for example, with an outlet temperature of less than about 800° C. The start-up reactor can be an adiabatic OCM reactor and can be bypassed after initial salt heating. The main reactor 2903 can be a reactor having an isothermal section as described herein. In some cases, it has a post-bed cracking section. The salt reservoir 2904 can be used for heat exchange, and can be used to produce high pressure (HP) steam. Heat exchangers 2905 can be used to recover heat and cool the stream. A separation module 2906 can be used to recover products or a recycle stream.

In some cases, the reactor is tubular. In some instances, the reactor does not have a constant cross sectional area.

Figure 31:
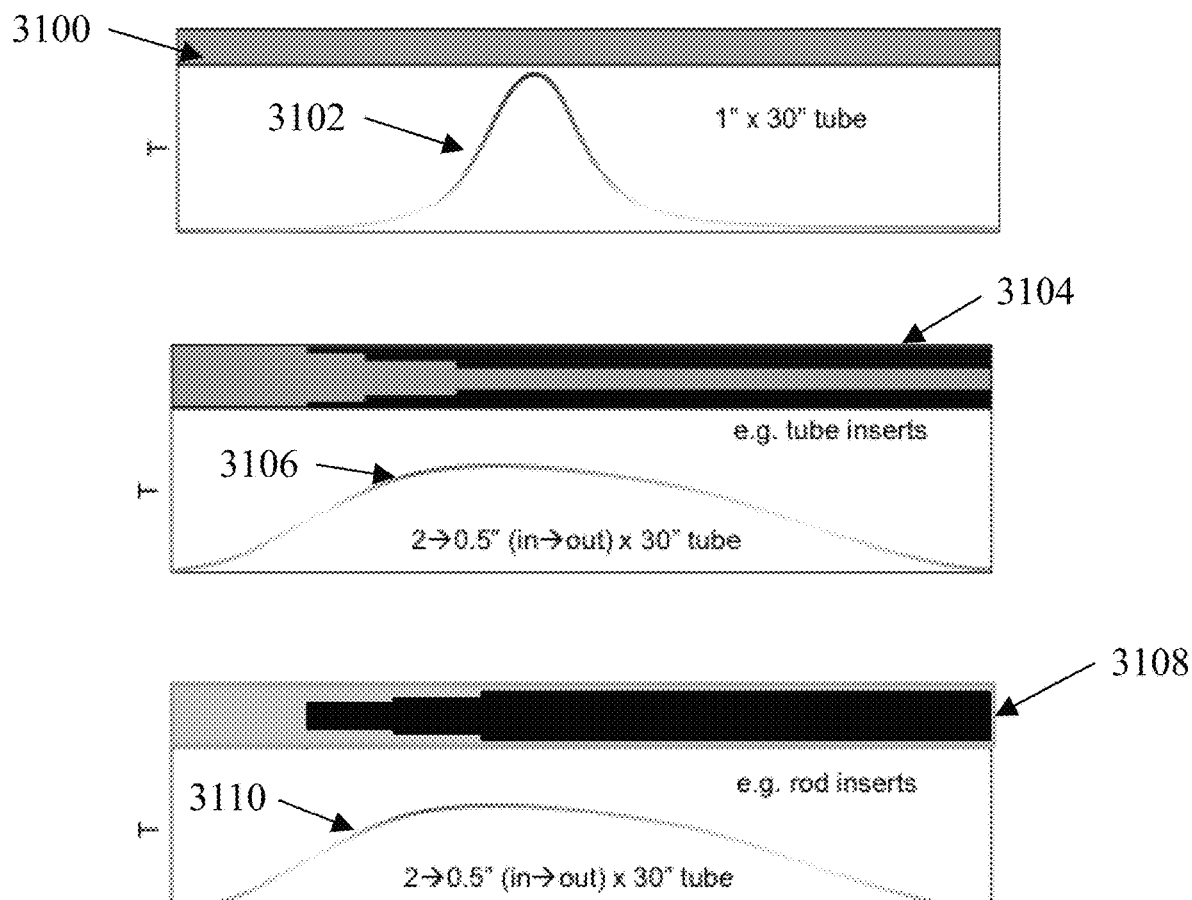
FIG. 31 shows an example of the reduction in cross section of a tubular OCM reactor resulting in a more even temperature profile.

With reference to FIG. 31, a narrowing cross section can be used to achieve a more uniform temperature profile across the reactor. For example, when the reactor is of uniform width 3100, in this case a 1 inch diameter by 30 inch length tube, the temperature has a sharp profile 3102. However, when tube inserts restrict the periphery of the tube 3104 to narrow it, the temperature profile is more flat 3106. Here, the tube starts at 2 inches and reduces to 0.5 inches, having an average diameter of 1 inch (matching 3100). The reactor diameter can also be narrowed by inserting rods in the center of the reactor 3108 to achieve a similar flat temperature profile 3110.

OCM Reactor Configurations

In some cases, it may be desirable to have an OCM system with at least about 30% capital expenditure (Capex) reduction compared to convention methods for OCM reactions. This can be achieved by doubling the ethylene yield of an OCM process. One way to achieve the target (i.e., doubling the ethylene yield) is to double the methane conversion while maintaining the same selectivity for ethylene. Since the OCM reaction may be limited by a concentration of oxidizing agents (e.g., oxygen), the methane conversion can be elevated by increasing a concentration of the oxidizing agents. In cases where an OCM feed stream comprises an increased concentration of oxidizing agents, a substantially adiabatic reactor may not be suitable for performing an OCM process due to a significant increase in heat generation during the OCM process. A tubular reactor system may be used for removing the heat generated by the OCM process such that the OCM process can be conducted using a feed having an increased concentration (relevant to a concentration used in conventional OCM processes) of oxidizing agents, which OCM processes may yield a higher methane conversion while maintaining a similar outlet temperature and/or ethylene selectivity. In some cases, the tubular reactor system is a molten salt tubular reactor system.

An OCM product gas may comprise ethane and ethylene. As discussed above and elsewhere herein, a Post Bed Cracking unit (PBC) can be utilized to convert the ethane from the OCM product gas to additional ethylene. However, in some situations, it may not be ideal to use a PBC unit in a molten salt tubular reactor system. For example, in some cases, an outlet temperature of the reactor system does not fall within a desired range (e.g., greater than or equal to about 800° C., 850° C., 900° C., 950° C. or more) and since the molten salt tubular reactor is very efficient in removing heat, once the oxidizing agent is depleted, the temperature may drop rapidly. In view of this, some aspects of the present disclosure provide alternative designs of OCM systems.

An OCM system may comprise a molten salt reactor and a substantially adiabatic reactor in fluidic and/or thermal communication with the molten salt reactor. The molten salt reactor may be configured to receive an OCM feed stream comprising an oxidizing agent (e.g., oxygen) and methane. The molten salt reactor may comprise a catalyst that may facilitate an OCM reaction. The molten salt reactor may permit at least a portion of the oxidizing agent and the methane to react in an OCM reaction with the aid of the catalyst. The OCM reaction may generate a product stream comprising higher hydrocarbons (e.g., $C_{2+}$ compounds), unreacted methane, unreacted oxidizing agent and/or impurities. The product stream may be directed into the substantially adiabatic reactor. The substantially adiabatic reactor may comprise a catalyst that may facilitate OCM reactions. The substantially adiabatic reactor may react at least a portion of the unreacted methane and oxidizing agent in an OCM reaction with the aid of the catalyst within the reactor. The OCM reaction occurred in the substantially adiabatic reactor may generate heat. The heat may increase an outlet temperature of the reactor to a predetermined value or range (e.g., greater than or equal to about 800° C., 850° C., 900° C., 950° C. or more). In some cases, an OCM system may comprise a plurality of OCM reactors. At least some of the OCM reactors may comprise multiple sections (e.g., a molten salt section and a substantially adiabatic section).

In some cases, an OCM system comprises a molten salt reactor and an oxidative dehydrogenation (ODH) reactor in fluidic and/or thermal communication with the molten salt reactor. The molten salt reactor may be configured to receive an OCM feed stream comprising an oxidizing agent (e.g., oxygen) and methane. The molten salt reactor may comprise a catalyst that may facilitate an OCM reaction. The molten salt reactor may permit at least a portion of the oxidizing agent and the methane to react in an OCM reaction with the aid of the catalyst.

The ODH reactor may comprise a catalyst. The catalyst may facilitate an ODH reaction. The ODH reactor may be configured to receive an effluent stream from the molten salt reactor. The effluent stream may comprise methane, higher hydrocarbon compounds (e.g., $C_{2+}$ compounds), unreacted oxidizing agents and/or non-$C_{2+}$ impurities (e.g., hydrogen, nitrogen, carbon monoxide and carbon dioxide). The ODH reactor may convert ethane into ethylene with the aid of a catalyst. In some cases, the ODH reactor utilizes carbon dioxide or oxygen to convert paraffins to olefins (e.g., ethane to ethylene, or propane to propylene). In cases where carbon dioxide is used to convert paraffins to olefins in an ODH reaction, the ODH reaction may yield a product stream which comprises carbon monoxide. At least a portion of the carbon monoxide generated in the ODH reaction may be directed into a methanation unit for a methanation reaction. Some or all of methane generated in the methanation reaction may be recycled to the molten salt reactor.

In some cases, an OCM system may comprise a plurality of OCM reactors. At least some of the OCM reactors may comprise multiple sections (e.g., a molten salt section and an ODH section). In some cases, an OCM system comprises a single reactor comprising a first catalyst that facilitates OCM reactions and a second catalyst that facilitates ODH reactions. The second catalyst may be downstream of the first catalyst. In some cases, an OCM system comprises an OCM reactor that facilitates both an OCM reaction and an ODH reaction. In some cases, an OCM system may comprise a catalyst which is a blend of an OCM catalyst and an ODH catalyst. In some cases, an OCM system comprises a gradient reactor that starts with 100% OCM catalysts and ends with 100% ODH catalysts.

An ODH reaction may be conducted at a temperature that is greater than or equal to about 500° C., 550° C., 600° C., 650° C., 700° C., 750° C., 800° C., 850° C., 900° C. or more. In some cases, an ODH reaction is conducted at a temperature that is less than or equal to about 1,000° C., 950° C., 900° C., 850° C., 800° C., 750° C., 700° C., 650° C., 600° C., or less. In some cases, an ODH reaction is conducted at a temperature that is between any two values described herein, for example, between about 500° C. and 900° C., or between about 600° C. and 800° C.

Various catalysts can be used in an ODH reaction (e.g., a $CO_2$ ODH reaction or a $O_2$ ODH reaction). Non-limiting examples of ODH catalysts include, $Cr_2O_3$ supported on $SiO_2$, $Al_2O_3$, $TiO_2$ or $ZrO_2$, $Cr/SO_4$—$SiO_2$, K—$Cr/SO_4$—$SiO_2$, K—Cr—Mn/$SiO_2$, Cr/H—ZSM-5, Cr/Silicalite-2, Fe—Mn/Silicalite-2, Cr—Mn/Silicalite-2, Cr—Mn—Ni/Silicalite-2, $MnO_2$, K-doped $MnO_2$, $Na_2WO_4$—Mn/$SiO_2$, $CeO_2$, Fe—Cr/$ZrO_2$, or combinations thereof.

In some aspects of the present disclosure, a system for performing oxidative coupling of methane (OCM) is provided. The system may comprise an OCM reactor. The OCM reactor may be a micro-channel OCM reactor. The OCM reactor may comprise at least one corrugated metal foil. The metal foil may comprise ridges and intervening grooves between the ridges. In some cases, the intervening grooves are between each two adjacent ridges. The grooves may be micro-channels. The micro-channels may have an average width greater than or equal to about 50 micrometers (μm), 75 μm, 100 μm, 150 μm, 200 μm, 250 μm, 300 μm, 350 μm, 400 μm, 450 μm, 500 μm, or more. In some cases, the micro-channels have an average width less than or equal to about 1,000 μm, 900 μm, 800 μm, 700 μm, 600 μm, 500 μm, 400 μm, 300 μm, 200 μm, 100 μm, or less. In some cases, the micro-channels have an average width falling between any of the two values described herein, for example, between about 200 μm and about 500 μm.

The OCM reactor may also comprise a catalyst that may facilitate an OCM reaction. The catalyst may be disposed within the grooves of the metal foil. In some cases, the OCM reactor comprises a plurality of the corrugated metal plates or foils (e.g., greater than or equal to about 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500 or more). Some or all of the metal foils may be assembled in stacks. At least a portion of the metal foils (e.g., greater than or equal to about 5%, 10%, 20%, 30%, 40%, 50%, 60%, 70%, 80%, 90%, 95%, or more) may comprise perforations. The perforations may create passageways between the metal foils. The perforations may be made in selected areas of the metal foil by cutting or pressing on die. The metal foils may comprise active areas (or zones). The catalyst may be disposed in the active areas only. The OCM reaction may be conducted in the active areas.

In some cases, the system comprises a flow through component. The flow through component may be integrated with an OCM reactor. The flow through component may be a part of an OCM reactor. The flow through component may enable a low velocity operation with large surface area for process gas to enter the catalyst bed of the OCM reactor. In some cases, the velocity is less than or equal to about 3 m/s, 2 m/s, 1 m/s, 0.9 m/s, 0.8 m/s, 0.7 m/s, 0.6 m/s, 0.5 m/s, 0.4 m/s, 0.3 m/s, 0.2 m/s, 0.1 m/s, 0.09 m/s, 0.08 m/s, 0.07 m/s, 0.06 m/s. 0.05 m/s, 0.04 m/s, 0.03 m/s, 0.02 m/s, 0.01 m/s, or less. In some cases, the velocity is between any of the two values described herein, for example, between about 0.05 m/s and about 0.3 m/s.

In some cases, the system comprises a manifold design in fluidic communication with the OCM reactor. The manifold may be used for gas distribution. Layer(s) of thermal isolation material may be used in inlet gas distribution manifold or on a side of catalyst pack bed assembly so as to provide a feed gas with a homogeneous temperature across the catalyst pack bed assembly.

Figure 37:
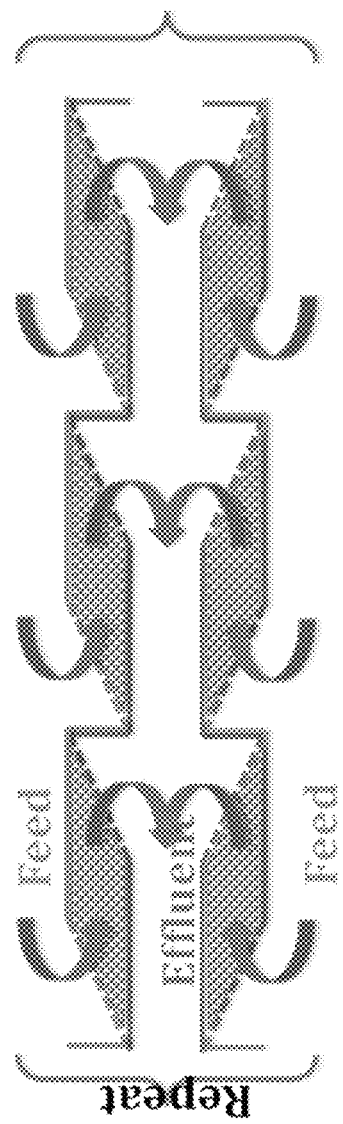
FIG. 37 shows an example OCM reactor comprising two catalyst assembly stacks with perforations for feed inlet and product outlet.
Figure 38:
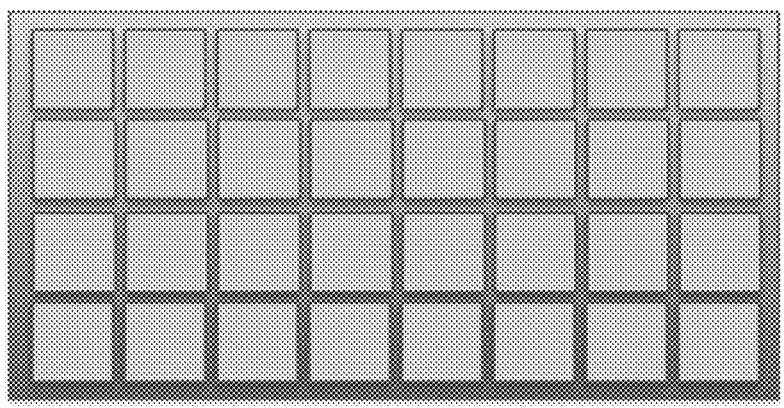
FIG. 38 shows an example OCM reactor comprising a metal sheet having multiple active zones.

FIGS. 37 and 38 show example of micro-channel OCM reactors. FIG. 37 shows a side view of a set of two catalyst assembly stacks comprising offset perforations for feed inlet and product outlet. Small dots comprised in each sheet represent packed catalyst particles. In FIG. 38, an OCM reactor may comprise a metal plate comprising multiple active zones (e.g., 32 squares in the figure). Remaining areas in the plate may be used for feed conditioning or distribution. The feed flow path in such areas (i.e., the remaining areas) may be designed with race tracks so as to provide sufficient heat exchange to obtain substantially the same temperature in each active zone. The different zones may be created in the same plate (or sheet) through stamping different corrugation patterns and perforations. Some or all of the zones may be used to conduct the same or different reactions. In some cases, feed and product gas are put in thermal contact to minimize the need to pre-heating the feed prior to the reaction.

Dilution of Feed for Increased Methane Conversion

Another aspect of the present disclosure is to provide a method for improving methane conversion in an oxidative coupling of methane process using a diluent. A diluent, such as water ($H_2O$), carbon dioxide ($CO_2$), or combinations thereof, can absorb energy during an exothermic oxidative coupling of methane reaction, and can provide energy during an endothermic cracking operation. Further, a diluent can be used to reduce the concentration of oxygen ($O_2$) in a feed stream, which can improve the durability of an apparatus that is used to inject a source containing oxygen ($O_2$). The oxygen and the diluent can be pre-mixed before adding to a reactor, and a pre-mixed oxygen and diluent stream can be added to a reactor downstream of where a stream containing methane is injected.

In another aspect of the present disclosure, provided herein is a method for producing an olefin. The method can comprise producing a gas stream comprising methane ($CH_4$), oxygen ($O_2$), and a diluent and passing the gas stream over an oxidative coupling of methane (OCM) catalyst at a pressure of at least about 2 bar(g) to convert at least some of the $CH_4$ into $C_{2+}$ compounds, wherein a ratio of diluent molecules to carbon atoms in the gas stream is at least about 0.1.

The diluent can comprise water ($H_2O$) and/or carbon dioxide ($CO_2$).

The ratio of diluent molecules to carbon atoms in the gas stream can be any suitable value. In some cases, the ratio of diluent molecules to carbon atoms in the gas stream is at least about 0.01, at least about 0.05, at least about 0.1, at least about 0.5, at least about 1, at least about 5, at least about 10, or at least about 20. In some cases, the ratio of diluent molecules to carbon atoms in the gas stream is at most about 0.01, at most about 0.05, at most about 0.1, at most about 0.5, at most about 1, at most about 5, at most about 10, or at most about 20. The ratio of diluent molecules to carbon atoms in the gas stream can be between about 0.1 and about 5.

The pressure can be greater than or equal to about 4 bar(g), 5 bar(g), 6 bar(g), 7 bar(g), 8 bar(g), 9 bar(g), 10 bar(g), or more in some cases.

Figure 12:
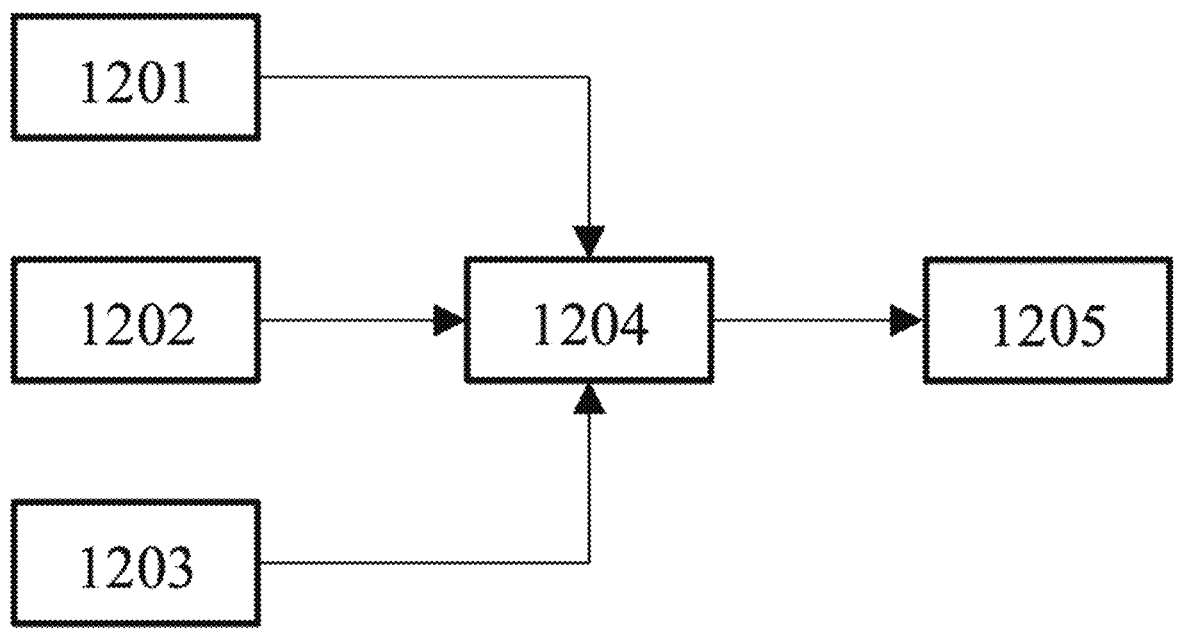
FIG. 12 shows an oxidative coupling of methane system using a diluent.

FIG. 12 shows an oxidative coupling of methane process using a diluent stream 1200. A stream containing oxygen 1201, a stream containing methane 1202, and a stream containing a diluent 1203 are injected into a reactor containing an oxidative coupling of methane catalyst 1204. The effluent of the reactor is then injected into a post bed cracking unit 1205 that does not contain an oxidative coupling of methane catalyst.

The stream containing oxygen can be the same as the stream containing methane, or the stream containing oxygen can be the same as the stream containing the diluent.

The diluent can be water ($H_2O$), carbon dioxide ($CO_2$), or combinations thereof.

The fraction of gas that is injected into the reactor that is a diluent may be greater than or equal to about 5%, 10%, 20%, 25%, 30%, 35%, 40%, 45%, 50% (mol %), or more.

The temperature of effluent gas at the exit of the reactor containing an oxidative coupling of methane effluent may be at least about 600° C., at least about 650° C., at least about 700° C., at least about 750° C., at least about 800° C., at least about 850° C., at least about 900° C., or at least about 950° C.

The conversion of methane in the reactor containing an oxidative coupling of methane catalyst may be at least about 5%, at least about 7%, at least about 8%, at least about 9%, at least about 10%, at least about 11%, at least about 12%, at least about 13%, at least about 14%, or at least about 15%.

Within the post-bed cracking unit, ethane can be dehydrogenated and converted into ethylene. A source containing ethane can be added to the post-bed packing unit downstream of the reactor containing an oxidative coupling of methane catalyst.

The post-bed cracking unit and the reactor containing an oxidative coupling of methane catalyst can be contained within the same vessel.

The ratio of ethylene to ethane at the outlet of the post-bed cracking unit may be at least about 1:1, at least about 1.5:1, at least about 2:1, at least about 2.5:1, at least about 3:1, at least about 3.5:1, at least about 4:1, at least about 4.5:1, or at least about 5:1.

A stream containing ethane can optionally be added to the reactor containing an oxidative coupling of methane catalyst. A stream containing ethane can optionally be added to the post-bed cracking unit.

Figure 13:
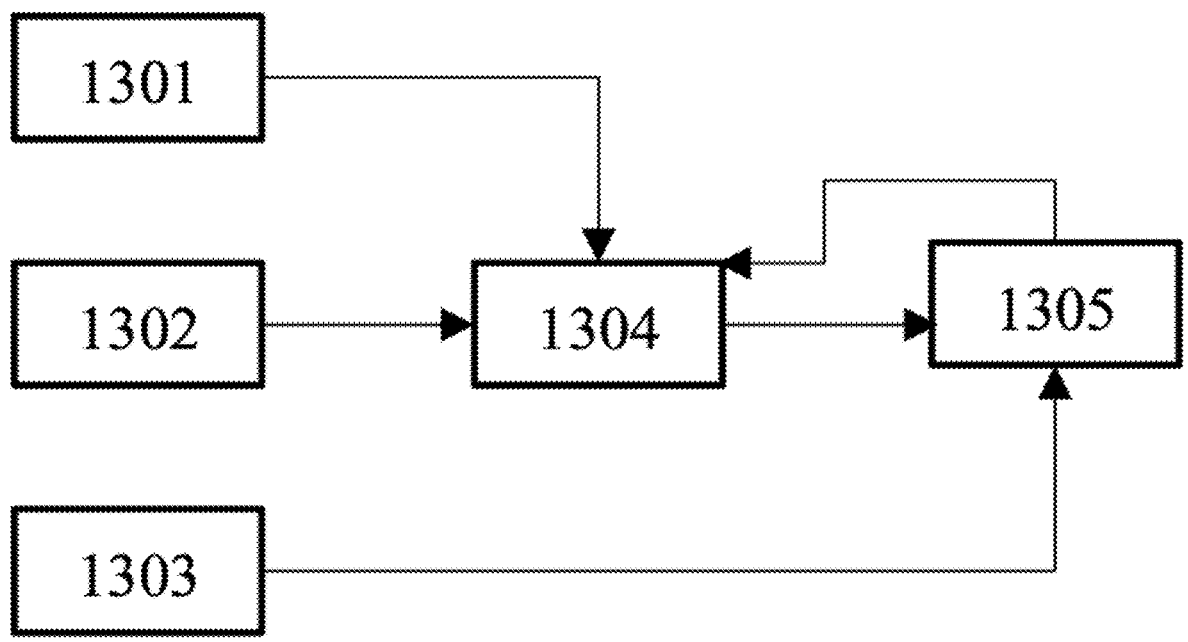
FIG. 13 shows an oxidative coupling of methane system using a steam diluent that is heated in an oxidative coupling of methane reactor.

FIG. 13 shows an oxidative coupling of methane system using a steam diluent that is heated in an oxidative coupling of methane reactor 1300. A source containing oxygen ($O_2$) 1301 and a source containing methane 1302 are injected into a reactor containing an oxidative coupling of methane catalyst 1304 to produce a hot OCM gas. The hot OCM gas is put into thermal contact with a stream containing water 1303 within a heat exchanger 1305 to produce a steam stream. The steam stream is then injected into the oxidative coupling of methane reactor 1304. The steam stream can be used as a diluent.

The heat exchanger can be integrated with the oxidative coupling of methane reactor as an integrated non-adiabatic reactor.

The effluent of the oxidative coupling of methane reactor can then be injected into a post-bed reactor. The post bed reactor can be in the same vessel as the oxidative coupling of methane reactor. The post bed reactor can be in the same vessel as the heat exchanger.

Figure 14:
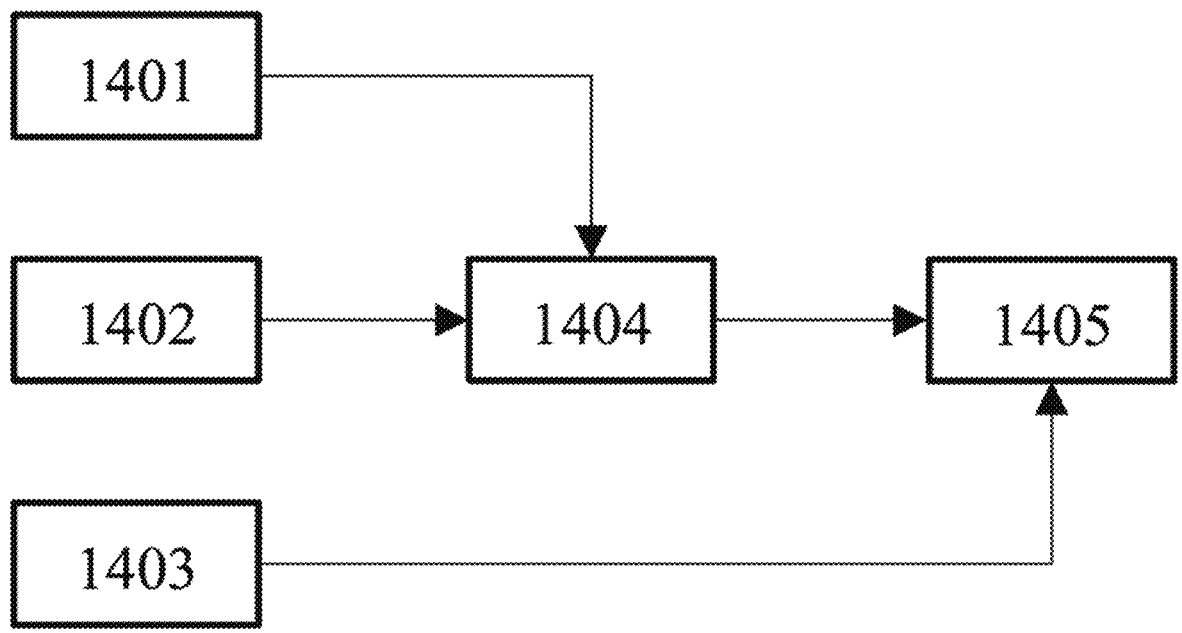
FIG. 14 shows an oxidative coupling of methane system that mixes oxygen with a diluent prior to injection in an oxidative coupling of methane reactor.

FIG. 14 shows an oxidative coupling of methane system that mixes oxygen with a diluent prior to injection in an oxidative coupling of methane reactor 1400. A stream containing oxygen 1401 and a stream containing a diluent 1402 are pre-mixed in a mixer 1404 to produce a diluted oxygen stream. The diluted oxygen stream and a stream containing methane 1403 are injected into an oxidative coupling of methane reactor 1405.

Figure 15:
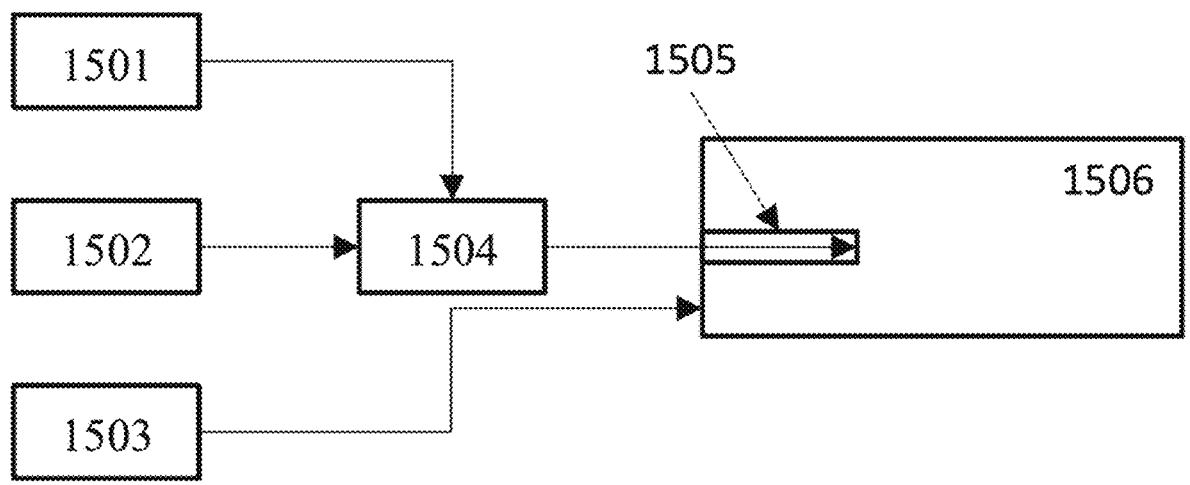
FIG. 15 shows an oxidative coupling of methane system in which oxygen and a diluent are added downstream of methane.

FIG. 15 shows an oxidative coupling of methane system in which oxygen and a diluent are added downstream of methane 1500. A stream containing oxygen 1501 and a stream containing a diluent 1502 are pre-mixed in a mixer to produce a pre-mixed oxygen stream. A stream containing methane is injected into an oxidative coupling of methane reactor 1506. The pre-mixed oxygen stream is injected downstream of the stream containing methane using an injector 1505 that extends into the oxidative coupling of methane reactor 1506. The injector can be a diffuser tube.

Ethane Injection

Utilization of ethane to produce olefins in combination with OCM can be advantageous as it can lead to an increased production rates and concentrations of the desired product for a fixed size reactor. The capital intensity of the integrated process can be reduced by as much as 30% with addition of ethane in front of the OCM catalytic bed and/or in the reactor back end (referred to as post-bed cracking section).

Described herein is an improvement in utilization of ethane. The methods described herein for introducing ethane in the process can result in an incremental capex intensity reduction of at least about 10%. The method described herein can also be integrated with high yield OCM fix bed reactors using molten salt as described herein. In some cases, ethane conversion in this type of reactor is more constraint due to reduced $CH_4$ plant traffic. The methods described herein involve moving the point at which ethane is mixed in the process from before the entrance to the OCM catalytic bed (or pre-OCM reactor) to now injecting ethane directly within the OCM catalyst bed. In some cases, the method includes propane injection.

The amount of ethane added can also be increased. With front-end injection, the amount of ethane is typically between about 3% to about 5% ethane. With the in-bed injection described herein, about 3% to 15% ethane can be used. Percentages are of injected ethane compared to the total process stream molar flow.

In some cases, the most desirable place to inject ethane into the OCM catalyst bed is at an axial location where the OCM catalyst bed is at temperature above 700° C. and bellow 900° C., preferably above 750° C. and below 850° C. In some cases, some unreacted $O_2$ remains in the OCM process stream to enable some oxidative conversion of ethane to ethylene. In some cases, it is undesirable to have ethane in contact with the OCM catalyst at a temperature of less than about 650° C.

This ethane to ethylene conversion can be the result of a combination of direct oxidative dehydrogenation of ethane, methyl radical attack of ethane or thermal cracking.

One of the main features of this process is that it is not endothermic, therefore the amount of ethane added is not limited by the heat capacity of the effluent into which ethane is added. In some cases, PBC ethane processing capacity is limited by heat capacity.

Another important feature is that injected ethane is not in contact with OCM catalyst operated at modest temperature in the range of 450° C. to 700° C. where ODH selectivity is poor. In some cases, part of the mixed $O_2$+methane+ethane stream can be bypassed to minimize ethane loss to combustion.

In some embodiments, oxygen can be added to the ethane containing stream with or without another gas (e.g., steam, $N_2$, methane, $CO_2$) injected into the bed. In some cases, this enables greater control of the $O_2$ partial pressure at the point of ethane injection and decouple control of the $O_2$ concentration profile through the OCM catalyst bed for the main process stream. In some cases, the in bed added stream contains propane. In some cases, higher hydrocarbons are mixed into the stream.

In some instances, the multiple injection points are used add the added higher alkane stream is rapidly switched between these locations resulting in temperature oscillation of the solids in the packed bed. These injection points may be in the same plane relative to the flow direction or staggered, resulting in injection with different level of $O_2$ and different bed temperature to be combined.

Figure 16:
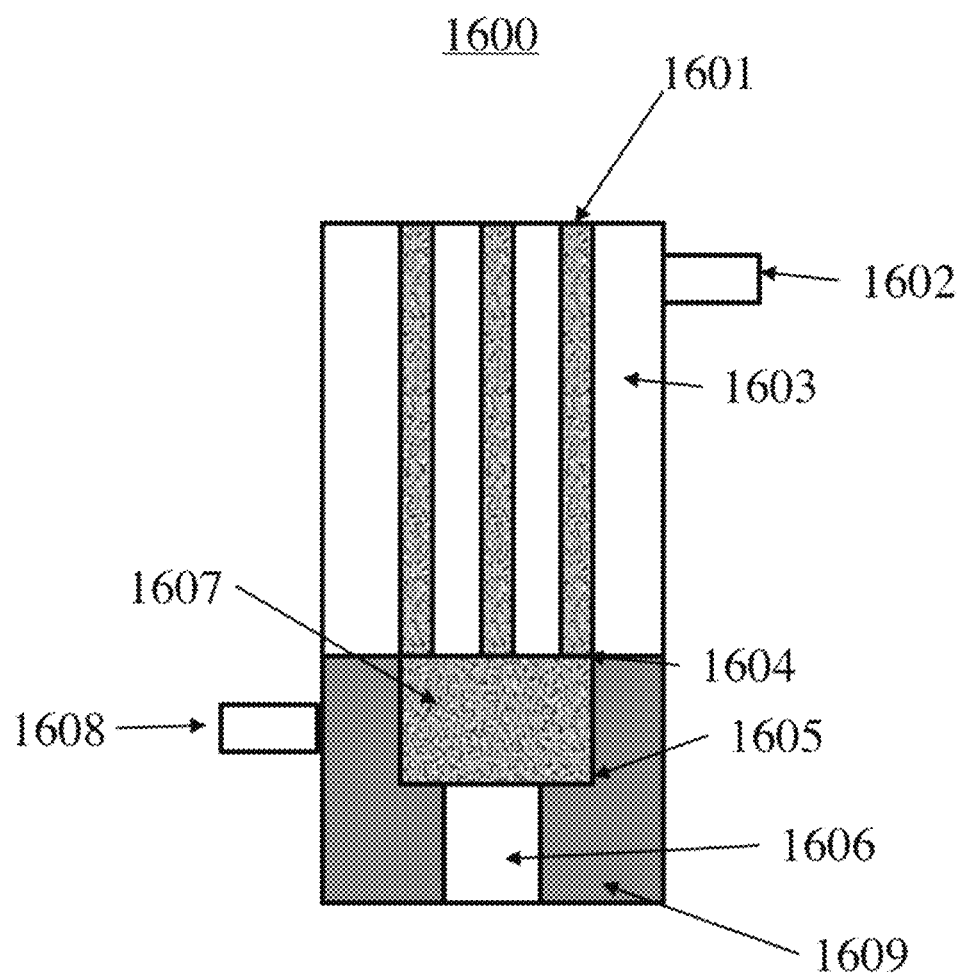
FIG. 16 shows an oxidative coupling of methane system that comprises multiple ethane injection locations.

FIG. 16 shows an oxidative coupling of methane system that includes multiple ethane injection points 1600. Methane and oxygen can be injected into tubes at the top of the reactor 1601 which are a section of the reactor that is non-adiabatic and in contact with a heat transfer medium. A heat transfer medium (e.g. molten salt) is injected near the top of the reactor 1602 and flows down the shell side of the reactor 1603, absorbing heat from the oxidative coupling of methane reaction taking place in the tubes and finally flowing out of the reactor at an elevated temperature 1608. In between the non-adiabatic tubes and the substantially adiabatic section that includes an oxidative coupling of methane catalyst 1607, ethane can be injected 1604. An additional injection of ethane can be made in between the non-adiabatic section that contains an oxidative coupling of methane catalyst and a non-adiabatic section that does not contain an oxidative coupling of methane catalyst 1605. The non-adiabatic section that does not contain an oxidative coupling of methane catalyst can serve as a post-bed cracking unit 1606. The non-adiabatic sections are surrounded by an insulating material 1609.

The temperature of the heat transfer medium at the inlet of the reactor can be less than about 650° C., less than about 600° C., less than about 550° C., less than about 500° C., less than about 450° C., less than about 400° C., less than about 350° C., or less than about 300° C.

The temperature in between the non-adiabatic section that is in thermal communication with a heat transfer medium and the substantially adiabatic section can be at least about 600° C., at least about 650° C., at least about 700° C., at least about 750° C., at least about 800° C., at least about 850° C., at least about 900° C., or at least about 950° C.

The temperature at the outlet of the substantially adiabatic section that contains an oxidative coupling of methane catalyst may be at least about 700° C., at least about 750° C., at least about 800° C., at least about 850° C., at least about 900° C., at least about 950° C., or at least about 1000° C.

The temperature of the gas at the entrance of the non-adiabatic section that is in thermal communication with a heat transfer medium may be at least about 400° C., at least about 450° C., at least about 480° C., or at least about 500° C.

The gas at the entrance of the non-adiabatic section that is in thermal communication with a heat transfer medium may optionally include ethane. The concentration of ethane at the entrance of the non-adiabatic section that is in thermal communication with a heat transfer medium may be greater than or equal to about 0.1%, 0.2%, 0.3%, 0.4%, 0.5%, 0.6%, 0.7%, 0.8%, 0.9%, 1.0% (mol %), or more.

The concentration of ethane after ethane injection into the substantially adiabatic section that contains an oxidative coupling of methane catalyst may be greater than or equal to about 1%, 2%, 3%, 4%, 5% (mol %), or more.

The concentration of ethane after ethane injection into the substantially adiabatic section that does not contain an oxidative coupling of methane catalyst may be greater than or equal to about 1%, 2%, 3%, 4%, 5%, 6%, 7%, 8%, 9%, 10% (mol %), or more.

The temperature of the heat transfer medium at the outlet of the reactor may be at least about 600° C., at least about 650° C., at least about 700° C., at least about 750° C., at least about 800° C., at least about 850° C., at least about 900° C., at least about 950° C., or at least about 1000° C.

Alkane Conversion Process and Systems

The thermal cracking of alkanes, including ethane and propane, has been practiced in order to produce olefins, which is a basic feedstock of the petrochemical industry.

Olefins, including ethylene and propylene, are important feedstocks in the chemicals industry. In an olefin production process, steam cracking or pyrolysis of ethane or naphtha at high temperatures may be conducted to yield a mixture of products with modest conversions of alkane.

Recognized herein is the need for efficient and commercially viable olefin production systems and methods for converting alkanes into olefins.

The present disclosure provides systems and methods for generating olefins. In some embodiments, a process for generating olefins comprises converting alkanes into a mixture comprising olefins using an oxidizing agent (e.g., oxygen ($O_2$)) and a radical transfer agent, and waiting for a time period which is greater than the auto-ignition delay time (AIDT). In some cases, the mixture is cooled. This approach may be used to increase the olefin yield through repeating the process of addition of the oxidizing agent and, in some cases, heat removal. The amount of oxygen containing species produced, including CO and $CO_2$ ("$CO_x$"), can be minimized through the addition of a minimal amount of the oxidizing agent (e.g., $O_2$) relative to the amount of alkane being converted.

An aspect of the present disclosure provides methods for forming an olefin from a mixture of alkane, oxygen ($O_2$), and radical transfer agent within a reactor. The transformation of alkane to olefin within the reactor can proceed through the formation free alkyl radical species (e.g. an ethyl radical, $H_3C\cdot$), that can later proceed to an olefin molecule. The free alkyl radical species can be generated from the combination of an alkane species with oxygen ($O_2$) and a radical transfer agent. The radical transfer agent can intermediate the transformation of an alkane to an olefin. The radical transfer agent can be derived from any molecule that can be radicalized, e.g. $H_2$, water ($H_2O$), and methane ($CH_4$), or any combination thereof. The radical transfer agent species can then form transient free radicals during the reaction, including hydroxyl radical (HO·), methyl radical ($H_3C\cdot$), hydrogen radical (H·), or any combination thereof. The selectivity for any individual alkane species (e.g., $C_2H_6$) to be radicalized over another individual alkane species (e.g., $CH_4$) can be about proportional to the relative concentrations of the two individual alkane species.

Figure 18:
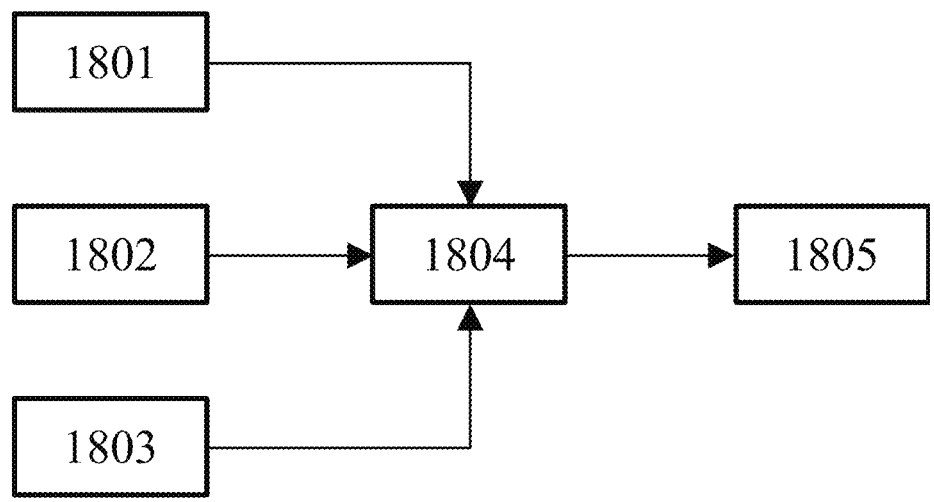
FIG. 18 shows a combination of alkane, radical transfer agent, and $O_2$ to generate olefin.

FIG. 18 shows a process for generating olefins 1800, as may be employed for use with methods (or processes) and systems of the present disclosure. The process 1800 includes a source of alkane 1801, a source of radical transfer agent 1802, a source of oxygen ($O_2$) 1803, at least one reactor 1804, and in some cases a cooling system 1805. Inputs and outputs into respective units are indicated by arrows. The source of alkane can be a natural gas source that includes $C_{2+}$ compounds and in some cases non $C_{2+}$ impurities. The source of alkane can include the effluent from an oxidative coupling of methane process. The source of alkane can be a stream emanating from one or more separation units which separate alkane from any non-alkane components. The source of radical transfer agent can include a natural gas feed stream comprising $CH_4$ and in some cases $C_{2+}$ compounds and non $C_{2+}$ impurities. The source of radical transfer agent can include the effluent from an oxidative coupling of methane process. The source of radical transfer agent can include a source of water ($H_2O$). The source of radical transfer agent can include a source of hydrogen ($H_2$). The source of radical transfer agent can be the same as the source of alkane, which can also be the source of oxygen ($O_2$).

During use, alkane from the source of alkane 1801, and radical transfer agent from the source of radical transfer agent 1802, and oxygen ($O_2$) from the source of oxygen ($O_2$) 1804 can be directed into the reactor unit 1804, which reacts the alkane with $O_2$. This reaction mixture can be held for a time that is greater than the auto-ignition delay time (AIDT), and then exit the reactor 1804. The composition of the gas exiting the reactor can then contain a greater fraction of olefin than the gas entering the reactor. The gas exiting the reactor can then be cooled in a cooling unit 1805.

The at least one reactor can be operated under about adiabatic conditions, wherein heat removal from the reactor is minimized.

The at least one reactor can be operated under about isothermal conditions, wherein heat is removed from the bed by some heat transfer medium.

The temperature of the stream or streams entering the reactor can be less than about 600° C., less than about 550° C., less than about 500° C., less than about 450° C., less than about 400° C., less than about 350° C., or less than about 300° C. The temperature of the gas exiting the reactor can be greater than about 600° C., greater than about 650° C., greater than about 700° C., greater than about 750° C., greater than about 800° C., greater than about 850° C., greater than about 900° C., greater than about 950° C., greater than about 1000° C., greater than about 1050° C., or greater than about 1100° C. The reaction can generate additional components, including CO and $CO_2$.

The pressure in the reactor can be at least about 0 bar (g), at least about 1 bar(g), at least about 2 bar(g), at least about 3 bar(g), at least about 4 bar(g), at least about 5 bar(g), at least about 6 bar(g), at least about 7 bar(g), at least about 8 bar(g), at least about 9 bar(g), at least about 10 bar(g), at least about 11 bar(g), at least about 12 bar(g), at least about 13 bar(g), at least about 14 bar(g), at least about 15 bar(g), at least about 16 bar(g), at least about 17 bar(g), at least about 18 bar(g), at least about 19 bar(g), at least about 20 bar(g), at least about 25 bar(g), at least about 30 bar(g), at least about 35 bar(g), or at least about 40 bar(g).

The apparent selectivity in the reactor can be at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 100%, at least about 110%, or at least about 120%.

The carbon efficiency in the reactor can be at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%.

Once the radical transfer agent, oxygen ($O_2$), and alkane are mixed within the reactor, the species can be held for a time that is greater than the auto-ignition delay time (AIDT). The AIDT can be at least about 1 millisecond (ms), at least about 2 milliseconds (ms), at least about 3 milliseconds (ms), at least about 5 milliseconds (ms), at least about 10 milliseconds (ms), at least about 15 milliseconds (ms), at least about 20 milliseconds (ms), at least about 30 milliseconds (ms), at least about 40 milliseconds (ms), at least about 50 milliseconds (ms), at least about 75 milliseconds (ms), at least about 100 milliseconds (ms), or at least about 200 milliseconds (ms).

Figure 19:
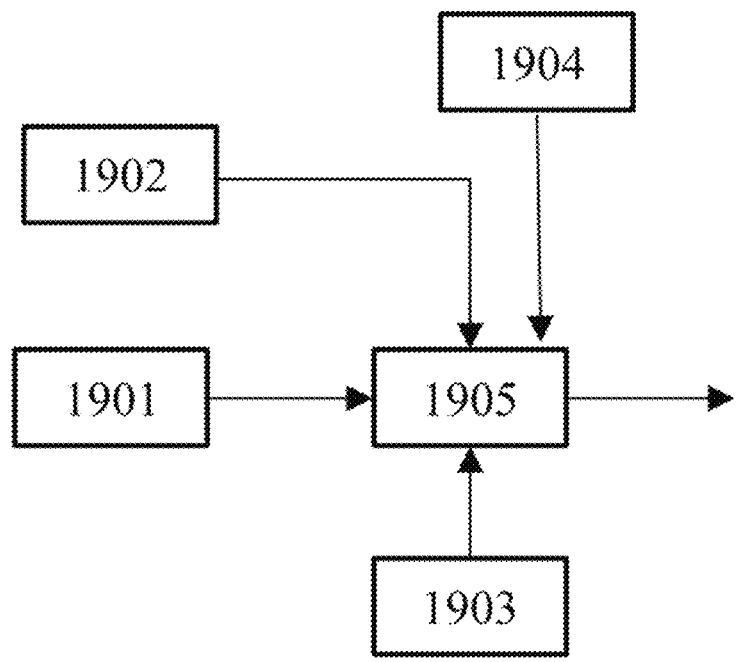
FIG. 19 shows a system for increasing olefin concentrations in the cooled effluent gas by converting additional alkane.

FIG. 19 shows a process 1900, which includes a stream that is the effluent of a process to generate olefin 1901 (e.g., an OCM process), a source of alkane 1902, a source of O$_2$ 1903, a source of radical transfer agent 1904, and at least one reactor 1905.

The stream that is the effluent of a process to generate olefin can be from an oxidative coupling of methane (OCM) process. The stream that is the effluent of a process to generate olefin can be from an ethane cracking process. The stream that is the effluent of a process to generate olefin can be from a naphtha cracking process. An oxidative coupling of methane (OCM) process can include the conversion of methane (CH$_4$) into C$_{2+}$ products. Examples of the oxidative coupling of methane (OCM) process can be found in U.S. Patent Publication No. 2012/0041246, U.S. Pat. Nos. 9,751,079, and 9,352,295, each of which is incorporated herein by reference in its entirety. The oxidative coupling of methane (OCM) process can include an oxidative coupling of methane (OCM) catalyst. Examples of OCM catalysts can be found in U.S. Patent Publication No. 2012/0041246, U.S. Pat. No. 8,921,256, 9,956,544 or 9,751,079, each of which is incorporated herein by reference in its entirety.

The stream that is the effluent of a process to generate olefin 1901 can contain a radical transfer agent. In some cases, the percentage of the stream that is radical transfer agent is greater than or equal to about 1%, 2%, 5%, 10%, 20%, 30%, 40%, 50%, 60%, 70%, 80%, 90%, 95% (mol %), or more. In some cases, the stream that is the effluent of a process to generate olefin 1901 can contain alkane. In some cases, the percentage of the stream that is alkane is greater than or equal to about 1%, 2%, 5%, 10%, 20%, 30%, 40%, 50%, 60%, 70%, 80%, 90%, 95% (mol %), or more.

In some cases, the stream that is the effluent of a process to generate olefin 1901 can contain O$_2$. In some cases, the percentage of the stream that is O$_2$ is less than or equal to about 50%, 40%, 30%, 20%, 10%, 9%, 8%, 7%, 6%, 5%, 4%, 3%, 2%, 1%, 0.5%, 0.1% (mol %) or less. The amount of oxygen in stream can be a small amount relative to the amount of the alkane and/or the radical transfer agent. In some cases, the ratio of oxygen to alkane and/or radical transfer agent is less than or equal to about 0.5, 0.3, 0.1, 0.05, 0.01, 0.001 or less.

In some cases, the stream that is the effluent of a process to generate olefin 1901 also serves as the source of alkane 1902. In some instances, the stream that is the effluent of a process to generate olefin 1901 also serves as the source of O$_2$ 1903. In some embodiments, the stream that is the effluent of a process to generate olefin 1901 also serves as the source of radical transfer agent 1904.

Figure 20:
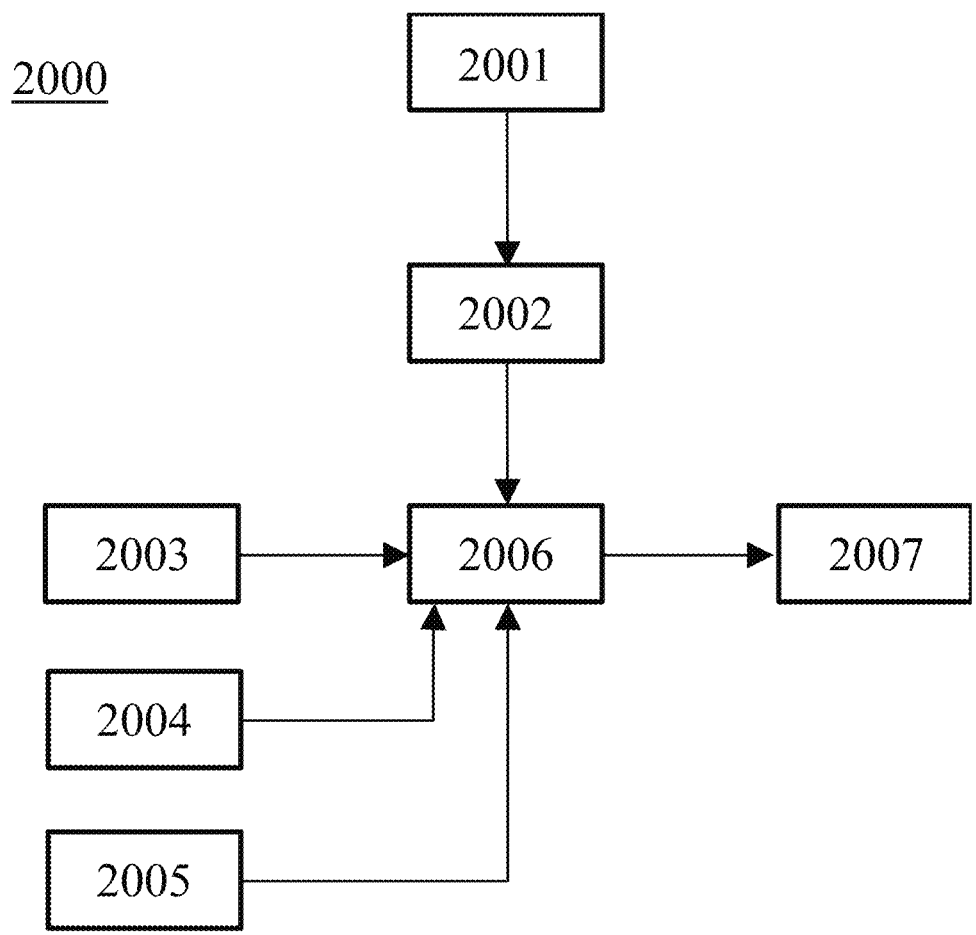
FIG. 20 shows a system for increasing olefin concentrations in the effluent gas of an oxidative coupling of methane (OCM) process.

FIG. 20 shows a system for increasing the concentration of olefin in an oxidative coupling of methane effluent 2000, which includes a source of oxidative coupling of methane effluent 2001, a cooling unit 2002, a source of alkane 2003, a source of O$_2$ 2004, a source of radical transfer agent 2005. The system may include a cooling unit 2006.

The source of oxidative coupling of methane effluent 2001 can contain a radical transfer agent. In some cases, the percentage of the stream that is radical transfer agent is greater than or equal to about 1%, 2%, 5%, 10%, 20%, 30%, 40%, 50%, 60%, 70%, 80%, 90%, 95% (mol %), or more. The source of oxidative coupling of methane effluent 2001 can contain alkane. In some cases, the percentage of the stream that is alkane is greater than or equal to about 1%, 2%, 5%, 10%, 20%, 30%, 40%, 50%, 60%, 70%, 80%, 90%, 95% (mol %), or more. The source of oxidative coupling of methane effluent 2001 can contain O$_2$. In some cases, the percentage of the stream that is O$_2$ is less than or equal to about 50%, 40%, 30%, 20%, 10%, 9%, 8%, 7%, 6%, 5%, 4%, 3%, 2%, 1%, 0.5%, 0.1% (mol %), or less. The amount of oxygen in stream can be a small amount relative to the amount of the alkane and/or the radical transfer agent. In some cases, the ratio of oxygen to alkane and/or radical transfer agent is less than or equal to about 0.5, 0.3, 0.1, 0.05, 0.01, 0.001 or less.

In some cases, the source of oxidative coupling of methane effluent 2001 also serves as the source of alkane 2002. In some cases, the source of oxidative coupling of methane effluent 2001 also serves as the source of O$_2$ 2002. In some cases, the source of oxidative coupling of methane effluent 2001 also serves as the source of radical transfer agent 2002.

In some cases, the product of the cooling operation 2007 is the same as the source of oxidative coupling of methane effluent 2001.

Figure 21:
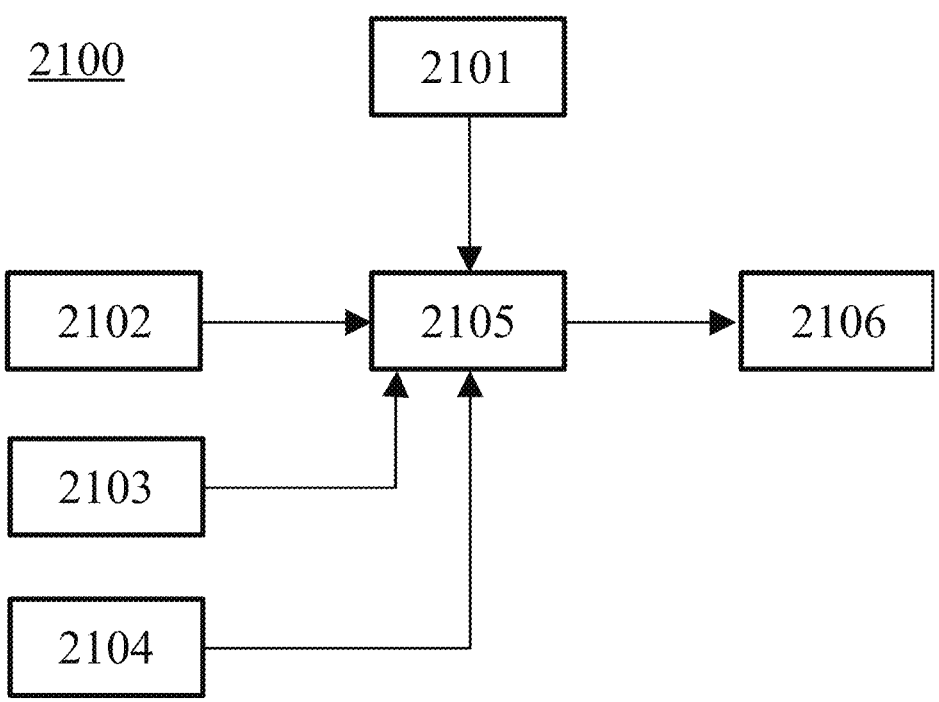
FIG. 21 shows a system for using a steam superheater as a radical transfer agent source in olefin production.

FIG. 21 shows a system for using a steam superheater as a radical transfer agent source in olefin production 2100, which includes a steam superheater 2101, a source of alkane 2102, a source of O$_2$ 2103, a source of radical transfer agent 2104, and at least one reactor 2105. In some cases, the system includes a cooling unit 2106.

The steam super heater source 2101 can also be the source of radical transfer agent 2104. The source of alkane 2102 can be the effluent of an oxidative coupling of methane process. The effluent of the cooling unit 2106 can also be the source of alkane 2102. The effluent of the cooling unit 2106 can also be the radical transfer agent 2104.

Figure 22:
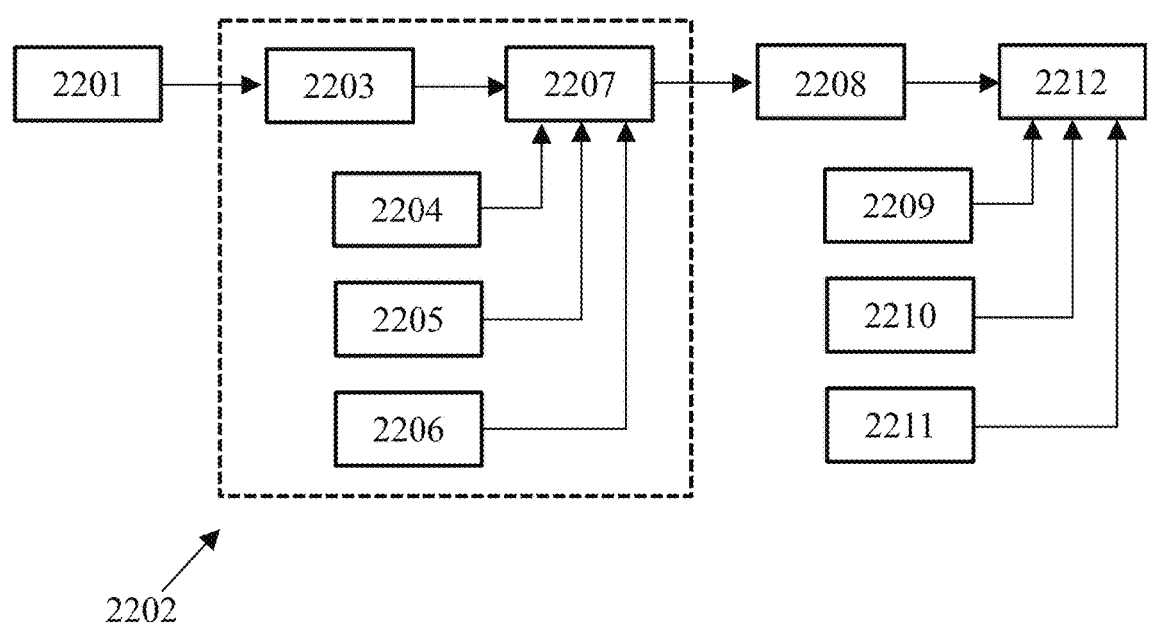
FIG. 22 shows a modular system for increasing olefin concentrations in an effluent stream.

FIG. 22 shows a modular system for increasing the olefin concentration in an effluent stream 2200, which includes a source of oxidative coupling of methane effluent 2201, and a modular system for increasing olefin concentration 2202, a cooling unit 2208, a source of alkane 2209, a source of O$_2$ 2210, a source of radical transfer agent 2211, at least one reactor 2212. In some cases, the cooling unit 2208 is precluded. The modular system for increasing olefin concentration 2202 can be comprised of an cooling unit 2203, a source of alkane 2204, a source of O$_2$ 2205, a source of radical transfer agent 2206, at least one reactor 2207.

The modular system for increasing olefin concentration 2202 can be repeated at least 1, at least 2, at least 3, at least 4, at least 5, at least 6, at least 7, at least 8, at least 9, at least 10, at least 11, at least 12, at least 13, at least 14, at least 15, at least 20, at least 30 times or more.

Figure 23:
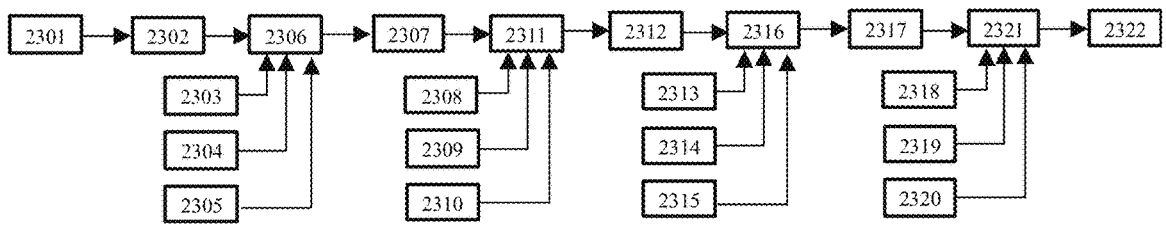
FIG. 23 shows a staged system for increasing olefin concentrations in an effluent stream.

FIG. 23 shows a system for increasing the olefin concentration in an effluent stream 2300, which includes a source of oxidative coupling of methane effluent 2301, a cooling unit 2302, a source of alkane 2303, a source of O$_2$ 2304, a source of radical transfer agent 2305, at least one reactor 2306, a cooling unit 2307, a source of alkane 2308, a source of O$_2$ 2309, a source of radical transfer agent 2310, at least one reactor 2311, a cooling unit 2312, a source of alkane 2313, a source of O$_2$ 2314, a source of radical transfer agent 2315, at least one reactor 2316, a cooling unit 2317, a source of alkane 2318, a source of O$_2$ 2319, a source of radical transfer agent 2320, and at least one reactor 2321. In some cases, the system includes a cooling unit 2322.

The system 2300 is an illustrative example of system 2200 which in a case that includes three modular systems for increasing olefin concentration in the effluent stream 2202.

The systems and methods provided herein can be performed in some cases without a radicalization initiator. In some embodiments, the reactor (e.g., 1804 in FIG. 18) contains a radicalization initiator (i.e., any material which promotes radicalization of the radical transfer agent and/or production of olefins). Catalysts can serve as radical initiation inhibitors. OCM catalysts can serve as radicalization initiators. Examples of OCM catalysts can be found in U.S. Patent Publication No. 2012/0041246, U.S. Pat. No. 8,921, 256, 9,956,544 or 9,751,079, each of which is incorporated herein by reference in its entirety.

Some aspects of the present disclosure provide systems and methods for performing a catalytic reaction (e.g., an OCM reaction, an ODH reaction). Such systems and methods may provide a greater control of flow of gas and/or liquid carrying reagents and/or reaction products across the reactor, which may enable an operation of process at high flow velocities or with lower pressure drop as compared to a conventional reactor. Materials with different flow resistance properties may be used in a reactor for conducting a catalytic reaction. The materials may comprise solid materials. The materials may comprising a void material which has a high void fraction (e.g., a void fraction greater than or equal to about 55%, 60%, 65%, 70%, 75%, 80%, 85%, 90%, 95% or more). The void material may allow easy flow of gas along a length of a reactor. The materials may also comprise a catalytic material which may facilitate one or more catalytic reactions. The void material and the catalytic materials may be combined or mixed to form a hybrid/composite material. The hybrid material may comprise a certain percentage of the catalytic materials. In some cases, the hybrid material comprises greater than about 1%, 5%, 10%, 15%, 20%, 25%, 30%, 35%, 40% (mol %) catalytic materials, or more. In some cases, the hybrid materials comprises less than or equal to about 70%, 65%, 60%, 55%, 50%, 45%, 40%, 35%, 30%, 25% (mol %) catalytic materials, or less. In some cases, the hybrid material comprises catalytic materials at a concentration that falls between any two values described herein, e.g., between about 2% and about 40% (mol %). The hybrid packing may be self-assembled into the reactor vessel or reactor tubes in case of a multi-tubular reactor. The hybrid materials may be pre-assembled prior to loading. In some cases, the hybrid packing is a combination of pre-assembled and self-assembled packing.

Figure 33:
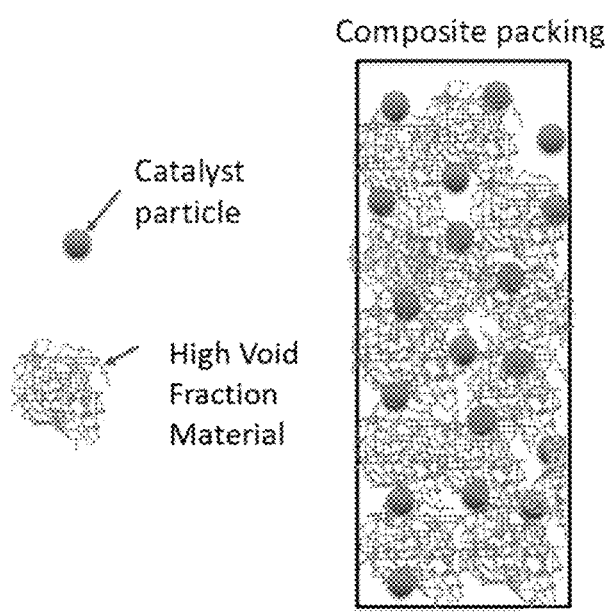
FIG. 33 shows an example reactor comprising a catalyst bed having a composite packing.

The catalytic materials may be contained in separate particles per-formed and mixed as a solid into the hybrid structure. In some cases, the catalytic materials are deposited as a film onto a surface of the void materials. Coating of the void material may be performed by washing-coating using a slurry, powder coating or other techniques such as chemical vapor deposition (CVD) or physical vapor deposition (PVD). In some cases, the high void fraction material is assembled around each individual catalytic particle. In some cases, the void materials are deposited as films. The catalytic materials (e.g., catalytic particles) may be deposited onto the films. In some cases, both materials (i.e., the void materials and the catalytic materials) are formed as films and multilayer composite materials maybe formed using the films. In some cases, the void materials are formed in secondary particles and loaded into the reactor at the same time as the catalytic materials are loaded. Depending on e.g., a ratio of sizes of the secondary particles to catalytic materials, or relevant volume/amount of each material loaded, the catalytic materials may well be dispersed in the hybrid bed (FIG. 33) or segregating from the void materials to form a network of the catalytic materials each being in direct contact with one another.

Various materials can be used as void materials. Non-limiting examples of the void materials may comprise pieces of ceramic foam, self-assembled stacks of highly anisotropic refractory particles (e.g., rods, thin rings or ring fragments, filaments, acicular crystals) with greater than or equal to about one millimeter (mm) length in a given direction, metal filament bundles and mesh, metal foams, wire bundles or foam, coater metal filament, mesh, foam, silicon carbide fibers, boron nitride fibers, carbon fibers (in reducing environments), acicular mullite, alumina reticulated foam, cordierite foams and extrudates pieces, electro-spun formed ceramic wires, stainless steel alloy wires, zirconia wires, titanium wires, nickel wires, inconel alloy wires, or combinations thereof. High void fraction foam and mesh can also be prepared by mixing fibers of different compositions. For example, Zirconia wires could be mixed with Stainless steel wires to form a mesh.

In some cases, the void materials are metal materials (such as metal mesh, wire bundles, metal foams or metal fibers). In some examples, the void materials are metal foams. The foam may be relatively isotropic at large scale. The foam material may have a pore per inch (PPI) that is greater than or equal to about 1, 5, 10, 20, 30, 40, 50, 60, 70, 80, 90, 100, 110, 120, or more. In some cases, the foam material has a PPI that is less than or equal to about 200, 180, 160, 150, 140, 130, 120, 110, 100, 80, 60, 40, 20, 10, or less. In some cases, the foam material has a PPI falling with a range of any two values described herein, e.g., between about 10 and about 100.

In cases where a reactor is a tubular reactor comprising metal walls, thermal contact between the reactor and the void materials may be improved by brazing and/or sintering the void materials into the tube.

Figure 34:
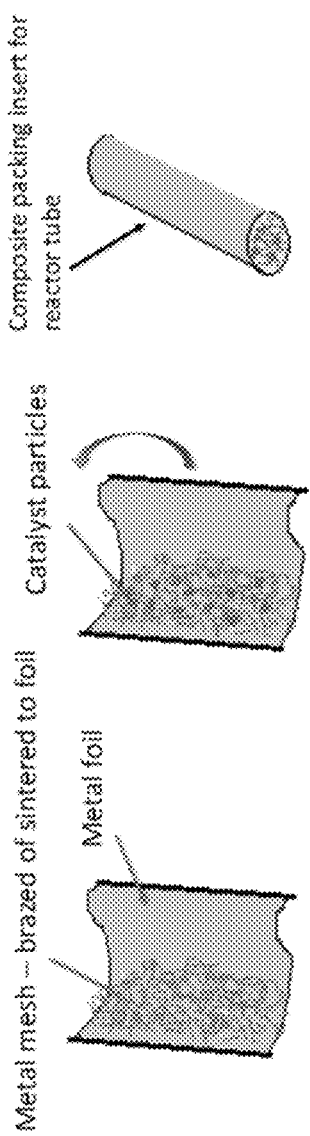
FIG. 34 shows an example reactor which comprises a foil wrap used for assembling void materials and catalytic materials within the reactor.

Alternatively or additionally, the void materials may be sintered and/or brazed onto a thin sheet (such as a liner in contact with an inner wall or surface of a reactor). The thin sheet may be a metal foil. The sheet may be flexible. The flexible sheet may conform to a shape of the reactor. The liner may be removed with the void materials and/or catalytic materials. The liner may be replaced. The liner may be disposable. The liner may be reused. The liner may be removed at a regular interval to dispose catalytic materials. FIG. 34 shows an example reactor which uses a foil wrap to assemble void materials and catalytic materials within the reactor tube.

Figure 35:
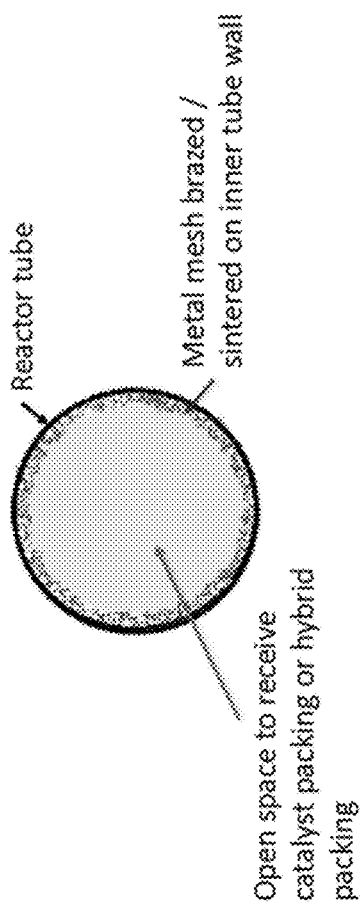
FIG. 35 shows an example reactor comprising a metal mesh brazed on an inner wall of the reactor.

In some examples, as illustrated in FIG. 35, the void materials are sintered/brazed near the inner surface of a reactor, leaving an open space inside the reactor for loading and/or unloading the catalytic materials (e.g., catalytic particles) and remaining void materials (i.e., void materials not sintered/brazed). Such systems/methods may facilitate heat transfer (e.g., heat removal) across the reactor and/or ease the loading/unloading of the catalytic materials by providing a buffer volume for catalytic particle growth or shrinking. In some cases, the void materials that are sintered/brazed onto the inner tube wall or surface are metal fibers or foam. Use of the metal fibers and foam may afford the system a greater tolerance to thermal cycling or gas composition cycling. The metal fibers or foam may be attached to the inner surface or wall which may take an annular space of between about 10% and 20% of the tube volume in case of a tubular reactor. Catalytic materials and/or additional void materials may be added into the middle of the tube.

In some cases, the catalytic reaction is an OCM reaction. In some situations, as the OCM reaction is operated over a large range of temperature, a significant portion of the reactor operating envelop is above auto-ignition limit for pressure and/or temperature of a feed stream. Thus, delaying the homogeneous build-up of combustion precursors which may lead to a rapid temperature rise and oxidizing agent consumption in the gas phase may be desirable. Solid surfaces (of e.g., the void materials) may interfere with this precursor build up and significantly delay auto-ignition events. In some examples, there is greater than about 4 times (4×) increase in auto-ignition delay time measured in 1" diameter test vessel when the test vessel is packed with a ceramic packing as opposed to left empty. In another example, using finely divided anisotropic solid filler adds a significant amount of solid surface to the reactor volume when compared to more standard ceramic packing. This higher surface area can be used to enable pre-heating the feed mixture to increased temperatures. Use of the finer divided material may also provide for a reduction in size of the gas interparticle void between solid surfaces. The reduction in gas void size may also decrease the propensity of the reactive gas mixture to ignite.

Similarly, as the OCM reaction progress, suppression of the gas phase reaction away from the catalyst particles surface may be important. It may be achieved by maximizing the speed of the catalytic reaction so as to remove the limiting reagent quickly from the feed mixture which deprives the homogeneous reaction pathway of reagent. This method may require the use of a reactor that allows short contact times. Using finely divided material to occupy the gaps between catalyst particle can relax the need for rapid removal of all of the limiting reagent (e.g., oxidizing agents in OCM) from the reaction mixture by converting highly active combustion reaction intermediates, which may facilitate the design of reactors that integrates heat removal and chemical conversion in more manageable volumes.

In some OCM reactor implementations, a substantially adiabatic reactor is closed coupled with an isotubular reactor and an amount of oxidizing agents (such as oxygen) slipping through the isotubular reactor may need to be controlled for proper operation of the system. Lowering the risk of process fluctuation associated with homogeneous reactions may be beneficial. When using void materials (such as metal fiber) as the filler, it may maintain a certain minimal level of oxidizing agents in the product mixture, thereby minimizing or eliminating run away coke built up on the metal surfaces.

Catalytic Pressure Swing Adsorption/Temperature Swing Adsorption

In some aspects, the present disclosure provides methods and systems for producing higher hydrocarbon compounds (e.g., hydrocarbon compounds with three or more carbon atoms). The methods may comprise directing a feed stream into a separations unit. The feed stream may comprise hydrocarbon compounds having two or more carbon atoms ($C_{2+}$ compounds) (e.g., ethane or ethylene). The separations unit may comprise a pressure swing adsorption (PSA) unit and/or a temperature swing adsorption (TSA) unit. The separations unit may be configured to separate (via e.g., adsorption) one or more compounds from remaining compounds of the feed stream. For example, the separations unit may be configured to selectively adsorb one or more certain type of compounds (e.g., $C_{2+}$ compounds). The adsorption may be performed at a first condition including e.g., temperature, pressure and/or gas hourly space velocity (GHSV).

Next, the first condition may be adjusted to a second condition (including e.g., temperature, pressure and/or GHSV) to desorb some or all of the compounds selectively adsorbed. Alternatively or additionally, some of the adsorbed compounds may be subject to a conversion reaction to product higher hydrocarbon compounds. In some cases, the feed stream comprises ethylene and the separations unit is configured to selectively adsorb at least a portion of the ethylene. In some cases, some or all of the ethylene that is selectively adsorbed is desorbed as the separations unit is operated at the second condition. In some cases, the ethylene conversion reaction comprises a dimerization reaction and/or an oligomerization reaction. In some cases, the higher hydrocarbon compounds comprise butane (e.g., 1-butene or 2-butene).

In some cases, the first condition comprises a first temperature, a first pressure and/or a first GHSV, and the second condition comprises a second temperature, a second pressure and/or a second GHSV. The first temperature may be different than (higher or lower than) the second temperature. The first pressure may be different than (higher or lower than) the second pressure. The first GHSV may be different than (higher or lower than) the second GHSV.

In some cases, the adsorption is operated at a lower temperature and/or higher pressure and the desorption occurs at a higher temperature and/or lower pressure. For example, the first temperature may be greater than or equal to about −20° C., −15° C., −10° C., −5° C., 0° C., 5° C., 10° C., 15° C., 20° C., 25° C., 30° C., 35° C., 40° C., 45° C., 50° C., 55° C., 60° C. or more. In some cases, the first temperature is less than or equal to about 70° C., 60° C., 50° C., 40° C., 30° C., 20° C., 10° C., 0° C., or less. In some cases, the first temperature is between any two values described herein, for example, between about −10° C. and about 50° C.

The first pressure may be greater than or equal to about 0 bar(a), 5 bar(a), 10 bar(a), 15 bar(a), 20 bar(a), 25 bar(a), 30 bar(a), 35 bar(a), 40 bar(a), 45 bar(a), 50 bar(a) or more. The first pressure can be less than or equal to about 60 bar(a), 50 bar(a), 40 bar(a), 30 bar(a), 20 bar(a), 10 bar(a), 5 bar(a) or less. In some cases, the first pressure is between any two values described herein, for example, between about 6 bar(a) and about 10 bar(a).

The first GHSV may be greater than or equal to about 100 $hr^{-1}$, 500 $hr^{-1}$, 1000 $hr^{-1}$, 2000 $hr^{-1}$, 3000 $hr^{-1}$, 4000 $hr^{-1}$, 5000 $hr^{-1}$, 6000 $hr^{-1}$, 7000 $hr^{-1}$, 8000 $hr^{-1}$, 9000 $hr^{-1}$, 10000 $hr^{-1}$, 12000 $hr^{-1}$, 14000 $hr^{-1}$, 16000 $hr^{-1}$, 18000 $hr^{-1}$, 20000 $hr^{-1}$, 22000 $hr^{-1}$, 24000 $hr^{-1}$ or more. In some cases, the first GHSV may be less than or equal to about 25000 $hr^{-1}$, 23000 $hr^{-1}$, 21000 $hr^{-1}$, 19000 $hr^{-1}$, 17000 $hr^{-1}$, 15000 $hr^{-1}$, 13000 $hr^{-1}$, 11000 $hr^{-1}$, 9000 $hr^{-1}$, 7000 $hr^{-1}$, 5000 $hr^{-1}$, 3000 $hr^{-1}$, 1000 $hr^{-1}$, 800 $hr^{-1}$, 600 $hr^{-1}$, 400 $hr^{-1}$, 200 $hr^{-1}$, 100 $hr^{-1}$, 50 $hr^{-1}$ or less. In some cases, the first GHSV is between any two values described herein, for example, between about 1000 $hr^{-1}$ and about 3000 $hr^{-1}$.

The second temperature may be greater than or equal to about 0° C., 5° C., 10° C., 20° C., 40° C., 60° C., 80° C., 100° C., 120° C., 140° C., 160° C., 180° C., 200° C., 220° C., 240° C., 260° C., 280° C., 300° C., 320° C., 340° C., 360° C., 380° C., 400° C. or more. In some cases, the second temperature is less than or equal to about 500° C., 450° C., 400° C., 350° C., 300° C., 250° C., 200° C., 150° C., 100° C., 80° C., 60° C., 40° C., 20° C., 10° C., 5° C. or less. In some cases, the second temperature is between any two values described herein, for example, between about 20° C. and about 350° C.

The second pressure may be greater than or equal to about 0 bar(a), 5 bar(a), 10 bar(a), 15 bar(a), 20 bar(a), 25 bar(a), 30 bar(a), 35 bar(a), 40 bar(a), 45 bar(a), 50 bar(a) or more. The second pressure can be less than or equal to about 60 bar(a), 50 bar(a), 40 bar(a), 30 bar(a), 20 bar(a), 10 bar(a), 5 bar(a) or less. In some cases, the second pressure is between any two values described herein, for example, between about 0 bar(a) and about 5 bar(a).

The second GHSV may be greater than or equal to about 100 $hr^{-1}$, 500 $hr^{-1}$, 1000 $hr^{-1}$, 2000 $hr^{-1}$, 3000 $hr^{-1}$, 4000 $hr^{-1}$, 5000 $hr^{-1}$, 6000 $hr^{-1}$, 7000 $hr^{-1}$, 8000 $hr^{-1}$, 9000 $hr^{-1}$, 10000 $hr^{-1}$, 12000 $hr^{-1}$, 14000 $hr^{-1}$, 16000 $hr^{-1}$, 18000 $hr^{-1}$, 20000 $hr^{-1}$, 22000 $hr^{-1}$, 24000 $hr^{-1}$ or more. In some cases, the second GHSV may be less than or equal to about 25000 $hr^{-1}$, 23000 $hr^{-1}$, 21000 $hr^{-1}$, 19000 $hr^{-1}$, 17000 $hr^{-1}$, 15000 $hr^{-1}$, 13000 $hr^{-1}$, 11000 $hr^{-1}$, 9000 $hr^{-1}$, 7000 $hr^{-1}$, 5000 $hr^{-1}$, 3000 $hr^{-1}$, 1000 $hr^{-1}$, 800 $hr^{-1}$, 600 $hr^{-1}$, 400 $hr^{-1}$, 200 hr$^{-1}$, 100 hr$^{-1}$, 50 hr$^{-1}$ or less. In some cases, the second GHSV is between any two values described herein, for example, between about 1000 hr$^{-1}$ and about 3000 hr$^{-1}$.

In some cases, the feed stream comprises ethylene and the separations unit is configured to selectively adsorb at least a portion of the ethylene. During the desorption, a higher desorption temperature (i.e, the second temperature) may decrease ethylene content while increase a content of hydrocarbon compounds with higher carbon atoms than ethylene (e.g., $C_3$, $C_4$, $C_5$ compounds) due to more conversion of ethylene in an ethylene conversion reaction. In some cases, increasing GHSV during desorption increases ethylene content and decreases a content of hydrocarbon compounds with higher carbon atoms than ethylene (e.g., $C_3$, $C_4$, $C_5$ compounds) due to less conversion of ethylene in an ethylene conversion reaction. In some cases, the ethylene conversion reaction comprises a dimerization reaction and/or an oligomerization reaction.

The feed stream may be an OCM effluent stream. The methods may further comprise directing a stream comprising methane and an oxidizing agent into an OCM reactor to producing the OCM effluent stream. The OCM effluent may be directed in the separations unit (e.g., a PSA/TSA unit) to selectively adsorb ethylene. During the desorption, at least a portion of the adsorbed ethylene may be desorbed and an additional portion of the adsorbed ethylene may be converted to the higher hydrocarbon compounds in an ethylene conversion reaction. The separation unit may yield a separations effluent stream comprising the higher hydrocarbon compounds. The separations effluent stream may be directed into a further reaction unit (e.g., a metathesis unit) to yield a product stream comprising product compounds (e.g., propylene).

The separations unit may comprise a material that facilitates ethylene selective adsorption and the ethylene conversion reaction. The material may be an adsorbent and/or a catalyst comprising catalytic materials. The material may comprise porous zeolites. The porous zeolites may comprise medium pore zeolites. The porous zeolites may have an average pore size greater than or equal to about 1 Å, 2 Å, 3 Å, 4 Å, 5 Å, 6 Å, 7 Å, 8 Å, 9 Å, 10 Å, 12 Å, 14 Å, 16 Å, or more. In some cases, the porous zeolites has an average pore size less than or equal to about 20 Å, 18 Å, 16 Å, 14 Å, 12 Å, 10 Å, 8 Å, 6 Å, 4 Å, 2 Å, 1 Å, or less. In some cases, the porous zeolites have an average pore size falling between any of the two values described herein, for example, between about 4 Å and about 8 Å. In some cases, the material comprises zeolites doped with transition metals, for example, transition metal doped Fe-ZSM-5, ZSM-5, ZSM-23 or combinations thereof with various Si/Al ratio (SAR). The material can be a single bed composition or a mixture/layering of materials within a single vessel or between different vessels of the separations unit.

Figure 36:
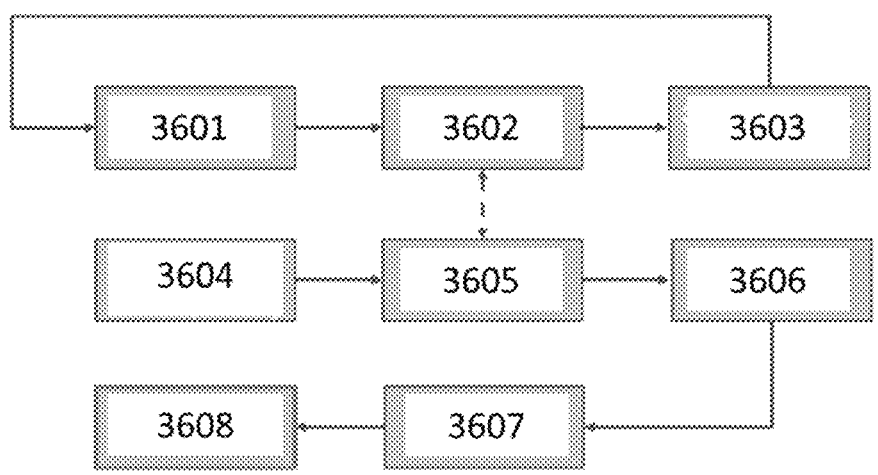
FIG. 36 illustrates an example method for producing hydrocarbon compounds comprising propylene using catalytic pressure swing adsorption (PSA) or temperature swing adsorption (TSA)

FIG. 36 illustrates an example method for producing hydrocarbon compounds comprising propylene. As shown in FIG. 36, an OCM product stream 3601 comprising ethylene may be generated. The OCM product stream may be directed into a separations unit comprising a PSA/TSA unit in which at least a portion of the ethylene may be selectively adsorbed 3602. Unadsorbed compounds may be directed out of the separations unit 3603. The unadsorbed compounds may comprise $CH_4$, $CO_2$, CO and/or $H_2$. Some or all of the compounds may be directed back to an OCM reactor and/or some additional reaction units. Upon a change of conditions of the separations unit (e.g., an increase in temperature and/or a decrease in pressure), some or all of the ethylene adsorbed may be desorbed 3605. A gas stream (e.g., a hot desorption ethane) at a moderate temperature (e.g., about 100° C., 150° C., 200° C., 250° C., or 300° C.) 3604 may be directed to the separations unit before or during the desorption of ethylene. In some cases, some of the ethylene is converted to higher hydrocarbons such as butene (including butene isomers) in an ethylene conversion reaction (such as dimerization or oligomerization) during the desorption 3606. An effluent stream may be generated during the desorption. The effluent stream may comprise butene and ethylene. The effluent stream may be directed in to a methathesis unit 3607 which may yield a product stream comprising hydrocarbon compounds such as propylene, ethane and ethylene.

Computer Systems

Figure 32:
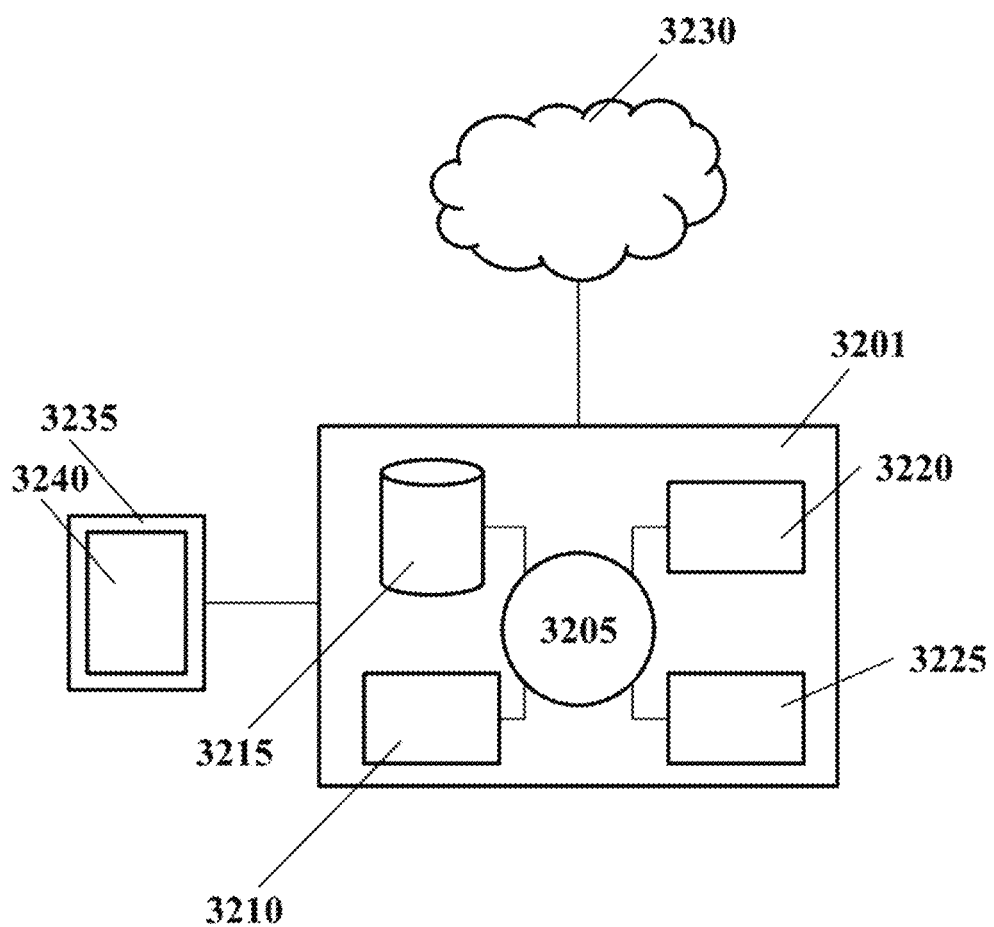
FIG. 32 shows a computer system that is programmed or otherwise configured to implement methods of the present disclosure, such as regulating a reaction.

The present disclosure provides computer control systems that are programmed or otherwise configured to implement methods provided herein, such as OCM reactions or processes of the present disclosure. FIG. 32 shows a computer system 3201 that includes a central processing unit (CPU, also "processor" and "computer processor" herein) 3205, which can be a single core or multi core processor, or a plurality of processors for parallel processing. The computer system 3201 also includes memory or memory location 3210 (e.g., random-access memory, read-only memory, flash memory), electronic storage unit 3215 (e.g., hard disk), communication interface 3220 (e.g., network adapter) for communicating with one or more other systems, and peripheral devices 3225, such as cache, other memory, data storage and/or electronic display adapters. The memory 3210, storage unit 3215, interface 3220 and peripheral devices 3225 are in communication with the CPU 3205 through a communication bus (solid lines), such as a motherboard. The storage unit 3215 can be a data storage unit (or data repository) for storing data. The computer system 3201 can be operatively coupled to a computer network ("network") 3230 with the aid of the communication interface 3220. The network 3230 can be the Internet, an internet and/or extranet, or an intranet and/or extranet that is in communication with the Internet. The network 3230 in some cases is a telecommunication and/or data network. The network 3230 can include one or more computer servers, which can enable distributed computing, such as cloud computing. The network 3230, in some cases with the aid of the computer system 3201, can implement a peer-to-peer network, which may enable devices coupled to the computer system 3201 to behave as a client or a server.

The CPU 3205 can execute a sequence of machine-readable instructions, which can be embodied in a program or software. The instructions may be stored in a memory location, such as the memory 3210. The instructions can be directed to the CPU 3205, which can subsequently program or otherwise configure the CPU 3205 to implement methods of the present disclosure. Examples of operations performed by the CPU 3205 can include fetch, decode, execute, and writeback.

The CPU 3205 can be part of a circuit, such as an integrated circuit. One or more other components of the system 3201 can be included in the circuit. In some cases, the circuit is an application specific integrated circuit (ΔSIC).

The storage unit 3215 can store files, such as drivers, libraries and saved programs. The storage unit 3215 can store user data, e.g., user preferences and user programs. The computer system 3201 in some cases can include one or more additional data storage units that are external to the computer system 3201, such as located on a remote server that is in communication with the computer system 3201 through an intranet or the Internet. The computer system 3201 can communicate with one or more remote computer systems through the network 3230.

Methods as described herein can be implemented by way of machine (e.g., computer processor) executable code stored on an electronic storage location of the computer system 3201, such as, for example, on the memory 3210 or electronic storage unit 3215. The machine executable or machine readable code can be provided in the form of software. During use, the code can be executed by the processor 3205. In some cases, the code can be retrieved from the storage unit 3215 and stored on the memory 3210 for ready access by the processor 3205. In some situations, the electronic storage unit 3215 can be precluded, and machine-executable instructions are stored on memory 3210.

The code can be pre-compiled and configured for use with a machine having a processor adapted to execute the code, or can be compiled during runtime. The code can be supplied in a programming language that can be selected to enable the code to execute in a pre-compiled or as-compiled fashion.

The computer system 3201 can be programmed or otherwise configured to regulate one or more parameters, such as various parameters associated with OCM reactions/processes or OCM systems.

Aspects of the systems and methods provided herein, such as the computer system 3201, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 3201 can include or be in communication with an electronic display 3235 that comprises a user interface (UI) 3240 for providing, for example, signals from a chip with time. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 3205.

EXAMPLES

Example 1: Non-Adiabatic and Substantially Adiabatic OCM Reactor

An oxidative coupling of methane reactor was constructed that included a U-shaped one inch inner diameter pipe immersed in a molten salt tank, which was insulated. About 40 cm of the reactor was loaded with oxidative coupling of methane catalyst. The section of the pipe upstream of the oxidative coupling of methane catalyst contained inert packing composed of alumina ($Al_2O_3$). The molten salt bath temperature was about 550° C. A mixture of oxygen and methane was injected into the section of the reactor that held inert packing at a pressure of about 4 bar(g). The section that held inert packing served as a feed gas preheater. The section of the tube that is downstream of the section that contains oxidative coupling of methane catalyst was not in contact with the molten salt, and was considered substantially adiabatic. The methane to oxygen ratio at the inlet of the reactor was 6:1, and the methane conversion was 19%. The peak temperature in the reactor was 925° C.

Figure 17:
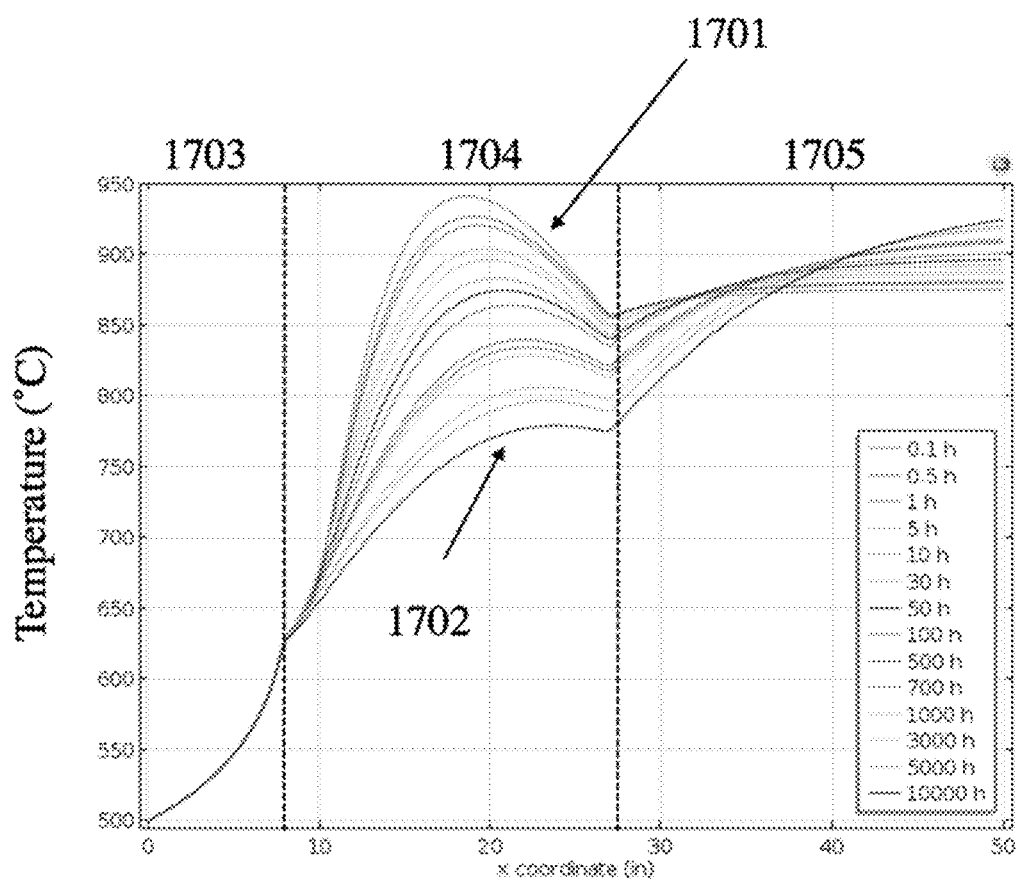
FIG. 17 shows a result of a simulation that calculates the temperature profile in an oxidative coupling of methane reactor.

Example 2: Catalyst Deactivation Effect on Non-Adiabatic and Substantially Adiabatic OCM Reactor FIG. 17 shows the result of a simulation that calculates the temperature profile in an oxidative coupling of methane reactor. A simulation of the oxidative coupling of methane reaction was conducted in a tubular reactor that contained three sections: a substantially adiabatic section that did not contain oxidative coupling of methane catalyst 1703, a non-adiabatic section that was in thermal communication with a heat transfer medium and contained oxidative coupling of methane catalyst 1704, and finally a substantially adiabatic section that did not contain oxidative coupling of methane catalyst 1705. In the simulation a mixture of oxygen and methane were fed into the first section at a temperature of about 500° C. At the exit of the first substantially adiabatic section, the temperature of the gas was about 640° C. The gas then traveled into a non-adiabatic section within 5 milliseconds (ms) of exiting the first substantially adiabatic section. The temperature peaked about half way through the non-adiabatic section, and its peak temperature as well as the temperature at the exit of the non-adiabatic section depended on the catalyst deactivation percentage. The fresh catalyst (about 0% deactivation), the peak temperature was about 940° C. and had an exit temperature of about 860° C. 1701. Over time, the catalyst became more deactivated. After 10,000 hours of operation, the peak temperature in the non-adiabatic section was about 770° C. and had an exit temperature of about 760° C. 1702. The gas was then injected into the second substantially adiabatic section within 5 milliseconds (ms) of exiting the non-adiabatic section. In the second substantially adiabatic section, the gas temperature monotonically increased. In the case of the fresh catalyst, the final exit temperature was about 870° C. In the case of the catalyst after 10,000 hours of operation, the final exit temperature was about 925° C.

Example 3: Improvement in Methane Conversion Using Steam Dilution

Methane and oxygen were injected into a reactor containing an oxidative coupling of methane catalyst, and the effect of using steam as a diluent on methane conversion was measured. With no steam addition, the methane conversion was about 12.5%. Increasing the water dilution to 15%, 30%, and 40%, the methane yield increased to 13.2%, 14%, and 14.5%, respectively.

Example 4—Radical Transfer Agents

Figure 24:
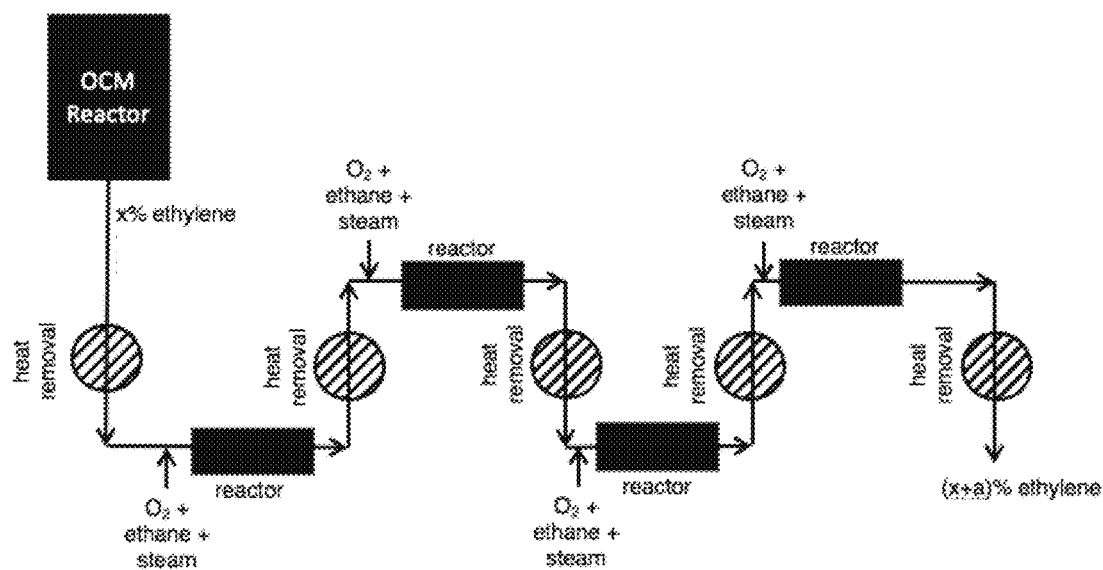
FIG. 24 shows an example of a multistage system for increasing olefin concentrations in an oxidative coupling of methane effluent stream.

Additional ethane, $O_2$, and steam are added to convert to additional ethylene, as shown in FIG. 24 (e.g., in order to increase the concentration of ethylene in the product gas from an OCM reactor). The OCM effluent, including of x % ethylene, y % ethane, and z % methane, is cooled using a heat exchanger. The process can increase the concentration of ethylene in this stream above x %. To do this, additional ethane, $O_2$, and steam are added, which correspond to the alkane, $O_2$, and radical transfer agent described herein. The unconverted methane from the OCM reactor can also serve as the radical transfer agent, and there may be additional alkanes in the stream including propane that can convert into additional olefin including ethylene and propylene. The amount of $O_2$ and ethane that are added is such that the resulting mixture entering the reactor is 6 mol % $O_2$ and 5.5 mol % ethane in this example. This mixture is then fed into an empty reaction vessel at 500° C. When in the reactor, the oxygen begins to catalyze the production of methyl ($H_3C.$) and hydroxyl (HO.) radicals from the radical transfer agents methane and water, respectively.

Figure 25:
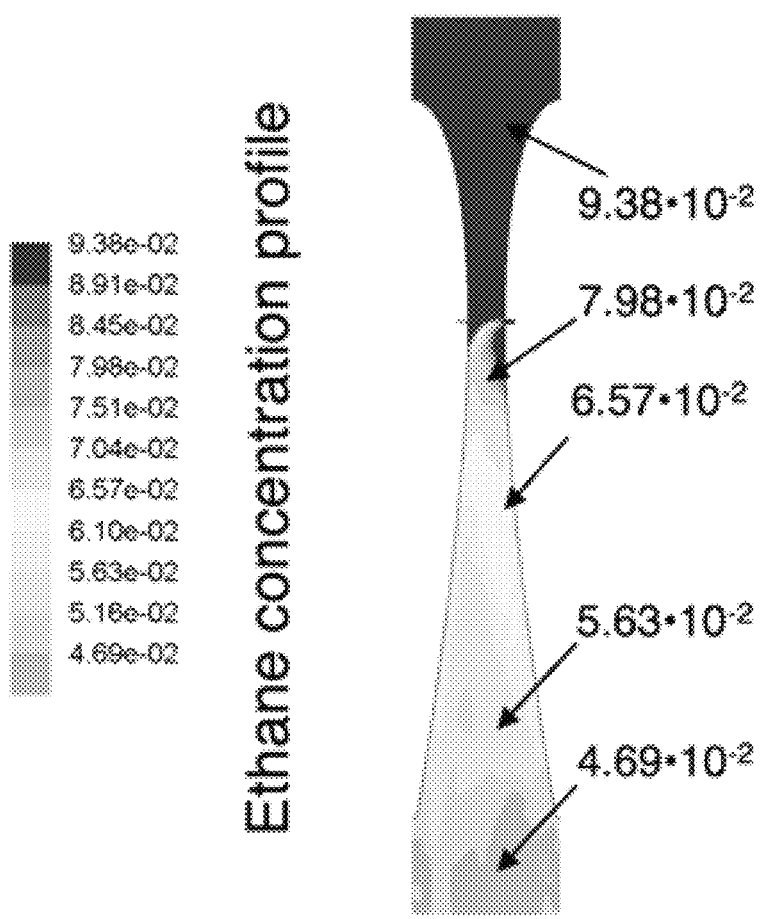
FIG. 25 shows an example concentration profile of ethane while reacting with oxygen and methane in a vessel.

FIG. 25 shows a simulation of ethane concentration inside the reactor. Initially, the ethane concentration does not change significantly, and then converts to ethylene.

Figure 26:
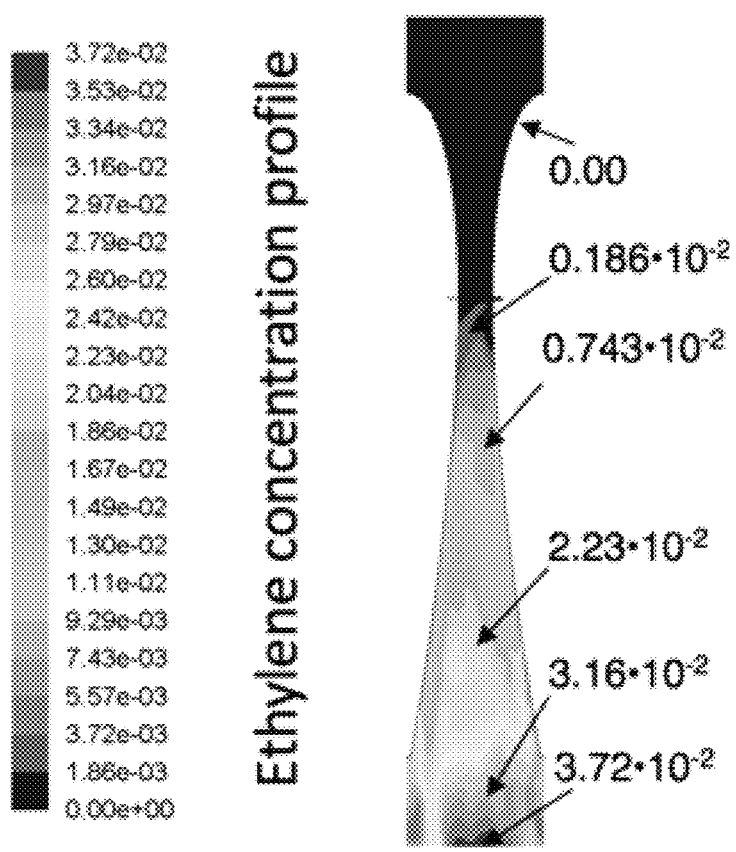
FIG. 26 shows an example concentration profile of ethylene generated from a reaction of ethane with oxygen and methane.

FIG. 26 shows a simulation of ethylene concentration inside the reactor. The ethylene generation profile roughly matches the ethane depletion profile, because ethane is being converted to ethane inside the reactor.

Figure 27:
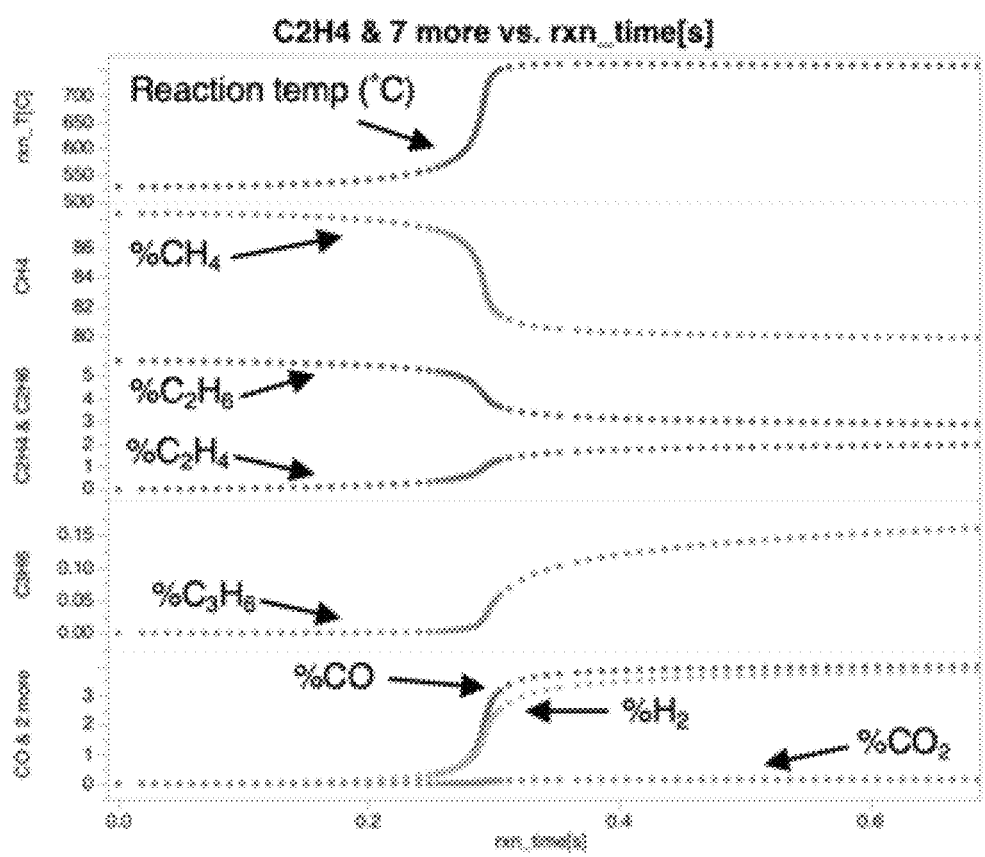
FIG. 27 shows example concentration and temperature profiles that describe behavior of a reaction in a vessel.

FIG. 27 shows a simulation of the reaction temperature, as well as the concentrations of methane, ethane, ethylene, propylene, carbon monoxide (CO), hydrogen ($H_2$), and carbon dioxide ($CO_2$) over time within the reactor. A case is simulated where the entering mixture contains 6 mol % $O_2$. The temperature as well as the concentrations remain roughly constant until about 250 milliseconds (ms), which is the auto-ignition delay time (AIDT) in this case. This is the time at which the concentration of radicals have become sufficient to sustain a chain reaction that converts the reaction mixture to a product mixture. The temperature rapidly climbs from about 500° C. to about 800° C., the ethane rapidly depletes and ethylene forms. Some ethane is converted to CO and $H_2$, however there is only minimal formation of $CO_2$.

Figure 28:
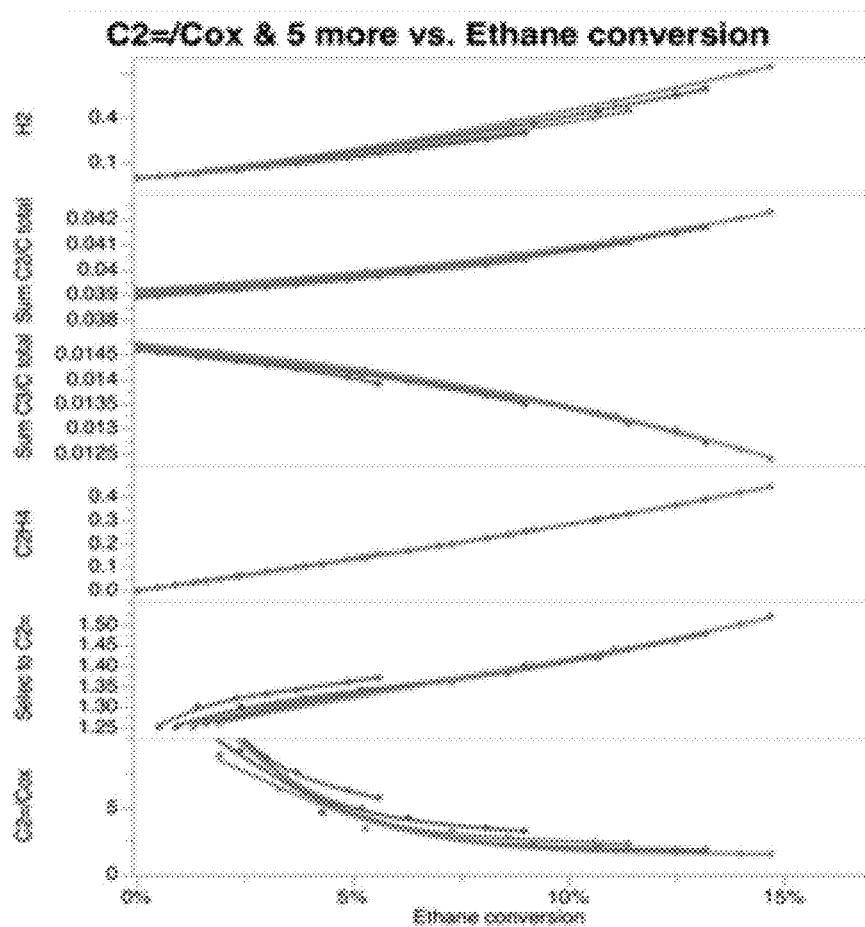
FIG. 28 shows examples of reactions and selectivities.

FIG. 28 shows the results of a simulation of this reaction under varying inlet conditions. From this, it is seen that the apparent selectivity for ethylene is greater than 100%, due to conversion of propane as well as ethane to ethylene. The carbon efficiency, estimated from the percentage of ethylene that is formed relative to CO and $CO_2$, is between 60% and 80%.

The end result of the reaction in the reactor is that there is additional ethylene concentration in its effluent. This high temperature effluent, now at about 800° C., is cooled back to 500° C. using a heat exchanger. Additional $O_2$, steam, and ethane are added to the stream, and this new reaction mixture flows into another vessel. The resulting product gas is once again enriched in ethylene. This process is repeated twice more, in order to further increase the concentration of ethylene in the product gas. Finally, the product mixture is cooled to room temperature, to result in product that has an ethylene concentration of (x+a) %, where a is a number greater than zero.

Example 5—Air-Fed OCM Integrated with Methanol Production

In some cases, an OCM reaction can be integrated with the production of methanol (MeOH). Such integrations are described in U.S. patent application Ser. No. 15/690,090, which is incorporated herein by reference in its entirety. As described herein, the OCM reaction can be fed with air, i.e., instead of $O_2$. In some cases, the OCM reaction can use partially enriched oxygen. In the case where the de-methanizer overhead stream becomes the reformer feed stream (i.e., a once-through case without methanation), the methanol plan can be designed to handle the $N_2$ content in the steam methane reformer (SMR) feed stream. This design takes advantage of an economic trade-off between the capital expenditure increase in the methanol plant compared with the cost of an air separation unit being avoided.

Example 6—Dry Gas Case without PBC

The inlet gas stream to the reactor is: $O_2$ 12 mol %; $C_2H_6$<1 mol %; $H_2$, $H_2O$, $CO_2$<1 mol %; and the balance $CH_4$. The reactor conditions are: $T_{salt}$=700° C.; $T_{inlet}$=500° C.; and $T_{outlet}$=700° C. with a pressure of 8 barg. The reactor has a length of 36 inches, and inner diameter of 0.5". The gas hourly space velocity is 30000 $hr^{-1}$. The reactor outlet conditions are shown in Table 1.

TABLE 1

| Reactor outlet for Example 6 | | |
|---|---|---|
| CO | 2.10% | Selectivity: |
| CO2 | 4.85% | 73% |
| Ethane | 3.83% | |
| Ethylene | 4.62% | |

TABLE 1-continued

| Reactor outlet for Example 6 | | |
|---|---|---|
| Propane | 0.11% | CH$_4$ Conversion: |
| Propylene | 0.52% | 20% |
| Methane | 59.0% | |
| O$_2$ | 0.0% | |
| H$_2$ | 8.0% | C2+ Yield: |
| H$_2$O | 12.27% | 14.6 |

Example 7—Case of Natural Gas with Ethane Injection without PBC

The inlet gas stream to the reactor is: O$_2$ 12 mol %; C$_2$H$_6$ 10 mol %; H$_2$, H$_2$O, CO$_2$<1 mol %; and the balance CH$_4$. The reactor conditions are: T$_{salt}$=700° C.; T$_{inlet}$=500° C.; and T$_{outlet}$=700° C. with a pressure of 8 barg. The reactor has a length of 36 inches, and inner diameter of 0.5". The gas hourly space velocity is 30000 hr$^{-1}$. The reactor outlet conditions are shown in Table 2.

TABLE 2

| Reactor outlet for Example 7 | | |
|---|---|---|
| CO | 2.34% | Selectivity: |
| CO2 | 5.11% | 77% (Net) |
| Ethane | 3.53% | |
| Ethylene | 10.43% | |
| Propane | 0.40% | CH$_4$ Conversion: |
| Propylene | 0.40% | 20% |
| Methane | 54.3% | |
| O$_2$ | 0.0% | |
| H$_2$ | 12.01% | C2+ Yield: |
| H$_2$O | 11.47% | 14.6 |

Example 8—Case of Natural Gas with Ethane Injection without PBC

The inlet gas stream to the reactor is: O$_2$ 12 mol %; C$_2$H$_6$ 10 mol %; H$_2$, H$_2$O, CO$_2$<1 mol %; and the balance CH$_4$. The reactor conditions are: T$_{salt}$=700° C.; T$_{inlet}$=500° C.; and T$_{outlet}$=700° C. with a pressure of 8 barg. The reactor has a length of 36 inches, and inner diameter of 0.5". The gas hourly space velocity is 30000 hr$^{-1}$. The catalyst is NaM-nWO$_4$—SiO$_2$. The reactor outlet conditions are shown below in Table 3.

TABLE 3

| Reactor outlet for Example 8 | | |
|---|---|---|
| CO | 3.11% | Selectivity: |
| CO2 | 0.83% | 86% (Net) |
| Ethane | 2.91% | |
| Ethylene | 12.26% | |
| Propane | 0.27% | CH$_4$ Conversion: |
| Propylene | 0.50% | 20% |
| Methane | 62.8% | |
| O$_2$ | 0.0% | |
| H$_2$ | 4.63% | C2+ Yield: |
| H$_2$O | 12.70% | 14.6 |

Example 9—Operation of an OCM Reactor

Figure 30:
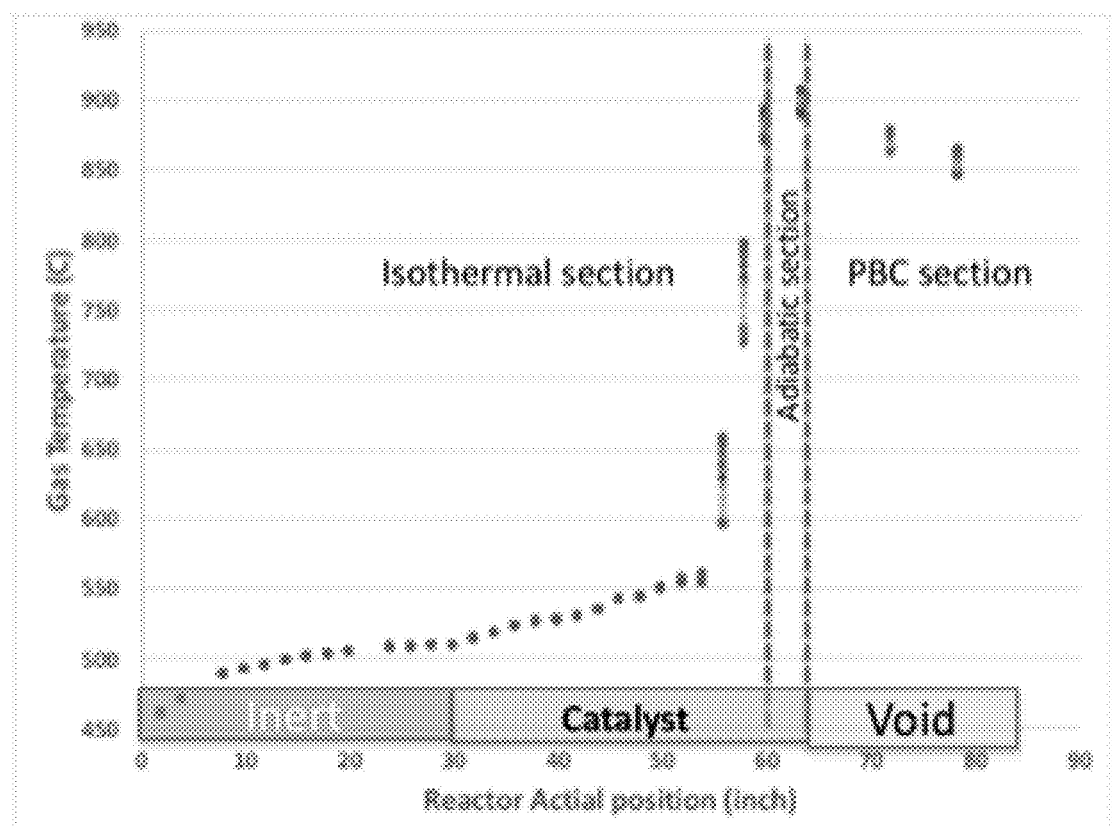
FIG. 30 shows an example of operation of an OCM reactor comprising an isothermal section, an adiabatic section, and a post-bed cracking section.

With reference to FIG. 30, an OCM reactor was operated that had an isothermal section, an adiabatic section, and a post-bed cracking section. The isothermal section had an inert section without catalyst and a section with an OCM catalyst. As shown, the gas temperature was monitored versus position along the reactor. The reactor performed a successful OCM reaction.

It will be appreciated that systems and methods described herein are provided as examples and that various alternatives may be employed. It will be further appreciated that components of systems described herein are interchangeable.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for producing an olefin, the method comprising:
    (a) providing a reactor comprising two sections: an isothermal tubular section and a substantially adiabatic section, wherein said isothermal tubular section contains a first oxidative coupling of methane (OCM) catalyst configured to promote a first OCM reaction and is in thermal communication with a heat transfer medium;
    (b) introducing a gas mixture into the isothermal tubular section of the reactor, which gas mixture comprises oxygen (O$_2$) and methane (CH$_4$), whereby at least about 75 mol % of the O$_2$ reacts with the CH$_4$ to produce an intermediate gas stream comprising hydrocarbon compounds having two or more carbon atoms (C$_{2+}$ compounds) and non-C$_{2+}$ impurities, wherein said first OCM catalyst undergoes deactivation over time such that (i) an outlet temperature of the isothermal tubular section decreases over time, (ii) an oxygen concentration at the outlet of the isothermal tubular section increases over time, and (iii) the oxygen concentration at the outlet of the isothermal tubular section is at least about 500 parts per million (ppm);
    (c) injecting the intermediate gas stream into said substantially adiabatic section, wherein said substantially adiabatic section contains a second OCM catalyst to promote a second OCM reaction, wherein said second OCM catalyst undergoes deactivation over time such that (i) an outlet temperature of said substantially adiabatic section increases over time and (ii) an oxygen concentration at an outlet of said substantially adiabatic section is less than about 100 ppm; and
    (d) generating a reactor effluent gas stream from said intermediate gas stream, wherein the reactor effluent gas stream comprises hydrocarbon compounds having C$_{2+}$ compounds and non-C$_{2+}$ impurities.

2. The method of claim 1, wherein the first OCM reaction has a selectivity for $C_{2+}$ compounds of at least about 50% at 700° C.

3. The method of claim 1, further comprising:
directing said reactor effluent gas stream into a post-bed cracking (PBC) section in fluid communication with and downstream of said substantially adiabatic section, wherein said PBC section converts ethane ($C_2H_6$) in said reactor effluent gas stream into ethylene ($C_2H_4$) using heat derived from the second OCM reaction.

4. The method of claim 1, wherein the heat transfer medium is a molten salt.

5. The method of claim 1, wherein the first OCM catalyst provides for the first OCM reaction to have a selectivity for $C_{2+}$ compounds of at least about 30% at 550° C.

6. The method of claim 1, wherein the first OCM catalyst provides for the first OCM reaction to have a selectivity for $C_{2+}$ compounds of at least about 40% at 600° C.

7. The method of claim 1, wherein the reactor further comprises a light off section in fluid communication with and upstream of the isothermal tubular section, which light-off section is in thermal communication with an additional heat transfer medium comprising a molten salt, and a heating section in fluid communication with and upstream of the light-off section, which heating section is in thermal communication with a further additional heat transfer medium, which further additional heat transfer medium comprises a molten salt.

8. The method of claim 1, wherein the gas mixture has a temperature between about 450° C. and about 580° C.

9. The method of claim 1, wherein the intermediate gas stream has a temperature between about 650° C. and about 750° C.

10. The method of claim 1, wherein the gas mixture contains between about 15 mol % and about 20 mol % $O_2$.

11. The method of claim 1, wherein the intermediate gas stream contains at least about 1 mol % $O_2$.

12. The method of claim 1, wherein between about 1 mol % and about 5 mol % of the $CH_4$ from the intermediate gas mixture is converted to $C_{2+}$ compounds and non-$C_{2+}$ impurities in the substantially adiabatic section.

13. The method of claim 1, wherein the first OCM catalyst comprises nanowires.

14. The method of claim 1, wherein the second OCM catalyst comprises nanowires.

15. The method of claim 1, wherein at least about 10 mol % of the $O_2$ from the gas mixture reacts with the $CH_4$ to produce $C_{2+}$ compounds and non-$C_{2+}$ impurities in the substantially adiabatic section of the reactor.

16. The method of claim 1,
wherein the second OCM catalyst has a different deactivation than a deactivation of the first OCM catalyst.

17. The method of claim 1, wherein the second OCM reaction has a net selectivity for $C_{2+}$ compounds of at least about 5% at greater than 850° C.

18. The method of claim 1, wherein said intermediate gas stream comprises unreacted $CH_4$ and wherein less than about 10 mol % of the unreacted $CH_4$ is reformed into CO and $H_2$.

19. The method of claim 3, further comprising:
injecting between about 1 mol % and 5 mol % of ethane ($C_2H_6$) via an additional gas stream into the reactor gas effluent stream near an inlet of the PBC section; and
converting at least a portion of the $C_2H_6$ in said additional gas stream into ethylene ($C_2H_4$) using heat derived from the second OCM reaction.

\* \* \* \* \*